(12) United States Patent
Borhani et al.

(10) Patent No.: US 8,940,873 B2
(45) Date of Patent: Jan. 27, 2015

(54) CRYSTALLINE ANTI-HUMAN IL-12 ANTIBODIES

(71) Applicant: AbbVie Inc., North Chicago, IL (US)

(72) Inventors: David W. Borhani, Hartsdale, NY (US); Wolfgang Fraunhofer, Newton, MA (US); Hans-Juergen Krause, Biblis (DE); Anette Koenigsdorfer, Ilvesheim (DE); Gerhard Winter, Penzberg (DE); Stefan Gottschalk, Grunwald (DE)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 13/762,171

(22) Filed: Feb. 7, 2013

(65) Prior Publication Data

US 2014/0017256 A1  Jan. 16, 2014

Related U.S. Application Data

(63) Continuation of application No. 13/396,563, filed on Feb. 14, 2012, now Pat. No. 8,404,819, which is a continuation of application No. 12/079,434, filed on Mar. 27, 2008, now Pat. No. 8,168,760.

(60) Provisional application No. 60/920,608, filed on Mar. 29, 2007.

(51) Int. Cl.
| | |
|---|---|
| *C07K 16/00* | (2006.01) |
| *G01N 31/00* | (2006.01) |
| *C07K 16/24* | (2006.01) |
| *A61K 39/395* | (2006.01) |
| *C30B 7/00* | (2006.01) |

(52) U.S. Cl.
CPC ......... *C07K 16/244* (2013.01); *A61K 39/39591* (2013.01); *C30B 7/00* (2013.01); *C07K 2299/00* (2013.01)
USPC ........................................ 530/388.15; 436/4

(58) Field of Classification Search
None
See application file for complete search history.

(56) References Cited

U.S. PATENT DOCUMENTS

| | | |
|---|---|---|
| 4,597,966 A | 7/1986 | Zolton et al. |
| 4,816,397 A | 3/1989 | Boss et al. |
| 4,877,608 A | 10/1989 | Lee et al. |
| 4,897,465 A | 1/1990 | Cordle et al. |
| 5,231,024 A | 7/1993 | Moeller et al. |
| 5,530,101 A | 6/1996 | Queen et al. |
| 5,608,038 A | 3/1997 | Eibl et al. |
| 5,643,768 A | 7/1997 | Kawasaki |
| 5,650,492 A | 7/1997 | Gately et al. |
| 5,652,138 A | 7/1997 | Burton et al. |
| 5,658,754 A | 8/1997 | Kawasaki |
| 5,780,597 A | 7/1998 | Gately et al. |
| 5,792,838 A | 8/1998 | Smith et al. |
| 5,811,523 A | 9/1998 | Trinchieri et al. |
| 5,853,697 A | 12/1998 | Strober et al. |
| 5,910,486 A | 6/1999 | Curiel et al. |
| 5,945,098 A | 8/1999 | Sarno et al. |
| 6,090,382 A | 7/2000 | Salfeld et al. |
| 6,171,586 B1 | 1/2001 | Lam et al. |
| 6,267,958 B1 | 7/2001 | Andya et al. |
| 6,284,282 B1 | 9/2001 | Maa et al. |
| 6,342,634 B2 | 1/2002 | Nicholson et al. |
| 6,436,397 B1 | 8/2002 | Baker et al. |
| 6,485,725 B1 | 11/2002 | Hirao et al. |
| 6,685,940 B2 | 2/2004 | Andya et al. |
| 6,693,173 B2 | 2/2004 | Mamidi et al. |
| 6,713,610 B1 | 3/2004 | Kucherlapati et al. |
| 6,737,405 B2 | 5/2004 | Roemisch et al. |
| 6,902,734 B2 | 6/2005 | Giles-Komar et al. |
| 6,914,128 B1 | 7/2005 | Salfeld et al. |
| 7,060,268 B2 | 6/2006 | Andya et al. |
| 7,063,964 B2 | 6/2006 | Giles-Komar et al. |
| 7,166,285 B2 | 1/2007 | Giles-Komar et al. |
| 7,279,157 B2 | 10/2007 | Giles-Komar et al. |
| 7,504,485 B2 | 3/2009 | Salfeld et al. |
| 7,560,247 B2 | 7/2009 | Giles-Komar et al. |
| 7,776,331 B1 | 8/2010 | Chartash et al. |
| 7,883,704 B2 | 2/2011 | Salfeld et al. |
| 2002/0136719 A1* | 9/2002 | Shenoy et al. ............. 424/130.1 |
| 2002/0161199 A1 | 10/2002 | Ashkenazi et al. |
| 2002/0194631 A1 | 12/2002 | Ehrhardt et al. |
| 2003/0070185 A1 | 4/2003 | Jakobovits et al. |
| 2003/0143603 A1 | 7/2003 | Giles-Komar et al. |
| 2003/0148955 A1 | 8/2003 | Pluenneke |

(Continued)

FOREIGN PATENT DOCUMENTS

| | | |
|---|---|---|
| EP | 0419251 A1 | 3/1991 |
| EP | 0638644 A1 | 2/1995 |

(Continued)

OTHER PUBLICATIONS

Jen et al., "Diamonds in the Rough: Protein Crystals from a Formulation Perspective", Pharmaceutical Research, Nov. 2001, vol. 18, No. 11, pp. 1483-1488.*

Schoenhaut DS et al. "Cloning and expression of murine IL-12." J Immunol. Jun. 1, 1992;148(11):3433-40.

Vaughan TJ. "Human antibodies by design." Nat Biotechnol. 1998 16(6):535-9.

Balashov, K.E., et al. "Increased interleukin 12 production in progressive multiple sclerosis induction by activated CD4+ T cells via CD40 ligand." Proc Natl Acad Sci USA. Jan. 21, 1997;94(2):599-603.

Barbas, III, C.F., et al. "Assembly of combinatorial antibody libraries on phage surfaces: the gene III site." Proc Natl Acad Sci USA. Sep. 15, 1991; 88:7978-82.

(Continued)

*Primary Examiner* — Suzanne M Noakes
(74) *Attorney, Agent, or Firm* — McCarter & English, LLP; Maria Laccotripe Zacharakis; Kevin A. Fiala

(57) ABSTRACT

The invention relates to batch crystallization methods for crystallizing an anti-hIL-12 antibody that allows the production of the antibody on an industrial scale, antibody crystals obtained according to the methods, compositions containing the crystals, and methods of using the crystals and the compositions.

19 Claims, 8 Drawing Sheets

(56) References Cited

U.S. PATENT DOCUMENTS

| | | |
|---|---|---|
| 2004/0038878 A1 | 2/2004 | Tanikawa et al. |
| 2004/0105889 A1 | 6/2004 | Ryde et al. |
| 2004/0156835 A1 | 8/2004 | Imoto et al. |
| 2004/0170623 A1 | 9/2004 | Arvinte et al. |
| 2004/0185091 A1 | 9/2004 | Truong-Le et al. |
| 2004/0191243 A1 | 9/2004 | Chen et al. |
| 2004/0191265 A1 | 9/2004 | Schenerman et al. |
| 2004/0197324 A1 | 10/2004 | Liu et al. |
| 2005/0019794 A1 | 1/2005 | Nassef et al. |
| 2005/0147610 A1 | 7/2005 | Ghayur et al. |
| 2005/0159364 A1 | 7/2005 | Cooper |
| 2005/0214278 A1 | 9/2005 | Kakuta et al. |
| 2005/0250704 A1 | 11/2005 | Bassarab et al. |
| 2005/0276823 A1 | 12/2005 | Cini et al. |
| 2006/0088523 A1 | 4/2006 | Andya et al. |
| 2006/0115472 A1 | 6/2006 | Li et al. |
| 2006/0142549 A1 | 6/2006 | Takeda et al. |
| 2006/0149042 A1 | 7/2006 | Konstantinov et al. |
| 2006/0210557 A1 | 9/2006 | Luisi et al. |
| 2006/0269479 A1 | 11/2006 | Colton et al. |
| 2006/0275306 A1 | 12/2006 | Andya et al. |
| 2007/0009526 A1 | 1/2007 | Benson et al. |
| 2007/0020255 A1 | 1/2007 | Ueno et al. |
| 2007/0065440 A1 | 3/2007 | Tomlinson et al. |
| 2007/0122402 A1 | 5/2007 | Bolli et al. |
| 2007/0172475 A1 | 7/2007 | Matheus et al. |
| 2007/0184045 A1 | 8/2007 | Doctor et al. |
| 2007/0202051 A1 | 8/2007 | Schuschnig |
| 2007/0212346 A1 | 9/2007 | Igawa et al. |
| 2007/0237762 A1 | 10/2007 | Winter |
| 2007/0269463 A1 | 11/2007 | Donovan |
| 2008/0071063 A1 | 3/2008 | Allan et al. |
| 2008/0089849 A1 | 4/2008 | Schultz-Fademrecht et al. |
| 2008/0139792 A1 | 6/2008 | Sek et al. |
| 2008/0200655 A1 | 8/2008 | Sek |
| 2008/0275220 A1 | 11/2008 | Friess et al. |
| 2008/0305114 A1 | 12/2008 | Salfeld et al. |
| 2008/0311078 A1 | 12/2008 | Gokarn et al. |
| 2009/0131639 A1 | 5/2009 | Kakuta et al. |
| 2009/0148406 A1 | 6/2009 | Jezek |
| 2009/0148513 A1 | 6/2009 | Fraunhofer et al. |
| 2009/0175857 A1 | 7/2009 | Salfeld et al. |
| 2009/0202557 A1 | 8/2009 | Argiriadi et al. |
| 2009/0226530 A1 | 9/2009 | Lassner et al. |
| 2009/0269302 A1 | 10/2009 | Salfeld et al. |
| 2009/0291062 A1 | 11/2009 | Fraunhofer et al. |
| 2010/0028363 A1 | 2/2010 | Valdes et al. |
| 2010/0034823 A1 | 2/2010 | Borhani et al. |
| 2010/0160894 A1 | 6/2010 | Julian et al. |
| 2010/0172862 A1 | 7/2010 | Correia et al. |
| 2010/0278822 A1 | 11/2010 | Fraunhofer et al. |
| 2010/0297143 A1 | 11/2010 | Chartash et al. |
| 2011/0054414 A1 | 3/2011 | Shang et al. |
| 2011/0123544 A1 | 5/2011 | Salfeld et al. |

FOREIGN PATENT DOCUMENTS

| | | |
|---|---|---|
| EP | 0659766 A1 | 6/1995 |
| EP | 0953639 A1 | 11/1999 |
| WO | WO-92/01047 A1 | 1/1992 |
| WO | WO-92/09690 A2 | 6/1992 |
| WO | WO-92/20791 A1 | 11/1992 |
| WO | WO-94/04679 A1 | 3/1994 |
| WO | WO-95/03826 A1 | 2/1995 |
| WO | WO-95/14780 A2 | 6/1995 |
| WO | WO-95/24918 A1 | 9/1995 |
| WO | WO-96/33735 A1 | 10/1996 |
| WO | WO-97/04801 A1 | 2/1997 |
| WO | WO-97/15327 A1 | 5/1997 |
| WO | WO-97/45140 A1 | 12/1997 |
| WO | WO-98/16248 A1 | 4/1998 |
| WO | WO-98/22137 A1 | 5/1998 |
| WO | WO-98/41232 A2 | 9/1998 |
| WO | WO-98/42376 A1 | 10/1998 |
| WO | WO-98/42378 A1 | 10/1998 |
| WO | WO-98/44948 A2 | 10/1998 |
| WO | WO-98/56418 A1 | 12/1998 |
| WO | WO-99/09055 A2 | 2/1999 |
| WO | WO-99/22766 A2 | 5/1999 |
| WO | WO-99/37682 A2 | 7/1999 |
| WO | WO-99/57151 A2 | 11/1999 |
| WO | WO-00/56772 A1 | 9/2000 |
| WO | WO-00/67789 A1 | 11/2000 |
| WO | WO-02/11695 A2 | 2/2002 |
| WO | WO-02/12500 A2 | 2/2002 |
| WO | WO-02/13860 A1 | 2/2002 |
| WO | WO-02/30463 A2 | 4/2002 |
| WO | WO-02/43695 A2 | 6/2002 |
| WO | WO-02/43750 A2 | 6/2002 |
| WO | WO-02/051979 A2 | 7/2002 |
| WO | WO-02/072636 A2 | 9/2002 |
| WO | WO-02/096457 A2 | 12/2002 |
| WO | WO-03/053471 A1 | 7/2003 |
| WO | WO-2004/001007 A2 | 12/2003 |
| WO | WO-2004/009776 A2 | 1/2004 |
| WO | WO-2004/016286 A2 | 2/2004 |
| WO | WO-2004/024752 A1 | 3/2004 |
| WO | WO-2004/050059 A1 | 6/2004 |
| WO | WO-2004/055164 A2 | 7/2004 |
| WO | WO-2004/060343 A1 | 7/2004 |
| WO | WO-2004/066957 A2 | 8/2004 |
| WO | WO-2004/102184 A1 | 11/2004 |
| WO | WO-2005/102284 A1 | 11/2005 |
| WO | WO-2005121177 A2 | 12/2005 |
| WO | WO-2006012500 A9 | 2/2006 |
| WO | WO-2006/031560 A2 | 3/2006 |
| WO | WO-2006069036 A2 | 6/2006 |
| WO | WO-2006/138181 A2 | 12/2006 |
| WO | WO-2007/003936 A1 | 1/2007 |
| WO | WO-2007005608 A2 | 1/2007 |
| WO | WO 2007/014162 A2 | 2/2007 |
| WO | WO-2007/074880 A1 | 7/2007 |
| WO | WO-2007/095337 A2 | 8/2007 |
| WO | WO-2008/015419 A2 | 2/2008 |
| WO | WO 2008/046033 A2 | 4/2008 |
| WO | WO-2008/121301 A1 | 10/2008 |
| WO | WO-2009/020654 A1 | 2/2009 |

OTHER PUBLICATIONS

Barrie et al. "The interleukin-12 family of cytokines: Therapeutic targets for inflammatory disease mediation." Clinical and Applied Immun. Rev. 2005 5(4): 225-240.

Berrebi, D., et al. "Interleukin-12 expression is focally enhanced in the gastric mucosa of pediatric patients with Crohn's disease." Am J Pathol. Mar. 1998; 152(3):667-72.

Bird, R.E., et al. "Single-chain antigen-binding proteins." Science. Oct. 21, 1988; 242(4877):423-426.

Brown, Jr., P.S., et al. "Anti-Tac-H, a humanized antibody to the interleukin 2 receptor prolongs primate cardiac allograft survival." Proc Natl Acad Sci USA. Apr. 1, 1991; 88(7):2663-7.

Bucht, A, et al. "Expression of interferon-gamma (IFN-gamma), IL-10, IL-12 and transforming growth factor-beta (TGF-beta) mRNA in synovial fluid cells from patients in the early and late phases of rheumatoid arthritis (RA)." Clin Exp Immunol. Mar. 1996 103(3) :357-67.

Cambridge Antibody Technology Group pic, "Applying technology to target disease," Annual Report (1998).

Cambridge Antibody Technology, "Clinical Trials From CAT," PR Newswire(1999).

Carter, R.W., et al. Production and characterization of monoclonal antibodies to human interleukin-12. Hybridoma. 1997. 16(4):363-9.

Casset et al. "A peptide mimetic of an anti-CD4 monoclonal antibody by rational design." Biochem and Biophys Res Comm. 2003 307:198-205.

Chizzonite, R. et al., "IL-12: Monoclonal antibodies specific to the 40-kDa subunit block receptor binding and biological activity on activated human lymphoblasts," J. Immunol., 1991, vol. 147:1548-1556.

Clackson, T., et al. "Making antibody fragments using phage display libraries." Nature. Aug. 15, 1991; 352(6336):624-28.

(56) References Cited

OTHER PUBLICATIONS

Clark, Steven C., "Interleukin 12: Molecular, Biological and Clinical Perspectives," Molecular Biology of Haematopoeiesis, (1993) vol. 3:3-14.
Cordoba et al. "Non-enzymatic hinge region fragmentation of antibodies in solution" J Chromatogr B 2005 818:115-121.
Dall'AcQua, W., et al. "Antibody engineering." Curr Opin Struct Biol. 1998; 8(4):443-50.
D'Andrea, A. et al., "Production of Natural Killer Cell Stimulatory Factor (Interleukin 12) by Peripheral Blood Mononuclear cells," J. Exp. Med., 1992, vol. 176:1387-1398.
Daugherty et al. "Antibody affinity maturation using bacterial surface display." Protein Eng. 1998 11(9):825-832.
Ding, et al. "ABT-874, a fully human monoclonal anti-IL-12/IL-23 antibody for the potential treatment of autoimmune diseases." Current Opinion in Investigational Drugs 2008 9(5):515-522.
Duchmann, R., et al. "Tolerance towards resident intestinal flora in mice is abrogated in experimental colitis and restored by treatment with interleukin-10 or antibodies to interleukin 12." Eur. J. Immunol. 1996, 26:934-8.
Fais, S., et al. "Interferon expression in Crohn's disease patients: increased interferon-gamma and -alpha mRNA in the intestinal lamina propria mononuclear cells." J Interferon Res. 1994; Oct. 14(5):235-8.
Fauchet et al. "Characterization of Monoclonal Antibodies against Human Interleukin-12 and Their Use in an Elisa for the Measurement of This Cytokine." Annals of the New York Academy of Sciences. 1996 vol. 795, pp. 334-336.
Fehr et al. "Nucleotide and Predicted Peptide Sequence of Feline Interleukin-12 (IL-12)."DNA sequence 1997 8:77-82.
Fuchs, P., et al. "Targeting recombinant antibodies to the surface of *Escherichia coli*: fusion to a peptidoglycan associated lipoprotein." Biotechnology (NY). Dec. 1991; 9(12):1369-72.
Fuss, I.J., et al. "Disparate CD4+ lamina propria (LP) lymphokine secretion profiles in inflammatory bowel disease, Crohn's disease LP cells manifest increased secretion of IFN gamma whereas ulcerative colitis LP cells manifest increased secretion of IL-5." J Immunol. Aug. 1, 1996; 157(3):1261-1270.
Garrard, L.J., et al. "Fab assembly and enrichment in a monovalent phage display system," Biotechnoloοy (NY), Dec. 1991; vol. 12:1373-7.
Gately, M.K., et al. "The interleukin-12/interleukin-12-receptor system: role in normal and pathologic immune responses." Annu Rev Immunol. 1998; 16:495-521.
Gram, H., et al. "In vitro selection and affinity maturation of antibodies from a naïve combinatorial immunoglobulin library." Proc Natl Acad Sci USA. Apr. 15, 1992; 89(8):3576-80.
Griffiths, A.D., et al. "Human anti-self antibodies with high specificity from phage display libraries." EMBO J. Feb. 1993; 12(2):725-34.
Hamid, Q., et al. "In vivo expression of IL-12 and IL-13 in atopic dermatitis." J Allergy Clin Immunol. Jul. 1996 ; 98(1 ):225-31.
Hanes, J., et al. "In vitro selection and evolution of functional proteins by using ribosome display." Proc Natl Acad Sci USA. May 13, 1997; 94(10):4937-42.
Hawkins, R.E., et al. "Selection of phage antibodies by binding affinity. Mimicking affinity maturation." J Mol Bioi. Aug. 5, 1992; 226(3):889-96.
Hay, B.N., et al. "Bacteriophage cloning and *Escherichia coli* expression of a human IgM Fab." Hum Antibodies Hybridomas. Apr. 1992; 3(2) :81-5.
He, M., et al. "Antibody-ribosome-mRNA (ARM) complexes as efficient selection particles for in vitro display and evolution of antibody combining sites." Nucleic Acids Res. Dec. 15, 1997; 25(24):5132-4.
Heinzel et al. "Interleukin 12 is Produced In Vivo during Endotoxemia and Stimulates Synthesis of Gamma Interferon." Infection and Immunity 1994 62(10):4244-4249.
Hoogenboom, H.R., et al. "Multi-subunit proteins on the surface of filamentous phage:methodologies for displaying antibody (Fab) heavy and light chains." Nucleic Acids Res. Aug. 11, 1991; 19(15):4133-7.
Hoogenboom, Hennie R. et al., "Antibody phage display technology and its applications," Immunotechnology, 1998, 4:1-20.
Hoogenboom, Hennie R., "Designing and optimizing library selection strategies for generating high-affinity antibodies," Trends Biotechnol. 1997, 15(2):62-70.
http://www.bdbiosciences.com "Purified mouse anti-human IL-12, p40/p70 monoclonal antibody, clone C8.6." 2005 BD Pharmingen Technical Data Sheet for product #554659.
http://www.biolegend.com "LEAF Purified anti-human IL-12/IL-23, p40 (monomer, dimer, heterodimer), clone 11.5." May 1, 2007 Technical Data Sheet for product #501812.
http://www.clinicaltrials.gov "A Safety and Efficacy Study of CNTO 1275 in Patients with Multiple Sclerosis" 2009 ClinicalTrials.gov Identifier: NCT00207727; (Jul. 14, 2009).
http://www.clinicaltrials.gov "A Study of the Safety and Efficacy of CNTO 1275 in Patients with Active Psoriatic Arthritis." 2009 ClinicalTrials.gov Identifier: NCT00267956; (Jul. 14, 2009).
http://www.clinicaltrials.gov "A Study of the Safety and Efficacy of CNTO 1275 in Patients with Severe Plaque-Type Psoriasis" 2009 ClinicalTrials.gov Identifier: NCT00267969; (Jul. 14, 2009).
http://www.clinicaltrials.gov "A Study of the Safety and Efficacy of CNTO 1275 in Subjects with Severe Plaque-Type Psoriasis." 2009 ClinicalTrials.gov Identifier: NCT00320216; (Jul. 14, 2009).
http://www.clinicaltrials.gov "Efficacy and Safety of ABT-874 in Subjects With Moderate to Severe Chronic Plaque Psoriasis." 2009 ClinicalTrials.gov Identifier: NCT00292396; (Jul. 14, 2009).
http://www.clinicaltrials.gov "Monoclonal Antibody Treatment of Crohn's Disease" 2009 ClinicalTrials.gov Identifier: NCT00007163; (Jul. 14, 2009).
http://www.clinicaltrials.gov "Safety and Effectiveness of Two Doses of ABT-874 as Compared to Placebo in Subjects with Multiple Sclerosis." (MS) 2009 ClinicalTrials.gov Identifier: NCT00086671; (Jul. 14, 2009).
http://www.clinicaltrials.gov; "A Study of the Safety and Efficacy of CNTO 1275 in Subjects with Moderate to Severe Psoriasis", ClinicalTrials.gov Identifier: NCT00307437; (Jul. 14, 2009).
Huse, W.D., et al. "Generation of a large combinatorial library of the immunoglobulin repertoire in phage lambda." Science. Dec. 8, 1989; 246(4935):1275-81.
Huston, J.S., et al. "Protein engineering of antibody binding sites: recovery of specific activity in an anti-digoxin single-chain Fv analogue produced in *Escherichia coli*." Proc Natl Acad Sci USA. Aug. 1988; 85(16):5879-83.
International Search Report for Application No. PCT/US0007946, dated Aug. 23, 2000.
International Search Report for Application No. PCT/US07/026212 dated Jul. 11, 2008.
International Search Report for Application No. PCT/US08/00564, dated Aug. 8, 2008.
International Search Report for Application No. PCT/US09/036765, dated Jan. 22, 2010.
International Search Report for Application No. PCT/US09/65714, dated Mar. 25, 2010.
Irving, R.A., et al. "Affinity maturation of recombinant antibodies using *E. coli* mutator cells." Immunotechnology. Jun. 1996; 2(2):127-43.
Jackson J.R., et al. "In vitro antibody maturation. Improvement of a high affinity, neutralizing antibody against IL-1 beta." J Immunol. 1995; 154(7):3310-9.
Junghans, R.P., et al. "Anti-Tac-H, a humanized antibody to the interleukin 2 receptor with new features for immunotherapy in malignant and immune disorders." Cancer Res. Mar. 1, 1990; 50(5):1495-502.
Kabat, E.A., et al. "Attempts to locate complementarity-determining residues in the variable positions of light and heavy chains." Ann NY Acad Sci. Dec. 31, 1971; 190:382-93.
Kabat, E.A., et al. Accession No. PB91-192898, Sequences of Proteins of Immunological Interest, Fifth Edition, U.S. Department of Health and Human Services, NIH Publication No. 91-3242,1991.

(56) References Cited

OTHER PUBLICATIONS

Kasper et al., "A phase I trial of an interleukin-12/23 monoclonal antibody in relapsing multiple sclerosis" Current Medical Research and Opinion, 2006 22(9):1671-1678.

Kauffman, et al. "A Phase I Study Evaluating the Safety, Pharmacokinetics, and Clinical Response of a Human IL-12 p40 Antibody in Subjects with Plaque Psoriasis" J. Invest. Dermatology, 2004 vol. 123:1037-1044.

Kettleborough, C.A., et al. "Humanization of a mouse monoclonal antibody by CDR-grafting: the importance of framework residues on loop conformation." Protein Eng. 1991, 4:773-83.

Kimball, et al. "Safety and Efficacy of ABT-874, a Fully Human Interleukin 12/23 Monoclonal Antibody, in the Treatment of Moderate to Severe Chronic Plaque Psoriasis" 2008 ARCH Dermatol, 144(2):200-207.

Kobayashi, M., et al. "Identification and purification of natural killer cell stimulatory factor (NKSF), a cytokine with multiple biologic effects on human lymphocytes." J Exp Med. Sep. 1, 1989;170(3):827-45.

Leonard et al. "Prevention of Experimental Autoimmune Encephalomyelitis by Antibodies Against Interleukin 12" J. Exp. Med. 1995 181:381-386.

Ling, P., et ai. "Human IL-12 p40 homodimer binds to the Il-12 receptor but does not mediate biologic activity." J Immunol. Jan. 1, 1995; 154(1):116-27.

Liu et al. "Analysis of the Interrelationship between IL-12, TNF-alpha, and IFN-gamma Production during Murine Listeriosis" Cellular Immunology 1995 163(2):260-267.

Longbreak, E. E., et al. "Why did IL-12/1L-23 antibody therapy fail in multiple sclerosis?" Expert Rev. Neurother., 2009, vol. 9, No. 3, p. 319-321.

Mannon et al., "Anti-Interleukin-12 Antibody for Active Crohn's Disease" New England J. Med. 2004 351 :2069-2079.

McCafferty, J., et al. "Phage antibodies: filamentous phage displaying antibody variable domains." Nature. Dec. 6, 1990; 348(6301):552-4.

Meager et al. "Spontaneous Neutralising Antibodies to Interferon-alpha and Interleukin-12 in Thymoma-Associated Autoimmune Disease" Lancet 1997; 909:1596-1597.

Medical News Today, Press release. Abbott's ABT 874 Shows Positive Results for Maintenance of Response in Phase II Psoriasis Study. (created Oct. 2, 2007) Retrieved from internet Dec. 17, 2009 http://www.medicalnewstoday.com/printerfriendlynews.php?news.php?newsid=84202.

Monteleone, G., et al. "Interleukin 12 is expressed and actively released by Crohn's disease intestinal lamina propria mononuclear cells." Gastroenterology. Apr. 1997; 112(4):1169-78.

Morita, Y., et al. "Expression of interleukin-12 in synovial tissue from patients with rheumatoid arthritis." Arthritis Rheum. Feb. 1998; 41(2):306-14.

Neri et al. Targeting by affinity-matured recombinant antibody fragments of an angiogenesis associated fibronectin isoform. Nature Biotechnology 1997 15(12) 1271-1275.

Neurath, M.F., et al. "Antibodies to interleukin 12 abrogate established experimental colitis in mice." J Exp Med. Nov. 1, 1995; 182(5):1281-90.

Oppmann, B. et al., "Novel p19 Protein Engages IL-12p40 to form a cytokine, IL-23, with biological activities similar as well as distinct from IL-12," Immunity, 2000, vol. 13:715-725.

Oswald et al. "Interleukin-12 Synthesis Is a Required Step in Trehalose Dimycolate-Induced Activation of Mouse Peritoneal Macrophages." Infection and Immunity 1997 65(4):1364-1369.

Panaccione et al. "Briakinumab (Anti-interleukin 12/23p40, ABT874) for Treatment of Crohn's Disease (CD)" 2010 abstract of submission to American College of Gastroenterology Annual Scientific Meeting.

Paper 128 of Patent Interference 105,592 McK, Technology Center 1600, *Centocor, Inc.*, vs. *Abbott GmbH &Co. KG* entered Jul. 1, 2008.

Paper 20 of Patent Interference 105,592 McK, Technology Center 1600, *Centocor, Inc.*, vs. *Abbott GmbH &Co. KG* entered Feb. 5, 2008.

Parronchi, P., et al. "Type 1 T-helper cell predominance and interleukin-12 expression in the gut of patients with Crohn's disease." Am J Pathol. Mar. 1997; 150(3):823-32.

Paul 1993 Fundamental Immunology 3rd Ed., 1993 292-295.

Pini, A., et al. "Design and use of a phage display library. Human antibodies with subnanomolar affinity against a marker of angiogenesis eluted from a two-dimensional gel." J Biol Chem. Aug. 21, 1998; 273(34):21769-76.

Pini, A., et al. "Hierarchical affinity maturation of a phage library derived antibody for the selective removal of cytomegalovirus from plasma." J Immunol Methods. Aug. 7, 1997; 206(1-2):171-82.

Podlaski, F.J., et al. "Molecular characterization of interleukin 12." Arch Biochem Biophys. Apr. 1992; 294(1):230-7.

Riechmann, Lutz et al., "Phage Display and Selection of a Site-Directed Randomized Single-Chain Antibody Fv Fragment for Its Affinity Improvement," Biochemistry, 1993, vol. 32:8848-8855.

Ryan, C. et al. "The use of ustekinumab in autoimmune disease." Expert Opin. Biol. Ther., 2010, vol. 10, No. 4, p. 587-604.

Scherl, E.J., et al. "Review of the safety and efficacy of ustekinumab." Ther. Adv. Gastroenterol., 2010, vol. 3, No. 5, p. 321-328.

Schwaller et al. "Interleukin-12 Expression in Human Lymphomas and Nonneoplastic Lymphoid Disorders," Blood, 1995, 85(8): 2182-2188.

Seder, A.A., et al. "Interleukin 12 acts directly on CD4+ T cells to enhance priming for interferon gamma production and diminishes interleukin 4 inhibition of such priming." Proc Natl Acad Sci USA. Nov. 1, 1993; 90(21):10188-92.

Segal, B.M. et al. Repeated subcutaneous injections of IL12/23 p40 neutralising antibody, ustekinumab, in patients with relapsing-remitting multiple sclerosis: a phase II, double-blind, placebo-controlled, randomized, dose ranging study. Lancet Neurol., 2008, vol. 7, p. 796-804.

Sharon, J. "Structural correlates of high antibody affinity: three engineered amino acid substitutions can increase the affinity of an anti-p-azophenylarsonate antibody 200-fold." Proc Natl Acad Sci USA. Jun. 1990; 87(12):4814-7.

Short et al. "Contribution of Antibody Heavy Chain CDR1 to Digoxin Binding Analyzed by Random Mutagenesis of Phage-displayed Fab 26-10*," J. Biol. Chem. 1995 270(48):28541-28550.

Smith et al. "Specific cleavage of immunoglobulin G by copper ions." Int J Peptide Protein Res. 1996 48:48-55.

Supplemental European Search Report for European Application No. EP08742311, Feb. 26, 2010.

Tao, W. et al., "P19ARF Stabilizes p53 by Blocking Nucleo-cytoplasmic shuttling of Mdm2," Proc. Natl. Acad. Sci. USA., 1999, vol. 96:6937-6941.

Taylor, L.D., et al. "A transgenic mouse that expresses a diversity of human sequence heavy and light chain immunoqlobulins." Nucleic Acids Res. Dec. 11, 1992; 20(23):6287-95.

Toichi et al., "An anti-IL-12p40 antibody down-regulates type 1 cytokines, chemokines, and IL-12/IL-23 in psoriasis." J Immunol. 2006 177:4917-4926.

Tomlinson, Ian M. et al., "The Imprint of Somatic Hypermutation on the Repertoire of Human Germline V Genes," J. Mol. Biol., 1996 vol. 256:813-817.

Trinchieri, Giorgio, "Interleukin-12 and its role in the generation of TH1 cells," Immunology Today, (1993) vol. 14(7):335-338.

Turka, L.A., et al. "Interleukin 12: a potential link between nerve cells and the immune response in inflammatory disorders." Mol Med. Sep. 1995; 1(6):690-9.

United States Patent and Trademark Office, "Patent Interference No. 105,592," Centocor Motion 1 (2007).

United States Patent and Trademark Office, "Patent Interference No. 105,592," Declaration (2007).

Valiante, Nicholas M. et al., "Role of the Production of Natural Killer Cell Stimulatory Factor (NKSF/IL-12) in the Ability of B Cell Lines to Stimulate T and NK Cell Proliferation," Cellular Immunology, (1992) vol. 145:187-198.

(56) References Cited

OTHER PUBLICATIONS

Vaughan et al., "Human Antibodies with Sub-nanomolar Affinities Isolated from a Large Non-immunized Phage Display Library" Nature Biotechnology, 1996 14:309-314.

Vollmer et al. "A Phase 2, 24-Week, Randomized, Placebo-Controlled, Double-Blind Study Examining the Efficacy and Safety of an Anti-Interleukin-12 and -23 Monoclonal Antibody in Patients With Relapsing-Remitting or Secondary-Progressive Multiple Sclerosis." 2010, manuscript submission to Multiple Sclerosis; Mult Soler. Dec. 6, 2010. [Epub ahead of print].

Wilkinson et al. "Characterization of anti-mouse IL-12 monoclonal antibodies and measurement of mouse IL-12 by ELISA ." J. Immun. Methods 1996 189(1): 15-24.

Williamson et al. "Neutralizing IL-12 During Induction of Murine Acute Graft-Versus-Host Disease Polarizes the Cytokine Profile Toward a Th2-Type Alloimmune Response and Confers Long Term Protection From Disease." J. Immun. 1997 159:1208-1215.

Windhagen, A., et al. "Expression of costimulatory molecules B7-1 (COSO), B7-2 (CD86), and interleukin 12 cvtokine in multiple sclerosis lesions." J Exp Med. Dec. 1, 1995; 182(6):1985-96.

Winter, G., et al. "Making antibodies by phage display technology." Annu Rev Immunol. 1994; 12:433.55.

Wolf, S.F. et al., "Cloning of cDNA for Natural Killer Cell Stimulatory Factor, A Heterodimeric Cytokine with Multiple Biologic Effects on T and Natural Killer Cells," J. Immunol. 1991, 146:3074-3081.

Wu et al., "Simultaneous targeting of multiple disease mediators by a dual-variable-domain immunoglobulin," Nature Biotechnology 2007 25(11): 1290-1297.

Yago, T., et al. "IL-23 induces human osteoclastogenesis via IL-17 in vitro, and anti-IL-23 antibody attenuates collagen-induced arthritis in rats." Arthritis Research & Therapy, 2007, vol. 9, R96.

Yawalkar et al. "Expression of Interleukin-12 is Increased in Psoriatic Skin," Journal of Investigative Dermatology 1998 vol. 111, pp. 1053-1057.

Klyushnichenko, V., "Protein Crystallization: From HTS to Kilogram Scale," Curr. Opin. In Drug Discovery & Development, 6(6): 848-854, 2003.

Zhao et al., "Recent U.S. Patents on Protein Drug Formulation: 2000-2007," Recent Patents on Drug Delivery and Formulation, 2(3):200-208(9) (2008).

Daugherty et al., "Formulation and delivery issues for monoclonal antibody therapeutics, " Advanced Drug Delivery Reviews, 58:686-706 (2006).

International Search Report for Application No. PCT/EP09/050385, dated May 12, 2009.

International Preliminary Report on Patentability for Application PCT/EP09/050385, dated Dec. 21, 2009.

Merienne et al., "The Functional Architecture of an Acetylcholine Receptor-mimicking Antibody," Sep. 1997, The Journal of Biological Chemistry, 272: 23775-23783.

Parhami-Seren et al., "Contribution of heavy chain junctional amino acid diversity to antibody affinity among p-azophenylarsonate-specific antibodies," The Journal of Immunology, Sep. 1996, 157(5): 2066-2072.

Chames et al., "Improving the Affinity and the Fine Specificity of an Anti-Cortisol Antibody by Parsimonious Mutagenesis and Phage Display," J Immunol, (1998) 161: pp. 5421-5429.

Deng et al. "Basis for selection of improved carbohydrate-binding single-chain antibodies from synthetic gene libraries" PNAS (1995) 92: 4992-4996.

Kosako et al., "Isolation and characterization of neutralizing single-chain antibodies against Xenopus mitogen-activated protein kinase kinase from phage display libraries" Biochemistry (1996) 35:13212-21.

Liu et al. "Reversible Self-Association Increases the viscosity of a Concentrated Monoclonal Anitbody in Aqueous Solution", J Pharma Sci ,vol. 94, No. 9, pp. 1928-1940 (2005).

Wang et al. "Opalescence of an IgG1 Monoclonal Antibody Formulation is Mediated by Ionic Strength and Excipients", BioPharm Internatl, vol. 22(4) (2009).

Li et al., "Resurrecting Abandoned Proteins with Pure Water: CD and NMR Studies of Protein Fragments Solubilized in Salt-Free Water," Biophys J 91:4201-4209 (2006).

Manning et al., "Stability of Protein Pharmaceuticals," Pharm Res 6:903-918 (1989).

Shire et al., "Challenges in the Development of High Protein Concentration Formulations," J Pharm Sci 93:1390-1402 (2004).

Tian et al., "Spectroscopic evaluation of the stabilization of humanized monoclonal antibodies in amino acid formulations," Intl J Pharm 355:20-31(2007).

Ahamed et al. "Phase Behaviour of Intact Monoclonal Antibody," Biochemical Journal, Jul. 2007, vol. 93, pp. 610-619.

Baldock, "A comparison of microbatch and vapour diffusion for initial screening of crystallization conditions," Journal of Crystal Growth, Oct. 1996, vol. 168, No. 1-4, pp. 170-174.

Connell, G. E., et al., "A Human IgG Myeloma Protein Crystallizing with Rhombohedral Symmetry," Can. J. Biochem., 1973, vol. 51, pp. 1137-1141.

Data Sheet: Drum Rollers—Portable Drum Rotators Drum Mixers, URL<:http://web.archive.org/web/20070117013405/http://www.morsemfgeo.com/products/201-Portable-Drum-Roller.htm>., Jan. 2007 [retrieved on Dec. 2, 2008].

Data Sheet: Fisher Scientific. Hematology/Chemistry Mixer Fisher Scientific, http://www.fishersci.com/, 2008 [Retrieved on Dec. 2, 2008].

Harris, L. J., et al., "The Three-dimensional Structure of an Intact Monoclonal Antibody for Canine Lymphoma," Nature, 1992, vol. 360, pp. 369-372.

Huber, R., et al., "Crystallographic Structure Studies of an IgG Molecule and an Fc Fragment," Nature, 1976, vol. 264, pp. 415-420.

International Search Report for Application No. PCT/US09/000568, dated May 13, 2009.

International Search Report for Application No. PCT/US08/009549, dated Dec. 17, 2008.

International Search Report for Application No. PCT/US07/022622, dated Sep. 4, 2008.

Jen et al., "Diamonds in the Rough: Protein Crytsals from a Formulation Perspective," Pharmaceutical Research, 2001, vol. 18, No. 11, pp. 1483-1488.

Jentoft, J. E., et al., "Characterization of a Human Cryoglobulin Complex: A Crystalline Adduct of a Monoclonal Immunoglobulin G and Albumin," Biochemistry, 1982, vol. 21, pp. 289-294.

Jones, H. B., "On a New Substance Occurring in the Urine of a Patient with Mollities Ossium," Phil. Tr. Royal Soc. London, 1848, vol. 138, pp. 55-62.

Mills, L. E., et al., "Crystallocryoglobulinemia Resulting from Human Monoclonal Antibodies to Albumin," Annals of Internal Medicine, 1983, vol. 99, pp. 601-604.

Nisonoff, A., et al. "Properties of Crystallized Rabbit Anti-p-Azobenzoate Antibody," Cold Spring Harb. Symp. Quant. Biol., 1967, vol. 32, pp. 89-93.

Putnam, F. W., "Abnormal Human Serum Globulins," 1955, Science, vol. 122, pp. 275-277.

Rajan, S. S., et al., "Three-Dimensional Structure of the Mcg IgG1 Immunoglobulin," 1983, Molecular Immunology, vol. 20, pp. 787-799.

Sarma, V. R., et al., "The Three-Dimensional Structure at 6 A Resolution of a Human γG1 Immunoglobulin Molecule," The Journal of Biological Chemistry, 1971, vol. 246, pp. 3753-3759.

Terry, W. D., et al., "Crystallographic Studies of a Human Immunoglobulin," Nature, 1968, vol. 220, pp. 239-241.

Von Bonsdorff, B., et al., "On the Presence of a High-molecular Crystallizable Protein in Blood Serum in Myeloma," Folia Haemat., 1938, vol. 59:, p. 184-208.

Yang et al., "Crystalline Monoclonal Antibodies for Subcutaneous Delivery," Proceedings of the National Academy of Sciences Jun. 10, 2003. vol. 100, No. 12, pp. 6934-6939.

McPherson, "A comparison of salts for the crystallization of macromolecules," Protein Science, vol. 10:418-422, 2001.

(56) References Cited

OTHER PUBLICATIONS

Baldock, "A comparison of microbatch and vapour diffusion for initial screening of crystallization conditions", *Journal of Crystal Growth*, vol. 168:170-174, 1996; Abstract only.

International Search Report and Written Opinion for Application No. PCT/US08/04006, dated Jul. 2, 2008.

International Preliminary Report on Patentability for Application No. PCT/US08/04006, dated Aug. 28, 2009.

Kundrot, C.E. Which Strategy for a Protein Crystallization Project? Molecular Life Science, 2004. vol. 61, pp. 525-536.

Benevenuti et al., Crystallization of Soluble Proteins in Vapor Diffusion for X-ray Crystallography, Nature Protocols, published on-line Jun. 28, 2007, 2(7): 1633-1651.

Cudney R. Protein Crystallization and Dumb Luck. The Rigaku Journal. 1999. vol. 16, No. 1, pp. 1-7.

Drenth, "Principles of Protein X-Ray Crystallography", $2^{nd}$ Edition, 1999 Springer-Verlag New York Inc., Chapter 1, p. 1-21.

Weber, P.C. Overview of Crystallization Methods. Methods in Enzymology. 1997. vol. 276, pp. 13-22.

\* cited by examiner

|.....................450 µm.....................|

|.....................225 µm.....................|

|..........................450 μm...........................|

|..........................450 μm...........................|

SEQUENCE LISTING

```
<160> NUMBER OF SEQ ID NOS: 2

<210> SEQ ID NO 1
<211> LENGTH: 444
<212> TYPE: PRT
<213> ORGANISM: Homo sapiens

<400> SEQUENCE: 1

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30
```

```
Gly Met His Trp Val Arg Gln Ala Pro Gly Lys Gly Leu Glu Trp Val
         35                  40                  45
Ala Phe Ile Arg Tyr Asp Gly Ser Asn Lys Tyr Tyr Ala Asp Ser Val
 50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Lys Thr His Gly Ser His Asp Asn Trp Gly Gln Gly Thr Met Val Thr
                100                 105                 110
Val Ser Ser Ala Ser Thr Lys Gly Pro Ser Val Phe Pro Leu Ala Pro
            115                 120                 125
Ser Ser Lys Ser Thr Ser Gly Gly Thr Ala Ala Leu Gly Cys Leu Val
    130                 135                 140
Lys Asp Tyr Phe Pro Glu Pro Val Thr Val Ser Trp Asn Ser Gly Ala
145                 150                 155                 160
Leu Thr Ser Gly Val His Thr Phe Pro Ala Val Leu Gln Ser Ser Gly
                165                 170                 175
Leu Tyr Ser Leu Ser Ser Val Val Thr Val Pro Ser Ser Ser Leu Gly
            180                 185                 190
Thr Gln Thr Tyr Ile Cys Asn Val Asn His Lys Pro Ser Asn Thr Lys
    195                 200                 205
Val Asp Lys Lys Val Glu Pro Lys Ser Cys Asp Lys Thr His Thr Cys
        210                 215                 220
Pro Pro Cys Pro Ala Pro Glu Leu Leu Gly Gly Pro Ser Val Phe Leu
225                 230                 235                 240
Phe Pro Pro Lys Pro Lys Asp Thr Leu Met Ile Ser Arg Thr Pro Glu
                245                 250                 255
Val Thr Cys Val Val Val Asp Val Ser His Glu Asp Pro Glu Val Lys
            260                 265                 270
Phe Asn Trp Tyr Val Asp Gly Val Glu Val His Asn Ala Lys Thr Lys
    275                 280                 285
Pro Arg Glu Glu Gln Tyr Asn Ser Thr Tyr Arg Val Val Ser Val Leu
290                 295                 300
Thr Val Leu His Gln Asp Trp Leu Asn Gly Lys Glu Tyr Lys Cys Lys
305                 310                 315                 320
Val Ser Asn Lys Ala Leu Pro Ala Pro Ile Glu Lys Thr Ile Ser Lys
                325                 330                 335
Ala Lys Gly Gln Pro Arg Glu Pro Gln Val Tyr Thr Leu Pro Pro Ser
            340                 345                 350
Arg Glu Glu Met Thr Lys Asn Gln Val Ser Leu Thr Cys Leu Val Lys
    355                 360                 365
Gly Phe Tyr Pro Ser Asp Ile Ala Val Glu Trp Glu Ser Asn Gly Gln
370                 375                 380
Pro Glu Asn Asn Tyr Lys Thr Thr Pro Pro Val Leu Asp Ser Asp Gly
385                 390                 395                 400
Ser Phe Phe Leu Tyr Ser Lys Leu Thr Val Asp Lys Ser Arg Trp Gln
                405                 410                 415
Gln Gly Asn Val Phe Ser Cys Ser Val Met His Glu Ala Leu His Asn
            420                 425                 430
His Tyr Thr Gln Lys Ser Leu Ser Leu Ser Pro Gly
    435                 440
```

```
<210> SEQ ID NO 2
<211> LENGTH: 217
<212> TYPE: PRT
<213> ORGANISM: Homo sapiens

<400> SEQUENCE: 2

Gln Ser Val Leu Thr Gln Pro Pro Ser Val Ser Gly Ala Pro Gly Gln
1               5                   10                  15

Arg Val Thr Ile Ser Cys Ser Gly Ser Arg Ser Asn Ile Gly Ser Asn
            20                  25                  30

Thr Val Lys Trp Tyr Gln Gln Leu Pro Gly Thr Ala Pro Lys Leu Leu
        35                  40                  45

Ile Tyr Tyr Asn Asp Gln Arg Pro Ser Gly Val Pro Asp Arg Phe Ser
50                  55                  60

Gly Ser Lys Ser Gly Thr Ser Ala Ser Leu Ala Ile Thr Gly Leu Gln
65                  70                  75                  80

Ala Glu Asp Glu Ala Asp Tyr Tyr Cys Gln Ser Tyr Asp Arg Tyr Thr
                85                  90                  95

His Pro Ala Leu Leu Phe Gly Thr Gly Thr Lys Val Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215
```

CRYSTALLINE ANTI-HUMAN IL-12 ANTIBODIES

CROSS REFERENCE TO RELATED APPLICATIONS

This application claims priority to U.S. Provisional Application Ser. No. 60/920,608, filed on Mar. 29, 2007, which is incorporated by reference in its entirety.

FIELD OF THE INVENTION

The present invention relates to a batch crystallization method for crystallizing an antibody, which allows the production of the antibody on an industrial scale; crystals of antibodies, in particular as obtained according to the disclosed method; and compositions containing the crystals as well as methods of use of the crystals and compositions.

BACKGROUND OF THE INVENTION a) Antibody Crystals

With over 100 monoclonal antibodies (mAbs) currently being evaluated in clinical study phases 2 or 3, the mAb market is considered one of the most promising biopharmaceutical markets. Since these drugs are delivered in single doses often exceeding 100 mg, there is an urgent need to find suitable formulation strategies that satisfy stability, safety, and patient compliance. However, highly concentrated liquid mAb formulations show increased viscosity, hindering syringeability through patient friendly thin needles. Furthermore, the tendency for mAb molecules to aggregate at such high concentrations exponentially increases when compared to moderately concentrated solutions. This is unacceptable, with regard to safety and stability requirements.

Thus, the delivery of high mAb doses is reserved for large volumes, which generally have to be delivered via infusion. This way of dosing is cost intensive and significantly reduces the patient's compliance.

Therefore, pharmaceutically applicable low volume mAb crystal suspensions for subcutaneous injection would be highly desirable. Theoretically, degradation pathways influencing the mAb integrity should be significantly decelerated due to the rigidity of a crystal lattice, where motions in the protein structure are hindered. Moreover, an increase in viscosity would be significantly reduced when comparing highly concentrated crystal suspensions with liquid formulations. With respect to sustained release, it might be possible to generate or alter protein crystals such that they dissolve slowly when brought into a patient's body. This would be a very elegant way to deliver a sustained release formulation, as the extensive use of excipients and processes harming the mAb structure would be prevented.

Despite the great potential in using protein crystals as a drug substance, few attempts have been made to systematically evaluate this strategy.

A well-known exemption is insulin, which was successfully crystallized decades ago. Today, the use of crystal suspensions of insulin is well described, offering stable and long acting formulations being well established on the market. The discrepancy between the development of insulin crystals and crystallization of all other proteins might be related to the fact that ordered insulin aggregates are natively formed in the pancreas. Thus, insulin crystals are easily obtained when insulin is brought in contact with an excess of zinc ions. Most other proteins tend to form unordered precipitates rather than crystals, and therefore, finding crystallization conditions for a protein is a time consuming, non-trivial task.

Despite a great interest in harvesting protein crystals for x-ray diffraction analysis, finding suitable crystallization conditions still is an empirical science, as in principle any protein behaves differently. To date, no general rule has been found that might reliably predict a successful crystallization condition for a protein of choice. Thus, obtaining crystals of a given protein always is referred to as the "bottle neck" of whatever intended application is planned later on.

Antibodies are especially hard to crystallize, due to the flexibility of the molecule. Nevertheless, examples of immunoglobulin crystals have been known for a long time. The first example of immunoglobulin crystals were described 150 years ago by an English physician, Henry Bence Jones; he isolated crystals of an abnormal Ig light chain dimer from the urine of a myeloma patient (Jones, H. B. (1848) Philosophical Transactions of the Royal Society, London 138: 55-62). Such abnormal Igs have been known ever since as Bence Jones proteins. In 1938, the spontaneous crystallization of a distinct abnormal Ig from the serum of a myeloma patient was described (von Bonsdorf, B. et al. (1938) Folia Haematologia 59: 184-208), apparently an Ig heavy chain oligomer (MW 200 kDa).

Crystalline human immunoglobulins of normal structure (two heavy chains linked to two light chains) were described over the next thirty years, again mostly isolated from myeloma patients (Putnam, F. W. (1955) Science 122: 275-7). Davies and co-workers were the first to characterize the structure of an intact human myeloma antibody, named "Dob", using x-ray crystallography (Terry, W. D. et al. (1968) Nature 220(164): 239-41), and they determined its three-dimensional structure in 1971 (Sarma, V. R. et al. (1971) J. Biol. Chem. 246(11): 3753-9). Their pioneering work was followed by that of others, yielding the crystal structures of the IgG "Kol" (Huber, R. et al. (1976) Nature 264(5585): 415-20), the IgG "Mcg" (Rajan, S. S. et al. (1983) Mol. Immunol. 20(7): 787-99), and a canine lymphoma IgG2a (Harris, L. J. et al. (1992 Nature 360(6402): 369-72).

Crystals of immunoglobulins retain their distinctive immunological activities upon re-dissolution. Nisonoff et al. reported in 1968 on a rabbit anti-p-azobenzoate antibody, "X4", that was easily crystallized (Nisonoff, A. et al. (1968) Cold Spring Harbor Symposia on Quantitative Biology 32: 89-93). Antibody X4 was extensively characterized before crystallization as well as after re-dissolution of the crystals. [$^{125}$I]-p-iodobenzoate was found to bind specifically and potently to re-dissolved X4; the redissolved crystals also exhibited multiple specific Ouchterlony immunodiffusion reactions typical of the unpurified rabbit serum (Nisonoff et al., 1968). Connell and co-workers described a human myeloma gamma-immunoglobulin-1 kappa (IgG-κ), called "Tem", that crystallized spontaneously from serum at cold temperatures (Connell, G. E. et al. (1973) Canad. J. Biochem. 51(8): 1137-41). Tem crystals were found to be well-formed and possessed rhombohedral symmetry. Tem-containing serum was extensively characterized by agarose immunodiffusion techniques. Electrophoresis and immunodiffusion of a re-dissolved solution of the Tem crystals showed them to be identical with the material obtained from the serum by cryoprecipitation, and with the isolated myeloma protein (Connell et al., 1973).

Mills and co-workers reported in 1983 an unusual crystallocryoglobulinemia resulting from human monoclonal antibodies to albumin (Mills, L. E. et al. (1983) Annals of Internal Med 99(5): 601-4). Here, very similar cuboidal crystals were isolated from two patients. Redissolution of the crystals followed by electrophoresis and immunoelectrophoresis indicated that the crystals were composed of two protein components, a monoclonal IgG-lambda and human serum albumin in a 1:2 ratio (Jentoft, J. E. et al. (1982) Biochem. 21(2): 289-294). The components were separated on preparative scale by dissolution of the original crystals followed by column chromatography. Although neither separated component crystallized on its own, upon recombination the original bipartite complex reformed and then crystallized. Further study of the distinctive sedimentation characteristics and immunological reactivity of the redissolved, separated IgG and its Fab fragment with human serum albumin indicated that reassociation of the two redissolved, separated components was immunologic in nature, i.e., that the crystalline antibody once redissolved still possessed its native, highly specific (for human serum albumin) binding characteristics (Mills et al. 1983).

Recently, Margolin and co-workers reported on the potential therapeutic uses of crystalline antibodies (Yang, M. X. et al. (2003) Proc. Natl. Acad. Sci. 100(12): 6934-6939). They found that the therapeutic monoclonal antibody trastuzumab (Herceptin®) could be crystallized (Shenoy, B. et al. (2002) PCT Int. Appl. WO/2002/072636, (Altus Biologics Inc., USA). 173 pp.). Crystalline trastuzumab suspensions were therapeutically efficacious in a mouse tumor model, thus demonstrating retention of biological activity by crystalline trastuzumab (Yang et al., 2003).

b) Crystallization Techniques

The crystallization of diverse proteins cannot be carried out successfully using defined methods or algorithms. Certainly, there have been great technical advances in the last 20-30 years, as noted by the world-renowned expert in protein crystallization, A. McPherson. McPherson provides extensive details on tactics, strategies, reagents, and devices for the crystallization of macromolecules. (McPherson, A. (1999) Crystallization of Biological Macromolecules. Cold Spring Harbor, N.Y., Cold Spring Harbor Laboratory Press, p. 159). He does not, however, provide a method to ensure that any given macromolecule can indeed be crystallized by a skilled person with reasonable expectation of success. McPherson states for example: "Whatever the procedure, no effort must be spared in refining and optimizing the parameters of the system, both solvent and solute, to encourage and promote specific bonding interactions between molecules and to stabilize them once they have formed. This latter aspect of the problem generally depends on the specific chemical and physical properties of the particular protein or nucleic acid being crystallized.".

It is widely accepted by those skilled in the art of protein crystallization that no algorithm exists to take a new protein of interest, apply definite process steps, and thereby obtain the desired crystals.

Several screening systems are commercially available (for example Hampton 1 and 2, Wizzard I and II) which allow, on a microliter scale, to screen for potentially suitable crystallization conditions for a specific protein. However, positive results obtained in such a screening system do not necessarily allow successful crystallization in a larger, industrially applicable batch scale. Conversion of microliter-size crystallization trials into industrial dimensions is described to be a challenging task (see Jen, A., Merkle, H. P. (2001) Pharm. Res. 18, 11, 1483).

Baldock et al. reported on a comparison of microbatch and vapor diffusion for initial screening of crystallization conditions (Baldock, P. et al. (1996) J. Crystal Growth 168(1-4): 170-174. Six commercially available proteins were screened using a set of crystallization solutions. The screens were performed using the most common vapor diffusion method and three variants of a microbatch crystallization method, including a novel evaporation technique. Out of 58 crystallization conditions identified, 43 (74%) were identified by microbatch, while 41 (71%) were identified by vapor diffusion. Twenty-six conditions were found by both methods, and 17 (29%) would have been missed if microbatch had not been used at all. This shows that the vapor diffusion technique, which is most commonly used in initial crystallization screens does not guarantee positive results.

c) Anti-Human IL-12 Antibody Crystals

Human IL-12 plays a critical role in the pathology associated with several diseases involving immune and inflammatory responses, for example multiple sclerosis, Crohn's disease and psoriasis. There is, therefore, a great need for suitable methods of treating such human IL-12 related disorders. One promising therapeutic approach comprises the administration of pharmaceutically effective doses of anti-human IL-12 antibodies.

Due to the role of human IL-12 in a variety of human disorders, therapeutic strategies have been designed to inhibit or counteract IL-12 activity. In particular, antibodies that bind to, and neutralize, IL-12 have been sought as a means to inhibit IL-12 activity. Some of the earliest antibodies were murine monoclonal antibodies (mAbs), secreted by hybridomas prepared from lymphocytes of mice immunized with IL-12 (see, e.g., WO 97/15327). These murine IL-12 antibodies are, however, limited for their use in vivo due to problems associated with administration of mouse antibodies to humans, such as short serum half life, an inability to trigger certain human effector functions and elicitation of an unwanted immune response against the mouse antibody in a human (the "human anti-mouse antibody" (HAMA) reaction).

In general, attempts to overcome the problems associated with the use of fully-murine antibodies in humans, have involved genetically engineering the antibodies to be more "human-like." For example, chimeric antibodies, in which the variable regions of the antibody chains are murine-derived and the constant regions of the antibody chains are human-derived, have been prepared. However, because these chimeric and humanized antibodies still retain some murine sequences, they still may elicit an unwanted immune reaction, the human anti-chimeric antibody (HACA) reaction, especially when administered for prolonged periods.

U.S. Pat. No. 6,914,128 discloses human antibodies, preferably recombinant human antibodies, that specifically bind to human interleukin-12 (hIL-12). Preferred antibodies disclosed therein, have high affinity for hIL-12 and neutralize hIL-12 activity in vitro and in vivo. The antibodies, or antibody portions, are useful for detecting hIL-12 and for inhibiting hIL-12 activity, e.g., in a human subject suffering from a disorder in which hIL-12 activity is detrimental. Nucleic acids, vectors and host cells for expressing the recombinant human antibodies of the invention, and methods of synthesizing the recombinant human antibodies, are also enclosed. Crystalline forms of the anti-hIL-12 antibodies or methods for preparing the same are not specifically described in the '128 patent.

The problem to be solved according to the present invention is, therefore, to develop suitable crystallization conditions, in particular batch crystallization conditions, for anti-IL-12 antibodies, and to establish crystallization process conditions applicable to volumes relevant for industrial antibody crystal production. At the same time, a crystallization process is established that does not make use of toxic agents, which might negatively affect the pharmaceutical applicability of such antibodies.

SUMMARY OF THE INVENTION

The above-mentioned problem was, surprisingly, solved by the finding that it is possible to obtain crystals of a whole anti-human IL-12 antibody in batch crystallization volumes above the microliter scale by applying physiologically acceptable polyalkylene polyols as the crystallization-inducing agent.

In a first aspect, the invention provides a batch crystallization method for crystallizing an anti-human IL-12 antibody, comprising the steps of:
(a) providing an aqueous solution of the IL-12 antibody in admixture with at least one crystallization agent of the polyalkylene polyol type, as defined in more detail below, for example polyalkylene glycol; for example by mixing an aqueous solution of the antibody, wherein the antibody preferably is present in dissolved form, with an aqueous crystallization solution comprising at least one polyalkylene glycol as crystallization agent in dissolved form, or alternatively by adding the crystallization agent in solid form;
(b) and incubating the aqueous crystallization mixture until crystals of the antibody are formed.

According to a further embodiment, the method of the present invention may also be performed such that the crystallization mixture obtained in step a) may be supplemented with a suitable amount of pre-existing anti-human IL-12 antibody crystals as seed crystals in order to initiate or boost the crystallization.

The crystallization method of the invention generally is performed at a pH of the aqueous crystallization mixture in the range of about pH 4 to about 6.5, in particular about 4.5 to about 6.0, about 5.0 to about 5.8 or about 5.3 to about 5.7, such as, for example, 5.4, 5.5 or 5.6.

Moreover, the aqueous crystallization mixture may contain at least one buffer. The buffer may comprise an acetate component as a main component, especially an alkali metal salt thereof, for example a sodium or a potassium salt, such as sodium acetate. The salt is adjusted by addition of an acid, in particular acetic acid, to the required pH. In a preferred embodiment of the crystallization method, the buffer concentration (total acetate) in the aqueous crystallization mixture is about 0 to about 0.5 M, or about 0.02 to about 0.5 M, as for example about 0.05 to about 0.3 M, or about 0.07 to about 0.2 M, or about 0.09 to about 0.12 M.

A "crystallization agent of the polyalkylene polyol type" is defined in more detail below:

A skilled reader will realize that the term has to be understood broadly and comprises polyalkylene polyols as well as derivatives thereof.

A "polyalkylene polyol" as used according to the invention is a straight or branched chain, in particular straight chain, poly-$C_2$-$C_6$-alkylene polyol. The polyether is formed from at least one type of a polyfunctional aliphatic alcohol carrying 2 to 6, 2 to 4 and in particular 2 or 3, preferably vicinal, hydroxyl groups and having 2 to 6, in particular 2, 3 or 4 carbon atoms, preferably forming a linear carbon backbone. Non-limiting examples are ethylene-1,2-diol (glycol), propylene-1,2-diol, propylene-1,3-diol, and n-butylene-1,3-diol and n-butylene-1,4-diol. A particularly preferred diol is glycol.

The polyalkylene polyols of the invention may be composed of one single type of polyol or mixtures of at least to different polyols, which may be polymerized at random or may be present as block copolymers.

Furthermore, the term "polyalkylene polyol" also comprises derivatives of the same. Non-limiting examples are alkyl esters and ethers, in particular monoalkyl ethers and dialkyl ethers. "Alkyl" is in particular defined as straight or branched-chain $C_1$-$C_6$-alkyl residue, in particular, methyl, ethyl, n- or i-propyl, n-, i-, sec.-oder tert.-butyl, n- or i-pentyl; and n-hexyl.

The polyalkylene polyols, in particular the polyalkylene glycols, as used according to the invention are further characterized by a wide range of molecular weights. The molecular weight range, stated as number- or weight average molecular weight, typically is in the range of 400 to 10,000, as for example 1,000 to 8,000, or 2,000 to 6,000 3,000 to 6,000 or 3,200 to 6,000, as for example 3,350 to 6,000, 3,350 to 5000, or 3,800 to 4,200, in particular about 4,000.

Particular polyalkylene polyols are polyethylene glycols (PEGs) and polypropylene glycols (PPGs) and corresponding random or block copolymers. Specific examples of suitable polyols are PEG 2,000, PEG 3,000, PEG 3,350, PEG 4,000, PEG 5,000 and PEG 6,000.

In particular, the polyalkylene polyol concentration, in particular the polyethylene glycol concentration, in the crystallization mixture is in the range of about 5 to about 30% (w/v), as for example about 7 to about 15% (w/v) or about 9 to about 16% (w/v) or about 10 to about 14% (w/v) or about 11 to about 13% (w/v). Preferably, polyethylene glycol with an average molecular weight of about 4,000 is used in a concentration in the crystallization mixture of about 11 to about 13% (w/v).

In a preferred embodiment of the invention, antibody protein solution and crystallization solution are combined in a ratio of about 1:1. Thus, molarities of the buffering agents/crystallization agents in the original crystallization solution are about double as high as in the crystallization mixture.

Typically, the crystallization method is performed in a batch volume in the range of about 1 ml to about 20,000 l, or 1 ml to about 15,000 l, or 1 ml to about 12,000 l, or about 1 ml to about 10,000 l, or 1 ml to about 6,000 l, or 1 ml to about 3,000 l, or 1 ml to about 1,000 l, or 1 ml to about 100 l, as for example about 50 ml to about 8,000 ml, or about 100 ml to about 5,000 ml, or about 1,000 ml to about 3,000 ml; or about 1 l to about 1,000 l; or about 10 l to about 500 l.

In addition, the crystallization method of the invention may be performed so that at least one of the following additional crystallization conditions is achieved:
a) incubation is performed for between about 1 hour to about 250 days, or 1 to 250 days or 13 to 250 days, for example about 1 to about 30 days, or about 2 to 10 days;
b) incubation is performed at a temperature between about 0° C. and about 50° C., for example about 4° C. and about 37° C. or about 15° C. and about 25° C.;
c) the antibody concentration (i.e., protein concentration) in the crystallization mixture is in the range of about 0.5 to 280 mg/ml or about 1 to 200 mg/ml or 1 to 100 mg/ml, for example 1.5 to 20 mg/ml, in particular in the range of about 2 to 15 mg/ml, or 5 to 10 mg/ml. The protein concentration may be determined according to standard procedures for protein determination.

In a preferred embodiment, the crystallization method, for example with polyethylene glycol as the crystallization agent, is performed such that the incubation is performed for between about 13 to 60 days at a temperature of about 20° C. and at an antibody concentration of about 5 to 10 mg/ml.

According to a particularly preferred method, crystallization is performed under the following conditions of the crystallization mixture:

| | |
|---|---|
| Polyalkylene glycol: | PEG 4000 10 to 15% (w/v) |
| buffer: | sodium acetate, 0 to 0.3M, (total acetate) |
| pH: | 5.3 to 5.8 |
| anti-hIL-12 concentration: | 3 to 10 mg/ml |
| Temperature: | 18 to 24° C. |
| Batch volume: | 1 to 100 l |
| Agitation: | None |
| Duration: | about 1 to 60 days |

The crystallization mixtures as outlined above are usually obtained by adding a crystallization agent in solution or as solid to the protein solution. Both solutions may be, but do not have to be buffered. Crystallization agent concentration and buffer molarity in the original crystallization solution is usually higher than in the crystallization mixture as it is "diluted" with the protein solution.

In a further embodiment, the crystallization method of the invention may further comprise the step of drying the obtained crystals. Suitable drying methods comprise evaporative drying, spray drying, lyophilization, vacuum drying, fluid bed drying, spray freeze drying, near critical drying, supercritical drying, and nitrogen gas drying.

In a further embodiment, the crystallization method of the invention may further comprise the step of exchanging the crystallization mother liquor with a different liquid or buffered buffer, e.g., a liquid or buffer containing a polyalkylene polyol different from the one used for crystallization with a molar mass in the range of about 300 to 8,000 Daltons or mixtures of such polyols, for example by centrifugation, diafiltration, ultrafiltration or other commonly used buffer exchange techniques. The different liquid or buffer may also be designated as an "artificial mother liquor" which differs from the "natural" crystallization mother liquor of the crystals and prevents a dissolution of the crystals formed.

The present invention also relates to a crystal of an anti-hIL-12 antibody, obtainable by a crystallization method as defined above and in general to crystals of an anti-hIL-12 antibody.

The crystals of the invention may be of different shape. The shape generally is designated as "sword-like". In particular, the term also comprises "platelets", "needles" or "needle-clusters" (sea urchin-like). For example, the crystals of the invention may be characterized by a needle-like morphology with a maximum length (l) of about 2-500 µm or about 100-300 µm and a length/diameter (l/d) ratio of about 1 to 100. The height of such needle-like crystals is roughly in the dimension of the diameter.

Platelets of the invention may have the following dimensions: A maximum length (l) of about 2-500 µm or about 100-300 µm and a length/diameter (l/d) ratio of about 1 to 100. The height of such platelets is considerably smaller than the diameter.

Needle-clusters of the invention may have the following dimensions. A maximum length l of about 2-200 µm or about 10-100 µm and a length/diameter (l/d) ratio of about 1 to 3.

The crystal may be obtained from a polyclonal antibody or, preferably, a monoclonal antibody.

In particular, the antibody is selected from the group consisting of non-chimeric or chimeric antibodies, humanized antibodies, non-glycosylated antibodies, human antibodies and mouse antibodies. In particular the antibody to be crystallized is a non-chimeric, human antibody optionally further processed for improving the antigen-binding and/or efficacy.

Preferably, the crystals are obtained from an IgG antibody such as, for example, an IgG1, IgG2, IgG3 or IgG4 antibody. In particular, the antibody is a whole anti-human IL-12 antibody of the group IgG1.

In a preferred embodiment, the crystals are prepared from an isolated human antibody, that dissociates from hIL-12 with a Kd of $1\times10^{-10}$ M or less and a $k_{off}$ rate constant of $1\times10^{-3}$ s$^{-1}$ or less, both determined by surface plasmon resonance.

In particular, the crystals may be prepared from an isolated human antibody with a light chain variable region (LCVR) comprising the amino acid sequence of SEQ ID NO: 2 and a heavy chain variable region (HCVR) comprising the amino acid sequence of SEQ ID NO: 1.

Preferred human antibodies are, for example described in U.S. Pat. No. 6,914,128.

Most preferred are crystals prepared from the antibody ABT-874.

In a further embodiment, the invention relates to a solid, liquid or semi-solid pharmaceutical composition comprising: (a) crystals of an anti-hIL-12 antibody as defined above, and (b) at least one pharmaceutically acceptable excipient stably maintaining the antibody crystals.

Another aspect of this invention relates to a solid, liquid or semi-solid pharmaceutical composition comprising: (a) crystals of an anti-hIL-12 antibody as defined herein, and (b) at least one pharmaceutically acceptable excipient encapsulating or embedding the antibody crystals. The composition may further comprise (c) at least one pharmaceutically acceptable excipient stably maintaining the antibody crystals. Moreover, encapsulation and embedding may be implemented in conjunction.

In particular, the compositions of the invention may have an antibody crystal concentration higher than about 1 mg/ml, in particular about 200 mg/ml or more, for example about 200 to about 600 mg/ml, or about 300 to about 500 mg/ml.

The excipients may comprise at least one polymeric, optionally biodegradable carrier or at least one oil or lipid carrier.

The polymeric carrier may be one or more polymer selected from the group consisting of: poly (acrylic acid), poly (cyanoacrylates), poly (amino acids), poly (anhydrides), poly (depsipeptide), poly (esters), poly (lactic acid), poly (lactic-co-glycolic acid) or PLGA, poly (β-hydroxybutryate), poly (caprolactone), poly (dioxanone); poly (ethylene glycol), poly (hydroxypropyl) methacrylamide, poly (organo) phosphazene, poly (ortho esters), poly (vinyl alcohol), poly (vinylpyrrolidone), maleic anhydride alkyl vinyl ether copolymers, pluronic polyols, albumin, alginate, cellulose and cellulose derivatives, collagen, fibrin, gelatin, hyaluronic acid, oligosaccharides, glycaminoglycans, sulfated polysaccharides, blends and copolymers thereof.

The oil (or oily liquid) may be one or more oil (or oily liquid) selected from the group consisting of oleaginous almond oil, corn oil, cottonseed oil, ethyl oleate, isopropyl myristate, isopropyl palmitate, mineral oil, light mineral oil, octyldodecanol, olive oil, peanut oil, persic oil, sesame oil, soybean oil, squalane, liquid triglycerides, liquid waxes, and higher alcohols.

The lipid carrier may be one or more lipid selected from the group consisting of fatty acids and salts of fatty acids, fatty alcohols, fatty amines, mono-, di-, and triglycerides of fatty acids, phospholipids, glycolipids, sterols and waxes and related similar substances. Waxes are further classified in natural and synthetic products. Natural materials include waxes obtained from vegetable, animal or minerals sources such as beeswax, carnauba or montanwax. Chlorinated naphthalenes and ethylenic polymers are examples for synthetic wax products.

In a preferred embodiment, the composition is an injectable composition comprising anti-hIL-12 antibody crystals as defined above and having an antibody crystal concentration in the range of about 10 to about 400 mg/ml or about 50 to about 300 mg/ml.

In a further aspect the invention relates to a crystal slurry comprising anti-hIL-12 antibody crystals as defined above having an antibody crystal concentration higher than about 100 mg/ml, for example about 150 to about 600 mg/ml, or about 200 to about 400 mg/ml.

The present invention also relates to a method for treating a mammal comprising the step of administering to the mammal an effective amount of whole anti-hIL-12 antibody crystals as defined above or an effective amount of the composition as defined above. Preferably, the composition is administered by parenteral route, oral route, or by injection.

Furthermore, the present invention relates to a method of treating a hIL-12-related disorder in a subject that comprises administering a therapeutically effective amount of antibody crystals as defined above.

In particular, the hIL-12-related disorder is selected from: rheumatoid arthritis, osteoarthritis, juvenile chronic arthritis, Lyme arthritis, psoriatic arthritis, reactive arthritis, spondyloarthropathy, systemic lupus erythematosus, Crohn's disease, ulcerative colitis, inflammatory bowel disease, insulin dependent diabetes mellitus, thyroiditis, asthma, allergic diseases, psoriasis, dermatitis scleroderma, atopic dermatitis, graft versus host disease, organ transplant rejection, acute or chronic immune disease associated with organ transplantation, sarcoidosis, atherosclerosis, disseminated intravascular coagulation, Kawasaki's disease, Grave's disease, nephrotic syndrome, chronic fatigue syndrome, Wegener's granulomatosis, Henoch-Schoenlein purpurea, microscopic vasculitis of the kidneys, chronic active hepatitis, uveitis, septic shock, toxic shock syndrome, sepsis syndrome, cachexia, infectious diseases, parasitic diseases, acquired immunodeficiency syndrome, acute transverse myelitis, Huntington's chorea, Parkinson's disease, Alzheimer's disease, stroke, primary biliary cirrhosis, hemolytic anemia, malignancies, heart failure, myocardial infarction, Addison's disease, sporadic, polyglandular deficiency type I and polyglandular deficiency type II, Schmidt's syndrome, adult (acute) respiratory distress syndrome, alopecia, alopecia areata, seronegative arthopathy, arthropathy, Reiter's disease, psoriatic arthropathy, ulcerative colitic arthropathy, enteropathic synovitis, chlamydia, yersinia and salmonella associated arthropathy, spondyloarthopathy, atheromatous disease/arteriosclerosis, atopic allergy, autoimmune bullous disease, pemphigus vulgaris, pemphigus foliaceus, pemphigoid, linear IgA disease, autoimmune haemolytic anaemia, Coombs positive haemolytic anaemia, acquired pernicious anaemia, juvenile pernicious anaemia, myalgic encephalitis/Royal Free Disease, chronic mucocutaneous candidiasis, giant cell arteritis, primary sclerosing hepatitis, cryptogenic autoimmune hepatitis, Acquired Immunodeficiency Disease Syndrome, Acquired Immunodeficiency Related Diseases, Hepatitis C, common varied immunodeficiency (common variable hypogammaglobulinaemia), dilated cardiomyopathy, female infertility, ovarian failure, premature ovarian failure, fibrotic lung disease, cryptogenic fibrosing alveolitis, post-inflammatory interstitial lung disease, interstitial pneumonitis, connective tissue disease associated interstitial lung disease, mixed connective tissue disease associated lung disease, systemic sclerosis associated interstitial lung disease, rheumatoid arthritis associated interstitial lung disease, systemic lupus erythematosus associated lung disease, dermatomyositis/polymyositis associated lung disease, Sjodgren's disease associated lung disease, ankylosing spondylitis associated lung disease, vasculitic diffuse lung disease, haemosiderosis associated lung disease, drug-induced interstitial lung disease, radiation fibrosis, bronchiolitis obliterans, chronic eosinophilic pneumonia, lymphocytic infiltrative lung disease, postinfectious interstitial lung disease, gouty arthritis, autoimmune hepatitis, type-1 autoimmune hepatitis (classical autoimmune or lupoid hepatitis), type-2 autoimmune hepatitis (anti-LKM antibody hepatitis), autoimmune mediated hypoglycemia, type B insulin resistance with acanthosis nigricans, hypoparathyroidism, acute immune disease associated with organ transplantation, chronic immune disease associated with organ transplantation, osteoarthrosis, primary sclerosing cholangitis, idiopathic leucopenia, autoimmune neutropenia, renal disease NOS, glomerulonephritides, microscopic vasulitis of the kidneys, lyme disease, discoid lupus erythematosus, male infertility idiopathic or NOS, sperm autoimmunity, multiple sclerosis (all subtypes), insulin-dependent diabetes mellitus, sympathetic ophthalmia, pulmonary hypertension secondary to connective tissue disease, Goodpasture's syndrome, pulmonary manifestation of polyarteritis nodosa, acute rheumatic fever, rheumatoid spondylitis, Still's disease, systemic sclerosis, Takayasu's disease/arteritis, autoimmune thrombocytopenia, idiopathic thrombocytopenia, autoimmune thyroid disease, hyperthyroidism, goitrous autoimmune hypothyroidism (Hashimoto's disease), atrophic autoimmune hypothyroidism, primary myxoedema, phacogenic uveitis, primary vasculitis and vitiligo. The human antibodies, and antibody portions of the invention can be used to treat autoimmune diseases, in particular those associated with inflammation, including, rheumatoid spondylitis, allergy, autoimmune diabetes, autoimmune uveitis.

Moreover, the present invention relates to the use of whole anti-hIL-12 antibody crystals as defined above for preparing a pharmaceutical composition for treating a hIL-12-related disease as defined above.

Finally, the present invention provides anti-hIL-12 antibody crystals as defined above for use in medicine.

BRIEF DESCRIPTION OF THE DRAWINGS

The foregoing and other objects, features and advantages of the present invention, as well as the invention itself, will be more fully understood from the following description of preferred embodiments when read together with the accompanying drawings, in which:

FIG. 2: 1,250×; FIG. 3: 10,000×; FIG. 4: 3,227×; FIG. 5: 15,000×.

FIG. 6A) ABT-874 crystal buffer and pl markers of pl 8.4, 8.5, 10.1 and 10.4; FIG. 6B) ABT-874 crystals; same pl marker and characteristic ABT-874 signal at pl=9,29; FIG. 6C) Reference Standard; same pl marker and characteristic ABT-874 signal at pl=9,29.

FIG. 11A shows spectra of crystal suspension recorded with an BioATR cell. FIG. 11B shows spectra of redissolved crystals recorded with an AquaSpec cell. Solid lines represent samples from crystalline ABT-874, dashed lines represent liquid standards. An offset between sample and standard was inserted for better illustration.

FIG. 12A shows spectra of crystal suspension recorded with an BioATR cell. FIG. 12B shows spectra of redissolved crystals recorded with an AquaSpec cell. An offset between sample and standard was inserted for better illustration.

DETAILED DESCRIPTION OF THE INVENTION

A. Definitions

Figure 1:
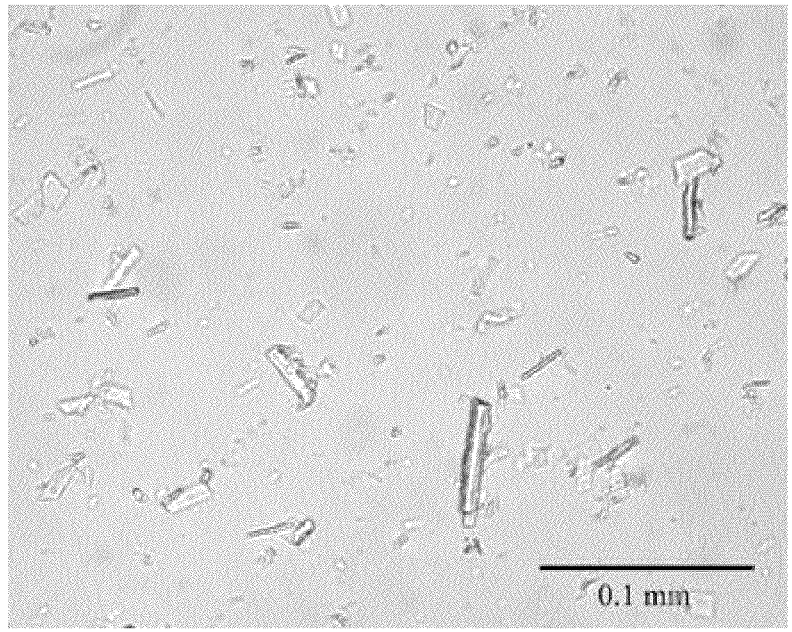
FIG. 1 shows a light micrograph of ABT-874 crystals in crystallization.

A "batch method of crystallization" comprises the step of adding the crystallization solution comprising the crystallization agent, preferably in dissolved form, to the solution of the antibody to be crystallized.

A "micro scale crystallization method", which may for example be based upon vapor diffusion, comprises the steps of mixing a small volume of antibody solution in the microliter range with a reservoir buffer containing a crystallization agent; placing a droplet of the mixture in a sealed container adjacent to an aliquot of the reservoir buffer; allowing exchange of solvent between the droplet and the reservoir by vapor diffusion, during which the solvent content in the droplet changes and crystallization may be observed if suitable crystallization conditions are reached.

A "crystallization agent", e.g., a polyethylene glycol, favors crystal formation of the antibody to be crystallized.

A "crystallization solution" contains a crystallization agent in dissolved form. Preferably the solution is an aqueous system, i.e., the liquid constituents thereof predominantly consist of water. For example, 80 to 100 wt.-% or 95 to 100 wt.-% or 98 to 100 wt.-% may be water.

Antibody "crystals" are one form of the solid state of matter of the protein, which is distinct from a second solid form, i.e., the amorphous state, which exists essentially as an unorganized, heterogeneous solid. Crystals have a regular three-dimensional structure, typically referred to as a lattice. An antibody crystal comprises a regular three-dimensional array of antibody molecules (see Giege, R. and Ducruix, A. Barrett, Crystallization of Nucleic Acids and Proteins, a Practical Approach, 2nd ed., pp. 1-16, Oxford University Press, New York (1999)).

A "whole" or "intact" anti-hIL-12 antibody as crystallized according to this invention, is a functional antibody that is able to recognize and bind to its antigen human IL-12 in vitro and/or in vivo. The antibody may initiate subsequent immune system reactions of a patient associated with antibody-binding to its antigen, in particular Direct Cytotoxicity, Complement-Dependent Cytotoxicity (CDC), and Antibody-Dependent Cytotoxicity (ADCC). The antibody molecule has a structure composed of two identical heavy chains (MW each about 50 kDa) covalently bound to each other, and two identical light chains (MW each about 25 kDa), each covalently bound to one of the heavy chains. The four chains are arranged in a classic "Y" motif. Each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The complete antibody molecule has two antigen binding sites, i.e., is "bivalent". The two antigen binding sites are specific for one hIL-12 antigen, i.e., the antibody is "mono-specific".

"Monoclonal antibodies" are antibodies that are derived from a single clone of B lymphocytes (B cells), and recognize the same antigenic determinant. Whole monoclonal antibodies are those that have the above-mentioned classic molecular structure that includes two complete heavy chains and two complete light chains. Monoclonal antibodies are routinely produced by fusing the antibody-producing B cell with an immortal myeloma cell to generate B cell hybridomas, which continually produce monoclonal antibodies in cell culture. Other production methods are available, for example, expression of monoclonal antibodies in bacterial, yeast, insect, or mammalian cell culture using phage-display technology; in vivo production in genetically modified animals, such as cows, goats, pigs, rabbits, chickens, or in transgenic mice which have been modified to contain and express the entire human B cell genome; or production in genetically modified plants, such as tobacco and corn. Anti-hIL-12 antibodies from all such sources may be crystallized according to this invention.

The monoclonal antibodies to be crystallized according to the invention include "chimeric" anti-hIL-12 antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass. For example, a mouse/human chimera contains the variable antigen-binding portions of a murine antibody and the constant portions derived from a human antibody.

"Humanized" forms of non-human (e.g., murine) anti-hIL-12 antibodies are also encompassed by the invention. Humanized antibodies are chimeric antibodies that contain minimal sequence derived from a non-human immunoglobulin. For the most part, humanized antibodies are human immunoglobulins in which residues from one or more complementarity determining regions (CDRs) or hypervariable loops (HVLs) of the human immunoglobulin are replaced by residues from a CDR or HVL of a non-human species, such as mouse, rat, rabbit or nonhuman primate, having the desired functionality. Framework region (FR) residues of the human immunoglobulin may replaced by corresponding non-human residues to improve antigen binding affinity. Furthermore, humanized antibodies may comprise residues that are found neither in the corresponding human or non-human antibody portions. These modifications may be necessary to further improve antibody efficacy.

A "human antibody" or "fully human antibody" is one, which has an amino acid sequence which corresponds to that of an antibody produced by a human or which is recombinantly produced. The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The term "recombinant human antibody", as used herein, is intended to include all human antibodies that are prepared, expressed, created or isolated by recombinant means, such as antibodies expressed using a recombinant expression vector transfected into a host cell, antibodies isolated from a recombinant, combinatorial human antibody library, antibodies isolated from an animal (e.g., a mouse) that is transgenic for human immunoglobulin genes (see, e.g., Taylor, L. D. et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

A "neutralizing antibody", as used herein (or an "antibody that neutralized hIL-12 activity"), is intended to refer to an antibody whose binding to hIL-12 results in inhibition of the biological activity of hIL-12. This inhibition of the biological activity of hIL-12 can be assessed in vitro or in vivo by measuring one or more indicators of hIL-12 biological activity, such as hIL-12-induced cell proliferation and hIL-12 binding to hIL-12 receptors or hIL-12 induced decrease of white blood cells in vivo.

These indicators of hIL-12 biological activity can be assessed by one or more of several standard in vitro or in vivo assays known in the art. Preferably, the ability of an antibody to neutralize hIL-12 activity is assessed by inhibition of hIL-12-induced cell proliferation in phytohemagglutinin blasts and murine 2D6 cells.

An "affinity matured" anti-hIL-12 antibody is one with one or more alterations in one or more hypervariable regions, which result in an improvement in the affinity of the antibody for antigen, compared to a parent antibody. Affinity matured antibodies will have nanomolar or even picomolar affinities values for the target antigen. Affinity matured antibodies are produced by procedures known in the art. Marks et al. (1992) Bio/Technology 10:779-783 describes affinity maturation by VH and VL domain shuffling. Random mutagenesis of CDR and/or framework residues is described by Barbas et al. (1994) Proc. Nat. Acad. Sci. USA 91:3809-3813 (1994); Scier et al. (1995) Gene 169:147-155; Yelton et al. (1995) J. Immunol. 155:1994-2004; Jackson et al. (1995) J. Immunol. 154(7):3310-9; and Hawkins et al. (1992) J. Mol. Biol. 226: 889-896.

An "isolated antibody", as used herein, is intended to refer to an antibody that is substantially free of other antibodies having different antigenic specificities (e.g., an isolated antibody that specifically binds hIL-12 is substantially free of antibodies that specifically bind antigens other than hIL-12). An isolated antibody that specifically binds hIL-12 may, however, have cross-reactivity to other antigens, such as hIL-12 molecules from other species. Moreover, an isolated antibody may be substantially free of other cellular material and/or chemicals.

The phrase "human interleukin 12" (abbreviated herein as hIL-12, or IL-12), as used herein, includes a human cytokine that is secreted primarily by macrophages and dendritic cells. The term includes a heterodimeric protein comprising a 35 kD subunit (p35) and a 40 kD subunit (p40) which are both linked together with a disulfide bridge. The heterodimeric protein is referred to as a "p70 subunit". The structure of human IL-12 is described further in, for example, Kobayashi, et al. (1989) J. Exp Med. 170:827-845; Seder, et al. (1993) Proc. Natl. Acad. Sci. 90:10188-10192; Ling, et al. (1995) J. Exp Med. 154:116-127; Podlaski, et al. (1992) Arch. Biochem. Biophys. 294:230-237. The term human IL-12 is intended to include recombinant human IL-12 (rh IL-12), which can be prepared by standard recombinant expression methods.

The term "$k_{off}$", as used herein, is intended to refer to the off rate constant for dissociation of an antibody from the antibody/antigen complex.

The term "$K_d$", as used herein, is intended to refer to the dissociation constant of a particular antibody-antigen interaction.

A "functional equivalent" of a specific "parent" anti-hIL-12 antibody as crystallized according to the invention is one that shows the same antigen-specificity, but differs however with respect to the molecular composition of the "parent" antibody on the amino acid level or glycosylation level. The differences may be merely such that the crystallization conditions do not deviate from the parameter ranges as disclosed herein.

"Encapsulation" of antibody crystals refers to a formulation where the incorporated crystals are individually coated by at least one layer of a coating material. In a preferred embodiment, such coated crystals may have a sustained dissolution rate.

"Embedding" of antibody crystals refers to a formulation where the crystals, which might be encapsulated or not, are incorporated into a solid, liquid or semi-solid carrier in a disperse manner. Such embedded crystallized antibody molecules may be released or dissolved in a controlled, sustained manner from the carrier.

B. Method of Crystallization

The crystallization method of the invention is in principle applicable to any anti-hIL-12 antibody. The antibody may be a polyclonal antibody or, preferably, a monoclonal antibody. The antibody may be chimeric antibodies, humanized antibodies, human antibodies or non-human, as for example mouse antibodies, each in glycosylated or non-glycosylated form. In particular the method is applicable to ABT-874 and functional equivalents thereof.

Preferably the anti-hIL-12 antibody is an IgG antibody, in particular an anti human IL-12 antibody of the group IgG1.

Unless otherwise stated the crystallization method of the invention makes use of technical equipment, chemicals and methodologies well known in the art. However, as explained above, the present invention is based on the surprising finding that the selection of specific crystallization conditions, in particular, the selection of specific crystallization agents, optionally further combined with specific pH conditions and/or concentration ranges of the corresponding agents (buffer, antibody, crystallization agent), allows for the first time to prepare reproducibly and in a large scale stable crystals of antibodies, in particular non-chimeric, human antibodies, directed against hIL-12, which can be further processed to form an active ingredient of a superior, highly advantageous pharmaceutical composition.

The starting material for performing the crystallization method normally comprises a concentrated solution of the antibody to be crystallized. The protein concentration may, for example, be in the range of about 5 to about 300 mg/ml, preferably about 5 to about 200 mg/ml, preferably about 5 to about 75 mg/ml. The solution may contain additives stabilizing the dissolved antibody, and it may be advisable to remove the additives in advance. This can be achieved by performing a buffer exchange step.

Preferably the starting material for performing the crystallization contains the antibody in an aqueous solution, having a pH adjusted in the range of about 3.2 to about 8.2, or about 4.0 to about 8.0, in particular about 4.5 to about 6.5, preferably about 5.0 to about 5.5. The pH may be adjusted by means of a suitable buffer applied in a final concentration of about 1 to about 500 mM, in particular about 1 to about 100 mM or 1 to about 10 mM. The solution may contain additives, as for example in a proportion of about 0.01 to about 15, or about 0.1 to about 5, or about 0.1 to about 2 wt.-% based on the total weight of the solution, such as salts, sugars, sugar alcohols and surfactants, in order to further stabilize the solution. The excipients are preferably be selected from physiologically acceptable compounds, routinely applied in pharmaceutical preparations. As non-limiting examples, excipients include salts, such as NaCl; surfactants, such as polysorbate 80 (Tween 80), polysorbate 20 (Tween 20); sugars, such as sucrose, trehalose; sugar alcohols, such as mannitol, sorbitol; and buffer agents, such as phosphate-based buffer systems, sodium and potassium hydrogen phosphate buffers as defined above, acetate buffer, phosphate buffer, citrate buffer, TRIS buffer, maleate buffer or succinate buffer, histidine buffer; amino acids, such as histidine, arginine and glycine.

The buffer exchange may be performed by means of routine methods, for example dialysis, diafiltration or ultrafiltration.

The initial protein concentration of the aqueous solution used as starting material should be in the range of about 0.5 to about 200 or about 1 to about 50 mg/ml.

Depending on the intended final batch size (which may be in the range of 1 ml to 20,000 liters) an initial volume of the aqueous antibody solution is placed in an appropriate container (as for example a vessel, bottle or tank) made of inert material, as for example glass, polymer or metal. The initial volume of the aqueous solution may correspond to about 30 to 80%, normally about 50% of the final batch size.

If necessary the solution after having been filled into the container will be brought to standardized conditions. In particular, the temperature will be adjusted in the range of about 4° C. and about 37° C.

Then the crystallization solution, containing the crystallization agent in an appropriate concentration, optionally preconditioned in the same way as the antibody solution, is added to the antibody solution.

The addition of the crystallization solution is performed continuously or discontinuously optionally under gentle agitation in order to facilitate mixing of the two liquids. Preferably the addition is performed under conditions where the protein solution is provided under agitation and the crystallization solution (or agents in its solid from) is/are added in a controlled manner.

The formation of the antibody crystals is initiated by applying a polyalkylene polyol as defined above, in particular a polyalkylene glycol, and preferably a polyethylene glycol (PEG), or a mixture of at least two different polyalkylene glycols as defined above as the crystallization agent. The crystallization solution contains the agent in a concentration, which is sufficient to afford a final concentration of the polyalkylene polyol in the crystallization mixture in the range of about 5 to 30% (w/v).

Preferably, the crystallization solution additionally contains an acidic buffer, e.g., different from that of the antibody solution, in a concentration suitable to allow the adjustment of the pH of the crystallization mixture in the range of about 4 to 6.

After having finished the addition of the crystallization solution, the obtained mixture may be further incubated for about 1 hour to about 250 days in order to obtain a maximum yield of antibody crystals. If appropriate, the mixture may, for example, be agitated, gently stirred, rolled or otherwise moved.

Finally, the crystals obtained may be separated by known methods, for example filtration or centrifugation, as for example by centrifugation at about 200-20,000 rpm, preferably 500-2,000 rpm, at room temperature or 4° C. The remaining mother liquor may be discarded or further processed.

If necessary, the isolated crystals may be washed and subsequently dried, or the mother liquor can be exchanged by a different solvent system suitable for storage and/or final use of the antibodies suspended therein.

Antibody crystals formed according to the present invention may vary in their shape. as already explained above For therapeutic administration, the size of the crystals will vary depending on the route of administration, for example, for subcutaneous administration the size of the crystals may be larger than for intravenous administration.

The shape of the crystals may be altered by adding specific additional additives to the crystallization mixture, as has been previously described for both protein crystals and crystals of low molecular weight organic and inorganic molecules.

If necessary, it may be verified that the crystals are in fact crystals of the antibody. Crystals of an antibody can be analyzed microscopically for birefringence. In general, crystals, unless of cubic internal symmetry, will rotate the plane of polarization of polarized light. In yet another method, crystals can be isolated, washed, resolubilized and analyzed by SDS-PAGE and, optionally, stained with an anti-Fc receptor antibody. Optionally, the resolubilized antibody can also be tested for binding to its hIL-12 utilizing standard assays.

Crystals as obtained according to the invention may also be crosslinked to one another. Such crosslinking may enhance stability of the crystals. Methods for crosslinking crystals described, for example, in U.S. Pat. No. 5,849,296. Crystals can be crosslinked using a bifunctional reagent such as glutaraldehyde. Once crosslinked, crystals can be lyophilized and stored for use, for example, in diagnostic or therapeutic applications.

In some cases, it may be desirable to dry the crystal. Crystals may be dried by means of inert gases, like nitrogen gas, vacuum oven drying, lyophilization, evaporation, tray drying, fluid bed drying, spray drying, vacuum drying or roller drying. Suitable methods are well known.

Crystals formed according to the invention can be maintained in the original crystallization solution, or they can be washed and combined with other substances, like inert carriers or ingredients to form compositions or formulations comprising crystals of the invention. Such compositions or formulations can be used, for example, in therapeutic and diagnostic applications.

A preferred embodiment is to combine a suitable carrier or ingredient with crystals of the invention in that way that crystals of the formulation are embedded or encapsulated by an excipient. Suitable carriers may be taken from the non limiting group of: poly (acrylic acid), poly (cyanoacrylates), poly (amino acids), poly (anhydrides), poly (depsipeptide), poly (esters), poly (lactic acid), poly (lactic-co-glycolic acid) or PLGA, poly (β-hydroxybutryate), poly (caprolactone), poly (dioxanone); poly (ethylene glycol), poly (hydroxypropyl) methacrylamide, poly (organo) phosphazene, poly (ortho esters), poly (vinyl alcohol), poly (vinylpyrrolidone), maleic anhydride alkyl vinyl ether copolymers, pluronic polyols, albumin, alginate, cellulose and cellulose derivatives, collagen, fibrin, gelatin, hyaluronic acid, oligosaccharides, glycaminoglycans, sulfated polysaccharides, blends and copolymers thereof, SAIB, fatty acids and salts of fatty acids, fatty alcohols, fatty amines, mono-, di-, and triglycerides of fatty acids, phospholipids, glycolipids, sterols and waxes and related similar substances. Waxes are further classified in natural and synthetic products. Natural materials include waxes obtained from vegetable, animal or minerals sources such as beeswax, carnauba or montanwax. Chlorinated naphthalenes and ethylenic polymers are examples for synthetic wax products.

C. Compositions

Another aspect of the invention relates to compositions/formulations comprising anti-hIL-12 antibody crystals in combination with at least one carrier/excipient.

The formulations may be solid, semisolid or liquid.

Formulations of the invention are prepared, in a form suitable for storage and/or for use, by mixing the antibody having the necessary degree of purity with a physiologically acceptable additive, like carrier, excipient and/or stabilizer (see for example Remington's Pharmaceutical Sciences, 16th Edn., Osol, A. Ed. (1980)), in the form of suspensions, lyophilized or dried in another way. Optionally further active ingredients, as for example different antibodies, biomolecules, chemically or enzymatically synthesized low-molecular weight molecules may be incorporated as well.

Acceptable additives are non-toxic to recipients at the dosages and concentrations employed. Nonlimiting examples thereof include:

Acidifying agents, like acetic acid, citric acid, fumaric acid, hydrochloric acid, malic acid, nitric acid, phosphoric acid, diluted phosphoric acid, sulfuric acid, tartaric acid.

Aerosol propellants, like butane, dichlorodifluoromethane, dichlorotetrafluoroethane, isobutane, propane, trichloromonofluoromethane.

Air displacements, like carbon dioxide, nitrogen;

Alcohol denaturants, like methyl isobutyl ketone, sucrose octacetate;

Alkalizing agents, like ammonia solution, ammonium carbonate, diethanolamine, diisopropanolamine, potassium hydroxide, sodium bicarbonate, sodium borate, sodium carbonate, sodium hydroxide, trolamine;

Antifoaming agents, like dimethicone, simethicone.

Antimicrobial preservatives, like benzalkonium chloride, benzalkonium chloride solution, benzelthonium chloride, benzoic acid, benzyl alcohol, butylparaben, cetylpyridinium chloride, chlorobutanol, chlorocresol, cresol, dehydroacetic acid, ethylparaben, methylparaben, methylparaben sodium, phenol, phenylethyl alcohol, phenylmercuric acetate, phenylmercuric nitrate, potassium benzoate, potassium sorbate, propylparaben, propylparaben sodium, sodium benzoate, sodium dehydroacetate, sodium propionate, sorbic acid, thimerosal, thymol.

Antioxidants, like ascorbic acid, ascorbyl palmitate, butylated hydroxyanisole, butylated hydroxytoluene, hypophosphorous acid, monothioglycerol, propyl gallate, sodium formaldehyde sulfoxylate, sodium metabisulfite, sodium thiosulfate, sulfur dioxide, tocopherol, tocopherols excipient;

Buffering agents, like acetic acid, ammonium carbonate, ammonium phosphate, boric acid, citric acid, lactic acid, phosphoric acid, potassium citrate, potassium metaphosphate, potassium phosphate monobasic, sodium acetate, sodium citrate, sodium lactate solution, dibasic sodium phosphate, monobasic sodium phosphate, histidine.

Chelating agents, like edetate disodium, ethylenediaminetetraacetic acid and salts, edetic acid;

Coating agents, like sodium carboxymethylcellulose, cellulose acetate, cellulose acetate phthalate, ethylcellulose, gelatin, pharmaceutical glaze, hydroxypropyl cellulose, hydroxypropyl methylcellulose, hydroxypropyl methylcellulose phthalate, methacrylic acid copolymer, methylcellulose, polyethylene glycol, polyvinyl acetate phthalate, shellac, sucrose, titanium dioxide, carnauba wax, microcrystalline wax, zein, poly amino acids, other polymers like PLGA etc., and SAIB.

Coloring agents, like ferric oxide.

Complexing agents, like ethylenediaminetetraacetic acid and salts (EDTA), edetic acid, gentisic acid ethanolamide, oxyquinoline sulfate.

Desiccants, like calcium chloride, calcium sulfate, silicon dioxide.

Emulsifying and/or solubilizing agents, like acacia, cholesterol, diethanolamine (adjunct), glyceryl monostearate, lanolin alcohols, lecithin, mono- and di-glycerides, monoethanolamine (adjunct), oleic acid (adjunct), oleyl alcohol (stabilizer), poloxamer, polyoxyethylene 50 stearate, polyoxyl 35 caster oil, polyoxyl 40 hydrogenated castor oil, polyoxyl 10 oleyl ether, polyoxyl 20 cetostearyl ether, polyoxyl 40 stearate, polysorbate 20, polysorbate 40, polysorbate 60, polysorbate 80, propylene glycol diacetate, propylene glycol monostearate, sodium lauryl sulfate, sodium stearate, sorbitan monolaurate, soritan monooleate, sorbitan monopalmitate, sorbitan monostearate, stearic acid, trolamine, emulsifying wax.

Filtering aids, like powdered cellulose, purified siliceous earth.

Flavors and perfumes, like anethole, benzaldehyde, ethyl vanillin, menthol, methyl salicylate, monosodium glutamate, orange flower oil, peppermint, peppermint oil, peppermint spirit, rose oil, stronger rose water, thymol, tolu balsam tincture, vanilla, vanilla tincture, vanillin.

Glidant and/or anticaking agents, like calcium silicate, magnesium silicate, colloidal silicon dioxide, talc.

Humectants, like glycerin, hexylene glycol, propylene glycol, sorbitol;

Ointment bases, like lanolin, anhydrous lanolin, hydrophilic ointment, white ointment, yellow ointment, polyethylene glycol ointment, petrolatum, hydrophilic petrolatum, white petrolatum, rose water ointment, squalane.

Plasticizers, like castor oil, lanolin, mineral oil, petrolatum, benzyl benzyl formate, chlorobutanol, diethyl pthalate, sorbitol, diacetylated monoglycerides, diethyl phthalate, glycerin, glycerol, mono- and di-acetylated monoglycerides, polyethylene glycol, propylene glycol, triacetin, triethyl citrate, ethanol.

Polypeptides, like low molecular weight (less than about 10 residues);

Proteins, such as serum albumin, gelatin, or immunoglobulins;

Polymer membranes, like cellulose acetate membranes.

Solvents, like acetone, alcohol, diluted alcohol, amylene hydrate, benzyl benzoate, butyl alcohol, carbon tetrachloride, chloroform, corn oil, cottonseed oil, ethyl acetate, glycerin, hexylene glycol, isopropyl alcohol, methyl alcohol, methylene chloride, methyl isobutyl ketone, mineral oil, peanut oil, polyethylene glycol, propylene carbonate, propylene glycol, sesame oil, water for injection, sterile water for injection, sterile water for irrigation, purified water, liquid triglycerides, liquid waxes, higher alcohols.

Sorbents, like powdered cellulose, charcoal, purified siliceous earth, Carbon dioxide sorbents, barium hydroxide lime, soda lime.

Stiffening agents, like hydrogenated castor oil, cetostearyl alcohol, cetyl alcohol, cetyl esters wax, hard fat, paraffin, polyethylene excipient, stearyl alcohol, emulsifying wax, white wax, yellow wax.

Suppository bases, like cocoa butter, hard fat, polyethylene glycol;

Suspending and/or viscosity-increasing agents, like acacia, agar, alginic acid, aluminum monostearate, bentonite, purified bentonite, magma bentonite, carbomer 934p, carboxymethylcellulose calcium, carboxymethylcellulose sodium, carboxymethylcellulose sodium 12, carrageenan, microcrystalline and carboxymethylcellulose sodium cellulose, dextrin, gelatin, guar gum, hydroxyethyl cellulose, hydroxypropyl cellulose, hydroxypropyl methylcellulose, magnesium aluminum silicate, methylcellulose, pectin, polyethylene oxide, polyvinyl alcohol, povidone, propylene glycol alginate, silicon dioxide, colloidal silicon dioxide, sodium alginate, tragacanth, xanthan gum;

Sweetening agents, like aspartame, dextrates, dextrose, excipient dextrose, fructose, mannitol, saccharin, calcium saccharin, sodium saccharin, sorbitol, solution sorbitol, sucrose, compressible sugar, confectioners sugar, syrup;

Tablet binders, like acacia, alginic acid, sodium carboxymethylcellulose, microcrystalline cellulose, dextrin, ethylcellulose, gelatin, liquid glucose, guar gum, hydroxypropyl methylcellulose, methylcellulose, polyethylene oxide, povidone, pregelatinized starch, syrup.

Tablet and/or capsule diluents, like calcium carbonate, dibasic calcium phosphate, tribasic calcium phosphate, calcium sulfate, microcrystalline cellulose, powdered cellulose, dextrates, dextrin, dextrose excipient, fructose, kaolin, lactose, mannitol, sorbitol, starch, pregelatinized starch, sucrose, compressible sugar, confectioner's sugar;

Tablet disintegrants, like alginic acid, microcrystalline cellulose, croscarmellose sodium, corspovidone, polacrilin potassium, sodium starch glycolate, starch, pregelatinized starch.

Tablet and/or capsule lubricants, like calcium stearate, glyceryl behenate, magnesium stearate, light mineral oil, polyethylene glycol, sodium stearyl fumarate, stearic acid, purified stearic acid, talc, hydrogenated vegetable oil, zinc stearate;

Tonicity agent, like dextrose, glycerin, mannitol, potassium chloride, sodium chloride Vehicle: flavored and/or sweetened aromatic elixir, compound benzaldehyde elixir, iso-alcoholic elixir, peppermint water, sorbitol solution, syrup, tolu balsam syrup.

Vehicles, like oleaginous almond oil, corn oil, cottonseed oil, ethyl oleate, isopropyl myristate, isopropyl palmitate, mineral oil, light mineral oil, myristyl alcohol, octyldodecanol, olive oil, peanut oil, persic oil, sesame oil, soybean oil, squalane; solid carrier sugar spheres; sterile bacteriostatic water for injection, bacteriostatic sodium chloride injection, liquid triglycerides, liquid waxes, higher alcohols Water repelling agents, like cyclomethicone, dimethicone, simethicone;

Wetting and/or solubilizing agents, like benzalkonium chloride, benzethonium chloride, cetylpyridinium chloride, docusate sodium, nonoxynol 9, nonoxynol 10, octoxynol 9, poloxamer, polyoxyl 35 castor oil, polyoxyl 40, hydrogenated castor oil, polyoxyl 50 stearate, polyoxyl 10 oleyl ether, polyoxyl 20, cetostearyl ether, polyoxyl 40 stearate, polysorbate 20, polysorbate 40, polysorbate 60, polysorbate 80, sodium lauryl sulfate, sorbitan monolaureate, sorbitan monooleate, sorbitan monopalmitate, sorbitan monostearate, and tyloxapol.

The crystals may be combined with a polymeric carrier to provide for stability and/or sustained release. Such polymers include biocompatible and biodegradable polymers. A polymeric carrier may be a single polymer type or it may be composed of a mixture of polymer types. Nonlimiting examples of polymeric carriers have already been stated above.

Examples of preferred ingredients or excipients include:

salts of amino acids such as glycine, arginine, aspartic acid, glutamic acid, lysine, asparagine, glutamine, proline, histidine;

monosaccharides, such as glucose, fructose, galactose, mannose, arabinose, xylose, ribose;

disaccharides, such as lactose, trehalose, maltose, sucrose;

polysaccharides, such as maltodextrins, dextrans, starch, glycogen;

alditols, such as mannitol, xylitol, lactitol, sorbitol;

glucuronic acid, galacturonic acid;

cyclodextrins, such as methyl cyclodextrin, hydroxypropyl-(3-cyclodextrin)

inorganic salts, such as sodium chloride, potassium chloride, magnesium chloride, phosphates of sodium and potassium, boric acid ammonium carbonate and ammonium phosphate;

organic salts, such as acetates, citrate, ascorbate, lactate;

emulsifying or solubilizing agents like acacia, diethanolamine, glyceryl monostearate, lecithin, monoethanolamine, oleic acid, oleyl alcohol, poloxamer, polysorbates, sodium lauryl sulfate, stearic acid, sorbitan monolaurate, sorbitan monostearate, and other sorbitan derivatives, polyoxyl derivatives, wax, polyoxyethylene derivatives, sorbitan derivatives; and viscosity increasing reagents like, agar, alginic acid and its salts, guar gum, pectin, polyvinyl alcohol, polyethylene oxide, cellulose and its derivatives propylene carbonate, polyethylene glycol, hexylene glycol and tyloxapol.

Formulations described herein also comprise an effective amount of crystalline antibody. In particular, the formulations of the invention may include a "therapeutically effective amount" or a "prophylactically effective amount" of antibody crystals of the invention. A "therapeutically effective amount" refers to an amount effective, at dosages and for periods of time necessary, to achieve the desired therapeutic result. A "therapeutically effective amount" of the antibody crystals may vary according to factors such as the disease state, age, sex, and weight of the individual, and the ability of the antibody to elicit a desired response in the individual. A therapeutically effective amount is also one in which any toxic or detrimental effects of the antibody are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Suitable dosages can readily be determined using standard methodology. The antibody is suitably administered to the patient at one time or over a series of treatments. Depending on the above mentioned factors, about 1 µg/kg to about 50 mg/kg, as for example 0.1-20 mg/kg of antibody is an initial candidate dosage for administration to the patient, whether, for example, by one or more separate administrations, or by continuous infusion. A typical daily or weekly dosage might range from about 1 µg/kg to about 20 mg/kg or more, depending on the condition, the treatment is repeated until a desired suppression of disease symptoms occurs. However, other dosage regimens may be useful. In some cases, formulations comprise a concentration of antibody of at least about 1 g/L or greater when resolubilized. In other embodiments, the antibody concentration is at least about 1 g/L to about 100 g/L when resolubilized.

Crystals of an antibody, or formulations comprising such crystals, may be administered alone or as part of a pharmaceutical preparation. They may be administered by parenteral, oral or topical routes. For example, they may be administered by oral, pulmonary, nasal, aural, anal, dermal, ocular, intravenous, intramuscular, intraarterial, intraperitoneal, mucosal, sublingual, subcutaneous, transdermal, topical or intracranial routes, or into the buccal cavity. Specific examples of administration techniques comprise pulmonary inhalation, intralesional application, needle injection, dry powder inhalation, skin electroporation, aerosol delivery, and needle-free injection technologies, including needle-free subcutaneous administration.

The present invention will now be explained in more detail by means of the following, non-limiting, illustrative examples. Guided by the general part of the description and on the basis of his general knowledge a skilled reader will be enabled to provide further embodiments to the invention without undue experimentation.

EXEMPLIFICATION

A. Materials a) Protein

Frozen monoclonal antibody (mAb) ABT-874 was obtained from Abbott Laboratories. All experiments were performed from a product lot, where the original mAb concentration was 64 mg/mL.

b) Fine Chemicals

Sodium acetate was obtained from Grassing GmbH, Filsum. Polyethylene glycols of different polymerization grades were obtained from Clariant GmbH, Sulzbach. Furthermore, commercial crystallization screens and reagents (Hampton Research, Nextal Biotechnologies) were used for certain microscale experiments. All other chemicals were from Sigma-Aldrich, Steinheim, or Merck, Darmstadt.

B. General Methods a) Thawing of ABT-874 Drug Substance

ABT-874 was thawed at 25° C. in agitated water baths.

b) Buffer Exchange—Method A

An aliquot of ABT-874 solution was pipetted into a 30 KDa MWCO Vivaspin 20 concentrator (Vivascience). The protein sample was diluted with the new buffer in a ratio of 1:10, and by centrifugation at 5,000×g at 4° C. (Sigma 4 K 15 lab centrifuge) the sample volume was brought back to the original sample volume. The dilution/centrifugation steps were repeated once, resulting in a dilution of 1:100 of the original sample buffer. After adjustment of protein concentration, the solution was sterile filtered through a 0.2 µm syringe driven filter unit.

b) Buffer Exchange—Method B

An aliquot of ABT-874 solution was placed into a SLIDE-A-LYZER dialysis cassette (Pierce Biotechnology Inc.). The dialysis cassette was placed into a beaker containing the buffer of choice, and the buffer exchange was performed at 4° C. overnight with stirring. After adjustment of protein concentration, the solution was sterile filtered through a 0.2 µm syringe driven filter unit.

c) OD280—Protein Concentration Measurements

A ThermoSpectronics UV1 device was used to assess protein concentration at a wavelength of 280 nm, applying an extinction coefficient of 1.42 $cm^2$ $mg^{-1}$. For this purpose, aliquots of crystallization slurries were centrifuged at 14,000 rpm, and residual protein concentration was determined in the supernatant.

d) pH Measurements pH measurements were conducted by using a Mettler Toledo MP220 pH meter. Inlab 413 electrodes and Inlab 423 microelectrodes were utilized.

e) Crystallization Methods e1) Microscale Crystallization—Sitting Drop Vapor Diffusion Hydra II Initial crystallization screens were performed using a Hydra II crystallization robot and Greiner 96 well plates (three drop wells, Hampton Research). After setting up the plates, the wells were sealed with Clearseal film (Hampton Research).

e2) Microscale Crystallization—Hanging Drop Vapor Diffusion

Hanging drop vapor diffusion experiments were conducted using VDX plates (with sealant, Hampton Research) and OptiClear plastic cover slides (squares, Hampton Research) or siliconized glass cover slides (circle, Hampton Research), respectively. After preparation of reservoir solutions, one drop of reservoir solution was admixed with one drop of the protein solution on a cover slide, and the well was sealed with the inverted cover slide in such a way that the drop was hanging above the reservoir.

e3) Batch Crystallization—Method A (24 Well Plate)

Batch crystallization was performed by admixing the protein solution with an equal amount of crystallization buffer (500 µl) in a well. The well was subsequently sealed with adhesive tape to prevent water evaporation.

e4) Batch Crystallization—Method B (Eppendorff Reaction Tube)

Batch crystallization was performed by admixing the protein solution with an equal amount of crystallization buffer in a 1.5 mL or a 2 mL Eppendorff reaction tube.

e5) Batch Crystallization—Method C (Falcon Tubes, No Agitation)

Batch crystallization was performed by admixing the protein solution with an equal amount of crystallization buffer in a 15 mL or 50 mL Falcon tube.

e6) Batch Crystallization—Method D (Falcon Tubes, Agitation)

Batch crystallization was performed by admixing the protein solution with an equal amount of crystallization buffer in a 15 mL or 50 mL Falcon tube. Right after closing, the tube was put on a laboratory shaker (GFL 3013 or GFL 3015) or was alternatively agitated by tumbling. By application of these methods, introduction of stirrers into the sample was avoided.

f) SDS-PAGE

Samples were prepared by adjusting protein concentration to 8 µg/20 µL. The samples were diluted with an SDS/Tris/glycerine buffer containing bromophenol blue. Qualitative SDS PAGE analysis was performed using Invitrogen NuPage 10% Bis-Tris Gels, NuPage MES SDS Running Buffer and Mark12 Wide Range Protein Standards. 20 µL of sample was pipetted into a gel pocket. After running the gel and fixation with acetic acid/methanol reagent, staining was performed using the Novex Colloidal Blue Stain Kit. Gels were dried using Invitrogen Gel-Dry drying solution.

g) Light Microscopy

Crystals were observed using a Zeiss Axiovert 25 or a Nikon Labophot microscope. The latter was equipped with a polarization filter set and a JVC TK C1380 color video camera.

h) SE-HPLC

Aggregation levels of ABT-874 samples were assessed by SE-HPLC. A Dionex P680 pump, ASI-100 autosampler and UVD170U detector device were used. Aggregated species were separated from the monomer by an Amersham Bioscience Superdex 200 10/300 GL gel filtration column, applying a validated Abbott standard protocol (A-796874.0—ABT 874, J 695).

C. Vapor Diffusion Crystallization Experiments

Concentration values given in the following examples are initial values referring to the antibody solution and the reservoir solution before mixing of the two solutions.

All pH values, if not described otherwise, refer to the pH of an acetate buffer stock before it was combined with other substances, like the crystallization agent.

All buffer molarities, if not described otherwise, refer to sodium acetate concentrations in a stock solution before pH adjustment, typically performed using acetic acid glacial.

Example 1

PEG 4,000/Sodium Acetate Grid Screen in Hanging Drop Vapor Diffusion Mode

A hanging drop vapor diffusion crystallization method was performed on ABT-874. ABT-874 was buffered into a buffer containing about 0.1M sodium acetate at a pH of about 5.2. The protein concentration was adjusted to 10 mg/mL.

A greased VDX plate and square OptiClear plastic cover slides were used. 500 µL of a particular reservoir solution was prepared by admixing acetate buffer, 50% w/v PEG 4,000 solution and Milli Q water (fully desalted and optionally pre-distilled) in each well. In this example, the acetate buffer molarity was kept constant at about 0.1M, and PEG 4,000 was varied from about 6% w/v to about 28% w/v in 2% steps. The pH was about 5.2 throughout. Each condition was assessed in duplicate. About 1 µL of the protein solution was admixed with about 1 µL of a particular reservoir solution on a square OptiClear plastic cover slide, and the well was sealed with the inverted slide, generating a hanging drop experiment. The plates were stored at ambient temperature. Microscopy of the drops was performed multiple times during the following thirty days. The conditions were classified into clear drops, drops containing random precipitation, drops containing crystals and drops containing mixtures of precipitated species and crystals.

Results:

From the 24 wells assessed, no crystals were observed.

Example 2

PEG 4,000/Sodium Acetate Grid Screen in Hanging Drop Vapor Diffusion Mode, Different Protein Concentration A hanging drop vapor diffusion crystallization method was performed on ABT-874 at different protein concentration. ABT-874 was buffered into a buffer containing about 0.1M sodium acetate at a pH of about 5.2. The protein concentration was adjusted to 50 mg/mL.

A greased VDX plate and square OptiClear plastic cover slides were used. 500 µL of a particular reservoir solution was prepared by admixing acetate buffer, 50% w/v PEG 4,000 solution and Milli Q water in each well. In this example, the acetate buffer molarity was kept constant at about 0.1M, and PEG 4,000 was varied from about 6% w/v to about 28% w/v in 2% steps. The pH was about 5.2 throughout. Each condition was assessed in duplicate. About 1 µL of the protein solution was admixed with about 1 µL of a particular reservoir solution on a square OptiClear plastic cover slide, and the well was sealed with the inverted slide, generating a hanging drop experiment. The plates were stored at ambient temperature. Microscopy of the drops was performed multiple times during the following thirty days. The conditions were classified into clear drops, drops containing random precipitation, drops containing crystals and drops containing mixtures of precipitated species and crystals.

Results:

From the 24 wells assessed, crystals were observed at a PEG 4,000 concentration of about 16%. The crystals showed needle or needle cluster like morphology.

Example 3

PEG 400/Sodium Acetate Grid Screen in Hanging Drop Vapor Diffusion Mode

A hanging drop vapor diffusion crystallization method was performed on ABT-874 using PEG 400. ABT-874 was buffered into a buffer containing about 0.1M sodium acetate at a pH of about 5.2. The protein concentration was adjusted to 10 mg/mL.

A greased VDX plate and square OptiClear plastic cover slides were used. 500 µL of a particular reservoir solution was prepared by admixing acetate buffer, 50% w/v PEG use PEG 400 solution and Milli Q water in each well. In this example, the acetate buffer molarity was kept constant at about 0.1M, and PEG 400 was varied from about 30% w/v to about 40% w/v in 2% steps. The pH was about 5.2 throughout. Each condition was assessed in duplicate. About 1 μL of the protein solution was admixed with about 1 μL of a particular reservoir solution on a square OptiClear plastic cover slide, and the well was sealed with the inverted slide, generating a hanging drop experiment. The plates were stored at ambient temperature. Microscopy of the drops was performed multiple times during the following thirty days. The conditions were classified into clear drops, drops containing random precipitation, drops containing crystals and drops containing mixtures of precipitated species and crystals.

Results:
From the 12 wells assessed, no crystals were observed.

Example 4

PEG 400/Sodium Acetate Grid Screen in Hanging Drop Vapor Diffusion Mode, Different Protein Concentration A hanging drop vapor diffusion crystallization method was performed on ABT-874 at different protein concentration. ABT-874 was buffered into a buffer containing about 0.1M sodium acetate at a pH of about 5.2. The protein concentration was adjusted to 50 mg/mL.

A greased VDX plate and square OptiClear plastic cover slides were used. 500 μL of a particular reservoir solution was prepared by admixing acetate buffer, 50% w/v PEG use PEG 400 solution and Milli Q water in each well. In this example, the acetate buffer molarity was kept constant at about 0.1M, and PEG 400 was varied from about 30% w/v to about 40% w/v in 2% steps. The pH was about 5.2 throughout. Each condition was assessed in duplicate. About 1 μL of the protein solution was admixed with about 1 μL of a particular reservoir solution on a square OptiClear plastic cover slide, and the well was sealed with the inverted slide, generating a hanging drop experiment. The plates were stored at ambient temperature. Microscopy of the drops was performed multiple times during the following thirty days. The conditions were classified into clear drops, drops containing random precipitation, drops containing crystals and drops containing mixtures of precipitated species and crystals.

Results:
From the 12 wells assessed, no crystals were observed.

Example 5

PEG 400/Sodium Acetate Grid Screen in Hanging Drop Vapor Diffusion Mode, Different Protein Concentration and Set Up A hanging drop vapor diffusion crystallization method was performed on ABT-874 using different protein concentration and a different set up. ABT-874 was buffered into a buffer containing about 0.1M sodium acetate at a pH of about 5.2. The protein concentration was adjusted to 50 mg/mL.

A greased VDX plate and square OptiClear plastic cover slides were used. 500 μL of a particular reservoir solution was prepared by admixing acetate buffer, 50% w/v PEG 400 solution and Milli Q water in each well. In this example, the acetate buffer molarity was kept constant at about 0.1M, and PEG 400 was varied from about 30% w/v to about 40% w/v in 2% steps. The pH was about 5.7 or 6.7, respectively. Each condition was assessed in duplicate. About 1 μL of the protein solution was admixed with about 1 μL of a particular reservoir solution on a square OptiClear plastic cover slide, and the well was sealed with the inverted slide, generating a hanging drop experiment. The plates were stored at ambient temperature. Microscopy of the drops was performed multiple times during the following twenty-one days. The conditions were classified into clear drops, drops containing random precipitation, drops containing crystals and drops containing mixtures of precipitated species and crystals.

Results:
From the 24 wells assessed, no crystals were observed.

Example 6

PEG 10,000/Sodium Acetate Grid Screen in Hanging Drop Vapor Diffusion Mode

A hanging drop vapor diffusion crystallization method was performed on ABT-874 using PEG 10,000. ABT-874 was buffered into a buffer containing about 0.1M sodium acetate at a pH of about 5.2. The protein concentration was adjusted to 10 mg/mL.

A greased VDX plate and square OptiClear plastic cover slides were used. 500 μL of a particular reservoir solution was prepared by admixing acetate buffer, 50% w/v PEG 10,000 solution and Milli Q water in each well. In this example, the acetate buffer molarity was kept constant at about 0.1M, and PEG 10,000 was varied from about 4% w/v to about 14% w/v in 2% steps. The pH was about 5.2 throughout. Each condition was assessed in duplicate. About 1 μL of the protein solution was admixed with about 1 μL of a particular reservoir solution on a square OptiClear plastic cover slide, and the well was sealed with the inverted slide, generating a hanging drop experiment. The plates were stored at ambient temperature. Microscopy of the drops was performed multiple times during the following thirty days. The conditions were classified into clear drops, drops containing random precipitation, drops containing crystals and drops containing mixtures of precipitated species and crystals.

Results:
From the 12 wells assessed, no crystals were observed.

Example 7

PEG 10,000/Sodium Acetate Grid Screen in Hanging Drop Vapor Diffusion Mode, Different Protein Concentration A hanging drop vapor diffusion crystallization method was performed on ABT-874 using PEG 10,000 and at different protein concentration. ABT-874 was buffered into a buffer containing about 0.1M sodium acetate at a pH of about 5.2. The protein concentration was adjusted to 50 mg/mL.

A greased VDX plate and square OptiClear plastic cover slides were used. 500 μL of a particular reservoir solution was prepared by admixing acetate buffer, 50% w/v PEG 10,000 solution and Milli Q water in each well. In this example, the acetate buffer molarity was kept constant at about 0.1M, and PEG 10,000 was varied from about 4% w/v to about 14% w/v in 2% steps. The pH was about 5.2 throughout. Each condition was assessed in duplicate. About 1 μL of the protein solution was admixed with about 1 μL of a particular reservoir solution on a square OptiClear plastic cover slide, and the well was sealed with the inverted slide, generating a hanging drop experiment. The plates were stored at ambient temperature. Microscopy of the drops was performed multiple times during the following thirty days. The conditions were classified into clear drops, drops containing random precipitation, drops containing crystals and drops containing mixtures of precipitated species and crystals.

Results:
From the 12 wells assessed, no crystals were observed.

Example 8

PEG 4,000/Sodium Acetate Grid Screen In Hanging Drop Vapor Diffusion Mode, Different Set Up A hanging drop vapor diffusion crystallization method was performed on ABT-874 using PEG 4,000 and a different set up. ABT-874 was buffered into a buffer containing about 0.1M sodium acetate at a pH of about 5.2. The protein concentration was adjusted to 10 mg/mL.

A greased VDX plate and square OptiClear plastic cover slides were used. 500 μL of a particular reservoir solution was prepared by admixing acetate buffer, 50% w/v PEG 4,000 solution and Milli Q water in each well. In this example, the acetate buffer molarity was kept constant at about 0.1M, and PEG 4,000 was varied from about 22% w/v to about 28% w/v in 2% steps. The pH was about 4.2, 4.7, 5.2, 5.7, 6.2 and 6.7, respectively. Each condition was assessed in duplicate. About 1 μL of the protein solution was admixed with about 1 μL of a particular reservoir solution on a square OptiClear plastic cover slide, and the well was sealed with the inverted slide, generating a hanging drop experiment. The plates were stored at ambient temperature. Microscopy of the drops was performed multiple times during the following thirty days. The conditions were classified into clear drops, drops containing random precipitation, drops containing crystals and drops containing mixtures of precipitated species and crystals.

Results:
From the 48 wells assessed, no crystals were observed.

Example 9

PEG 4,000/Sodium Acetate Grid Screen in Hanging Drop Vapor Diffusion Mode, Different Set Up A hanging drop vapor diffusion crystallization method was performed on ABT-874 using PEG 4,000 and another set up. ABT-874 was buffered into a buffer containing about 0.1M sodium acetate at a pH of about 5.2. The protein concentration was adjusted to 10 mg/mL.

A greased VDX plate and square OptiClear plastic cover slides were used. 500 μL of a particular reservoir solution was prepared by admixing acetate buffer, 50% w/v PEG 4,000 solution and Milli Q water in each well. In this example, the acetate buffer molarity was kept constant at about 0.1M, and PEG 4,000 was varied from about 8% w/v to about 14% w/v in 2% steps. The pH was about 5.7, 6.2 and 6.7, respectively. Each condition was assessed in duplicate. About 1 μL of the protein solution was admixed with about 1 μL of a particular reservoir solution on a square OptiClear plastic cover slide, and the well was sealed with the inverted slide, generating a hanging drop experiment. The plates were stored at ambient temperature. Microscopy of the drops was performed multiple times during the following thirty days. The conditions were classified into clear drops, drops containing random precipitation, drops containing crystals and drops containing mixtures of precipitated species and crystals.

Results:
From the 24 wells assessed, crystals were observed at a PEG 4,000 concentration of about 10 to 14% at all pH included in this example. The crystals showed needle or needle cluster like morphology.

Example 10

PEG 400 Combined with 4,000/Sodium Acetate Grid Screen in Hanging Drop Vapor Diffusion Mode A hanging drop vapor diffusion crystallization method was performed on ABT-874 using PEG 400 with 4,000/Sodium Acetate. ABT-874 was buffered into a buffer containing about 0.1M sodium acetate at a pH of about 5.2. The protein concentration was adjusted to 10 mg/mL.

A greased VDX plate and square OptiClear plastic cover slides were used. 500 μL of a particular reservoir solution was prepared by admixing acetate buffer, 50% w/v PEG 4,000 solution and Milli Q water in each well. In this example, the acetate buffer molarity was kept constant at about 0.1M, and PEG 4,000 was varied from about 8% w/v to about 12% w/v in 2% steps. Simultaneously, PEG 400 was brought into the PEG 4,000/acetate solutions at concentrations of about 26% w/v, 28% w/v, 30% w/v and 32% w/v, respectively. The pH was about 5.2 throughout. Each condition was assessed in duplicate. About 1 μL of the protein solution was admixed with about 1 μL of a particular reservoir solution on a square OptiClear plastic cover slide, and the well was sealed with the inverted slide, generating a hanging drop experiment. The plates were stored at ambient temperature. Microscopy of the drops was performed multiple times during the following thirty days. The conditions were classified into clear drops, drops containing random precipitation, drops containing crystals and drops containing mixtures of precipitated species and crystals.

Results:
From the 24 wells assessed, no crystals were observed.

Example 11

PEG 400 Combined with 4,000/Sodium Acetate Grid Screen in Hanging Drop Vapor Diffusion Mode, Different Protein Concentration A hanging drop vapor diffusion crystallization method was performed on ABT-874 using PEG 400 with 4,000/Sodium Acetate with different protein concentrations. ABT-874 was buffered into a buffer containing about 0.1M sodium acetate at a pH of about 5.2. The protein concentration was adjusted to 50 mg/mL.

A greased VDX plate and square OptiClear plastic cover slides were used. 500 μL of a particular reservoir solution was prepared by admixing acetate buffer, 50% w/v PEG 4,000 solution and Milli Q water in each well. In this example, the acetate buffer molarity was kept constant at about 0.1M, and PEG 4,000 was varied from about 4% w/v to about 8% w/v in 2% steps. Simultaneously, PEG 400 was brought into the PEG 4,000/acetate solutions and concentrations of about 30% w/v, 32% w/v, 34% w/v and 36% w/v, respectively. The pH was about 5.2 throughout. Each condition was assessed in duplicate. About 1 μL of the protein solution was admixed with about 1 μL of a particular reservoir solution on a square OptiClear plastic cover slide, and the well was sealed with the inverted slide, generating a hanging drop experiment. The plates were stored at ambient temperature. Microscopy of the drops was performed multiple times during the following thirty days. The conditions were classified into clear drops, drops containing random precipitation, drops containing crystals and drops containing mixtures of precipitated species and crystals.

Results:
From the 24 wells assessed, no crystals were observed.

Example 12

PEG 4,000/Sodium Acetate Grid Screen in Hanging Drop Vapor Diffusion Mode, Different Protein Buffer

A hanging drop vapor diffusion crystallization method was performed on ABT-874 using PEG 4,000 with different protein buffers. ABT-874 was buffered into a buffer containing about 0.1M sodium acetate at a pH of about 5.5. The protein concentration was adjusted to 10 mg/mL.

A greased VDX plate and square OptiClear plastic cover slides were used. 500 µL of a particular reservoir solution was prepared by admixing acetate buffer, 50% w/v PEG 4,000 solution and Milli Q water in each well. In this example, the acetate buffer molarity was kept constant at about 0.1M, and PEG 4,000 was varied from about 4% w/v to about 26% w/v in 2% steps. The pH was 5.5 throughout. Each condition was assessed in duplicate. About 1 µL of the protein solution was admixed with about 1 µL of a particular reservoir solution on a square OptiClear plastic cover slide, and the well was sealed with the inverted slide, generating a hanging drop experiment. The plates were stored at ambient temperature. Microscopy of the drops was performed multiple times during the following five days. The conditions were classified into clear drops, drops containing random precipitation, drops containing crystals and drops containing mixtures of precipitated species and crystals.

Results:
From the 24 wells assessed, crystals were observed at a PEG 4,000 concentration of about 12% w/v, 18% w/v, 20% w/v, 22% w/v and 24% w/v, respectively. The crystals showed needle or needle cluster like morphology.

Example 13

PEG 4,000/Sodium Acetate Grid Screen in Hanging Drop Vapor Diffusion Mode, Different Protein Concentration

A hanging drop vapor diffusion crystallization method was performed on ABT-874 using PEG 4,000 with different protein concentrations. ABT-874 was buffered into a buffer containing about 0.1M sodium acetate at a pH of about 5.5. The protein concentration was adjusted to 5 mg/mL.

A greased VDX plate and square OptiClear plastic cover slides were used. 500 µL of a particular reservoir solution was prepared by admixing acetate buffer, 50% w/v PEG 4,000 solution and Milli Q water in each well. In this example, the acetate buffer molarity was kept constant at about 0.1M, and PEG 4,000 was varied from about 4% w/v to about 26% w/v in 2% steps. The pH was 5.5 throughout. Each condition was assessed in duplicate. About 1 µL of the protein solution was admixed with about 1 µL of a particular reservoir solution on a square OptiClear plastic cover slide, and the well was sealed with the inverted slide, generating a hanging drop experiment. The plates were stored at ambient temperature. Microscopy of the drops was performed multiple times during the following five days. The conditions were classified into clear drops, drops containing random precipitation, drops containing crystals and drops containing mixtures of precipitated species and crystals.

Results:
From the 24 wells assessed, crystals were observed at a PEG 4,000 concentration of about 10% w/v and 14% w/v, respectively. The crystals showed needle or needle cluster like morphology.

Example 14

PEG 4,000/Sodium Acetate Grid Screen in Hanging Drop Vapor Diffusion Mode, Different Protein Buffer

A hanging drop vapor diffusion crystallization method was performed on ABT-874 using PEG 4,000/Sodium Acetate with different protein buffer. ABT-874 was buffered into a buffer containing about 0.1M sodium acetate at a pH of about 5.5. The protein concentration was adjusted to 20 mg/mL.

A greased VDX plate and square OptiClear plastic cover slides were used. 500 µL of a particular reservoir solution was prepared by admixing acetate buffer, 50% w/v PEG 4,000 solution and Milli Q water in each well. In this example, the acetate buffer molarity was kept constant at about 0.1M, and PEG 4,000 was varied from about 4% w/v to about 26% w/v in 2% steps. The pH was 5.5 throughout. Each condition was assessed in duplicate. About 1 µL of the protein solution was admixed with about 1 µL of a particular reservoir solution on a square OptiClear plastic cover slide, and the well was sealed with the inverted slide, generating a hanging drop experiment. The plates were stored at ambient temperature. Microscopy of the drops was performed multiple times during the following five days. The conditions were classified into clear drops, drops containing random precipitation, drops containing crystals and drops containing mixtures of precipitated species and crystals.

Results:
From the 24 wells assessed, crystals were observed at a PEG 4,000 concentration of about 10% w/v, 14% w/v, 16% w/v, 20% w/v and 22% w/v, respectively. The crystals showed needle or needle cluster like morphology.

Example 15

Broad Screening of Conditions in Vapor Diffusion Mode

A broad screening hanging drop vapor diffusion crystallization method was performed on ABT-874. ABT-874 was buffered into a 20 mM HEPES/150 mM sodium chloride buffer at pH 7.4. The protein concentration was adjusted to 10 mg/mL. In another case, protein concentration was adjusted to 5 mg/mL. In another case, protein concentration was adjusted to 20 mg/mL.

Using the Hydra II crystallization roboter, 96 well Greiner plates were set up at ambient temperature, using several commercially available crystallization screens. The protein solution and the crystallization agent were admixed in a ratio of about 1:1, preferably 1:1.

The following screens were used. Hampton Crystal Screen 1 & 2, Hampton Index Screen, Hampton SaltRX Screen (all from Hampton Research), Nextal The Classics, The Classics Lite, The PEGs, The Anions, The pH clear and The Ammonium sulphate (all from Nextal Biotechnologies).

After addition of the protein to the crystallization agent (three drops per condition, containing the three different protein concentrations as described above), the plates were sealed with Clearseal film. Any plate was set up in quadruplicate and stored at ambient temperature, 4° C., 27° C. and 37° C., respectively. Microscopy of the drops was performed after six days. The conditions were classified into clear drops, drops containing random precipitation, drops containing crystals and drops containing mixtures of precipitated species and crystals.

Results:

From the 10,368 conditions tested, 4 rendered crystals. The conditions comprised following protein concentrations and crystallization agents as declared by the manufacturers:

ambient temperature, ABT-874 at about 20 mg/mL
0.2M ammonium sulphate, 30% w/v PEG 8,000
(Hampton Crystal Screen, C6)
4° C., ABT-874 at about 5 mg/mL
0.1M HEPES pH 7.5, 5% w/v PEG 8,000
(Nextal The Classics Lite, F4)
4° C., ABT-874 at about 10 mg/mL
0.1M HEPES pH 7.5, 5% w/v PEG 6,000, 2.5% v/v MPD
(Nextal The Classics Lite, H9)
4° C., ABT-874 at about 20 mg/mL
0.1M HEPES, 5% w/v PEG 6,000, pH 7.00
(Nextal pH clear, C4)

The crystals showed needle like or needle cluster like morphologies.

Example 16

PEG 4,000/Sodium Acetate Grid Screen in Hanging Drop Vapor Diffusion Mode, Different Set Up A hanging drop vapor diffusion crystallization method was performed on ABT-874 using PEG 400 with 4,000/Sodium Acetate with a different set up. ABT-874 was buffered into a 20 mM HEPES/150 mM sodium chloride buffer at pH 7.4. The protein concentration was adjusted to 10 mg/mL. In another case, protein concentration was adjusted to 5 mg/mL.

A greased VDX plate and circle siliconized glass cover slides were used. 500 μL of a particular reservoir solution was prepared by admixing acetate buffer, 50% w/v PEG 4,000 solution and Milli Q water in each well. In this example, the acetate buffer molarity was kept constant at about 0.1M, and PEG 4,000 concentration was used at about 12% w/v, 18% w/v, 24% w/v and 30% w/v, respectively. The pH was varied from about 3.6 to about 5.6 in 0.2 steps, generating 48 different conditions. Any condition was set up with the two protein concentrations as described above. About 1 μL of the protein solution was admixed with about 1 μL of a particular reservoir solution on a circle siliconized glass cover slide, and the well was sealed with the inverted slide, generating a hanging drop experiment. The plates were stored at ambient temperature. Microscopy of the drops was performed after six days. The conditions were classified into clear drops, drops containing random precipitation, drops containing crystals and drops containing mixtures of precipitated species and crystals.

Results:

From the 96 conditions tested, crystals in the shape of needle clusters were observed with the 5 mg/mL ABT-874 and about 24% PEG 4,000 at pH about 5.6.

Example 17

PEG 4,000/Sodium Citrate Grid Screen in Hanging Drop Vapor Diffusion Mode, Different Set Up A hanging drop vapor diffusion crystallization method was performed on ABT-874 using PEG 4,000/Sodium Citrate with a different set up. ABT-874 was buffered into a 20 mM HEPES/150 mM sodium chloride buffer at pH 7.4. The protein concentration was adjusted to 10 mg/mL. In another case, protein concentration was adjusted to 5 mg/mL.

A greased VDX plate and circle siliconized glass cover slides were used. 500 μL of a particular reservoir solution was prepared by admixing citrate buffer, 50% w/v PEG 4,000 solution and Milli Q water in each well. In this example, the citrate buffer molarity was kept constant at about 0.1M, and the PEG 4,000 concentration was used at about 12% w/v, 18% w/v, 24% w/v or 30% w/v. The pH was varied from about 4.2 to around 6.4 in 0.2 steps, generating 48 different conditions. Any condition was set up with the two protein concentrations as described above. Around 1 μL of the protein solution was admixed with around 1 μL of a particular reservoir solution on a circle siliconized glass cover slide, and the well was sealed with the inverted slide, generating a hanging drop experiment. The plates were stored at ambient temperature. Microscopy of the drops was performed after six days. The conditions were classified into clear drops, drops containing random precipitation, drops containing crystals and drops containing mixtures of precipitated species and crystals.

Results:

From the 96 conditions tested, no crystals were observed.

D. Batch Crystallization Experiments

A batch crystallization method was performed on ABT-874. Concentration values given in the following examples are initial values referring to the antibody solution and the crystallization solution before mixing of the two solutions.

All pH values, if not described otherwise, refer to the pH of an acetate buffer stock before it was combined with other substances, like the crystallization agent.

All buffer molarities, if not described otherwise, refer to sodium acetate concentrations in a stock solution before pH adjustment, typically performed using acetic acid glacial.

Example 18

PEG 4,000/Sodium Acetate Condition at 1 Ml Batch Volume

A crystallization method was performed on ABT-874 using PEG 4,000/Sodium Acetate at 1 Ml batch volume. ABT-874 was buffered into a buffer containing about 0.1M sodium acetate at a pH of around 5.2. The protein concentration was adjusted to 10 mg/mL.

Batch crystallization was performed by admixing about 500 μL of the protein solution with an equal volume of the crystallization buffer in a 1.5 mL Eppendorff reaction tube. 500 μL of a particular reservoir solution was prepared by admixing acetate buffer, 50% w/v PEG 4,000 solution and Milli Q water. In this example, the acetate buffer molarity was 0.1M, and the acetate buffer pH was around 6.7. PEG 4,000 was used at a concentration of around 14% w/v. The reaction tube was stored at ambient temperature. Microscopy of a 1 μL aliquot was performed after 16 days.

Results:

No crystals were observed after 16 days.

Example 19

PEG 4,000/Sodium Acetate Grid Screen in 300 μL Volume Batch Mode

A crystallization method was performed on ABT-874 using PEG 4,000/Sodium Acetate in a 300 μL volume batch mode.

ABT-874 was buffered into a buffer containing about 0.1M sodium acetate at a pH of around 5.5. The protein concentration was adjusted to 10 mg/mL.

Batch crystallization was performed by admixing about 150 μL of the protein solution with an equal volume of the crystallization buffer in a well. The well plate was subsequently sealed with adhesive tape to prevent water evaporation. 150 μL of a particular reservoir solution was prepared by admixing acetate buffer, 50% w/v PEG 4,000 solution and Milli Q water in each well. In this example, the acetate buffer molarity was kept constant at around 0.1M, and the acetate buffer pH was around 5.5 throughout. PEG 4,000 was varied from around 12% w/v to around 34% w/v in 2% steps. Any condition was assessed in triplicate. The plate was stored at ambient temperature. Microscopy of the drops was performed during the following two days.

Results:

From the 36 wells examined, crystals were observed in experiments, that were set up with between 22% w/v and 26% w/v PEG 4,000.

Example 20

PEG 4,000/Sodium Acetate Condition at 1 Ml Batch Volume, Different PEG 4,000 Concentrations A crystallization method was performed on ABT-874 using PEG 4,000/Sodium Acetate in a 1 Ml batch volume using different PEG 4,000 concentrations. ABT-874 was buffered into a buffer containing around 0.1M sodium acetate at a pH of around 5.5. The protein concentration was adjusted to 10 mg/mL.

Batch crystallization was performed by admixing around 500 μL of the protein solution with an equal volume of the crystallization buffer in a 1.5 mL Eppendorff reaction tube. 500 μL of a particular reservoir solution was prepared by admixing acetate buffer, 50% w/v PEG 4,000 solution and Milli Q water. In this example, the acetate buffer molarity was 0.1M, and the acetate buffer pH was around 5.5. PEG 4,000 was used at a concentration of about 22% w/v. The experiment was set up in quadruplicate. The reaction tubes were stored at ambient temperature. Microscopy of 1 μL aliquots were performed multiple times during the following 78 days. Furthermore, the crystal yield was determined by OD 280. An aliquot of the suspension was centrifuged at 14,000 rpm, and the protein concentration in the supernatant was assessed.

Results:

Sword-like crystals appeared after seven days. No precipitated species were observed during the following months of storage. The crystal yield as determined by OD280 from residual protein concentration in the supernatant was between 50 and 70% after sixty days.

Example 21

PEG 4,000/Sodium Acetate Condition at 1 Ml Batch Volume, Different PEG 4,000 Concentrations A crystallization method was performed on ABT-874 using PEG 4,000/Sodium Acetate in a 1 Ml batch volume using different PEG 4,000 concentrations. ABT-874 was buffered into a buffer containing about 0.1M sodium acetate at a pH of about 5.5. The protein concentration was adjusted to 10 mg/mL.

Batch crystallization was performed by admixing about 500 μL of the protein solution with an equal volume of the crystallization buffer in a 1.5 mL Eppendorff reaction tube. 500 μL of a particular reservoir solution was prepared by admixing acetate buffer, 50% w/v PEG 4,000 solution and Milli Q water. In this example, the acetate buffer molarity was 0.1M, and the acetate buffer pH was about 5.5. PEG 4,000 was used at a concentration of about 26% w/v. The reaction tube was stored at ambient temperature. Microscopy of a 1 μL aliquot was performed multiple times during the following months.

Results:

After one day, precipitated species were observed. Sword-like crystals were observed after five days besides the precipitate.

Example 22

PEG 4,000/Sodium Acetate Condition at 1 Ml Batch Volume, Different PEG 4,000 Concentrations A crystallization method was performed on ABT-874 using PEG 4,000/Sodium Acetate in a 1 Ml batch volume using different PEG 4,000 concentrations. ABT-874 was buffered into a buffer containing about 0.1M sodium acetate at a pH of about 5.5. The protein concentration was adjusted to 10 mg/mL.

Batch crystallization was performed by admixing about 500 μL of the protein solution with an equal volume of the crystallization buffer in a 1.5 mL Eppendorff reaction tube. 500 μL of a particular reservoir solution was prepared by admixing acetate buffer, 50% w/v PEG 4,000 solution and Milli Q water. In this example, the acetate buffer molarity was 0.1M, and the acetate buffer pH was about 5.5. PEG 4,000 was used at a concentration of about 24% w/v. The reaction tube was stored at ambient temperature. Microscopy of a 1 μL aliquot was performed multiple times during the following months. Furthermore, the crystal yield was determined by OD 280. An aliquot of the suspension was centrifuged at 14,000 rpm, and the protein concentration in the supernatant was assessed.

Results:

Needle cluster like crystals appeared after one day. After five days, needle like crystals and platelets were observed besides the needle cluster like crystals. The crystal yield as determined by OD280 from residual protein concentration in the supernatant was between 60 and 70% after thirteen days.

Example 23

PEG 4,000/Sodium Acetate Grid Screen in 1 Ml Volume Batch Mode, Different Protein Concentration A crystallization method was performed on ABT-874 using PEG 4,000/Sodium Acetate in a 1 Ml batch volume using different protein concentrations. ABT-874 was buffered into a buffer containing about 0.1M sodium acetate at a pH of about 5.5. The protein concentration was adjusted to 5 mg/mL.

Batch crystallization was performed by admixing about 500 μL of the protein solution with an equal volume of the crystallization buffer in a well. The well plate was subsequently sealed with adhesive tape to prevent water evaporation.

500 μL of a particular reservoir solution was prepared by admixing acetate buffer, 50% w/v PEG 4,000 solution and Milli Q water in each well. In this example, the acetate buffer molarity was kept constant at about 0.1M, and the acetate buffer pH was about 5.5 throughout. PEG 4,000 was varied from about 12% w/v to about 34% w/v in 2% steps. Any condition was assessed in duplicate. The plate was stored at ambient temperature. Microscopy of the drops was performed during the following month.

Results:

From the 24 wells examined, sword-like crystals were observed in experiments that were set up with about 24% w/v and 26% w/v PEG 4,000.

Example 24

PEG 4,000/Sodium Acetate Grid Screen in 1 Ml Volume Batch Mode, Different Set Up A crystallization method was performed on ABT-874 using PEG 4,000/Sodium Acetate in a 1 Ml batch volume using different set up. ABT-874 was buffered into a buffer containing about 0.1M sodium acetate at a pH of about 5.5. The protein concentration was adjusted to 10 mg/mL.

Batch crystallization was performed by admixing about 500 µL of the protein solution with an equal volume of the crystallization buffer in a well. The well plate was subsequently sealed with adhesive tape to prevent water evaporation. 500 µL of a particular reservoir solution was prepared by admixing acetate buffer, 50% w/v PEG 4,000 solution and Milli Q water in each well. In this example, the acetate buffer molarity was kept constant at about 0.1M, and the acetate buffer pH was about 4.1, 4.6 and 5.1, respectively. PEG 4,000 was varied from about 20% w/v to about 28% w/v in 2% steps. The plate was stored at ambient temperature. Microscopy of the drops was performed during the following four days.

Results:

From the 18 wells examined, sword-like crystals were observed in experiments that were set up with 28% w/v PEG 4,000 and sodium acetate buffer at pH 5.1.

Example 25

PEG 4,000/Sodium Acetate Condition at 2 Ml Batch Volume, Different Temperature

A crystallization method was performed on ABT-874 using PEG 4,000/Sodium Acetate in a 2 Ml batch volume using different temperatures. ABT-874 was buffered into a buffer containing about 0.1M sodium acetate at a pH of about 5.5. The protein concentration was adjusted to 10 mg/mL.

Batch crystallization was performed by admixing about 1 mL of the protein solution with an equal volume of the crystallization buffer in a 2 mL Eppendorff reaction tube. 1 mL of a particular reservoir solution was prepared by admixing acetate buffer, 50% w/v PEG 4,000 solution and Milli Q water. In this example, the acetate buffer molarity was 0.1M, and the acetate buffer pH was about 5.5. PEG 4,000 was used at a concentration of about 22% w/v. The reaction tube was stored at 4-8° C. Microscopy of a 1 µL aliquot was performed multiple times during the following month.

Results:

Precipitated species were observed after storage overnight.

Example 26

PEG 4,000/Sodium Acetate Crystallization Condition at 10 Ml Batch Volume, Agitation A crystallization method was performed on ABT-874 using PEG 4,000/Sodium Acetate in a 10 Ml batch volume using agitation. ABT-874 was buffered into a buffer containing about 0.1M sodium acetate at a pH of about 5.5. The protein concentration was adjusted to 10 mg/mL.

Batch crystallization was performed by admixing about 5 mL of the protein solution with an equal volume of the crystallization buffer in a 50 mL Falcon tube. 5 mL of the crystallization buffer was prepared by admixing acetate buffer, 50% w/v PEG 4,000 solution and Milli Q water in the tube. In this example, the acetate buffer molarity was about 0.1M, and the acetate buffer pH was about 5.5. PEG 4,000 was used at a concentration of about 24% w/v. The tube was stored at ambient temperature, agitating the batch on a laboratory shaker. Microscopy of a 1 µL aliquot of the solution was performed multiple times during the following weeks.

Results:

Sword-like crystals appeared after six days, but were almost completely adsorbed to the container surface. It could not be concluded from microscopy that the batch was free of precipitated species. The crystallization liquor was almost clear.

Example 27

PEG 4,000/Sodium Acetate Crystallization Condition at 10 Ml Batch Volume, No Agitation A crystallization method was performed on ABT-874 using PEG 4,000/Sodium Acetate in a 10 Ml batch volume with no agitation. ABT-874 was buffered into a buffer containing about 0.1M sodium acetate at a pH of about 5.5. The protein concentration was adjusted to 10 mg/mL.

Batch crystallization was performed by admixing about 5 mL of the protein solution with an equal volume of the crystallization buffer in a 50 mL Falcon tube. 5 mL of the crystallization buffer was prepared by admixing acetate buffer, 50% w/v PEG 4,000 solution and Milli Q water in the tube. In this example, the acetate buffer molarity was about 0.1M, and the acetate buffer pH was about 5.5. PEG 4,000 was used at a concentration of about 24% w/v. The tube was stored at ambient temperature. Microscopy of a 1 µL aliquot of the solution was performed multiple times during the following weeks. Furthermore, the crystal yield was determined by OD 280. An aliquot of the suspension was centrifuged at 14,000 rpm, and the protein concentration in the supernatant was assessed.

Results:

Needle cluster like crystals appeared after one day. After four days, needle like crystals were observed besides the needle cluster like crystals. The crystal yield as determined by OD280 from residual protein concentration in the supernatant was between 30 and 40% after seven days.

Example 28

PEG 4,000/Sodium Acetate Crystallization Condition at 10 Ml Batch Volume, Agitation, Different Container Material A crystallization method was performed on ABT-874 using PEG 4,000/Sodium Acetate in a 10 Ml batch volume using agitation and different container materials. ABT-874 was buffered into a buffer containing about 0.1M sodium acetate at a pH of about 5.5. The protein concentration was adjusted to 10 mg/mL.

Batch crystallization was performed by admixing about 5 mL of the protein solution with an equal volume of the crystallization buffer in a 50 mL glass class I vial. 5 mL of the crystallization buffer was prepared by admixing acetate buffer, 50% w/v PEG 4,000 solution and Milli Q water in the vial. In this example, the acetate buffer molarity was about 0.1M, and the acetate buffer pH was about 5.5. PEG 4,000 was used at a concentration of about 24% w/v. The vial was stored at ambient temperature, agitating the batch on a laboratory shaker. Microscopy of a 1 µL aliquot of the solution was performed multiple times during the following weeks. Furthermore, the crystal yield was determined by OD 280. An aliquot of the suspension was centrifuged at 14,000 rpm, and the protein concentration in the supernatant was assessed.

Figure 7:
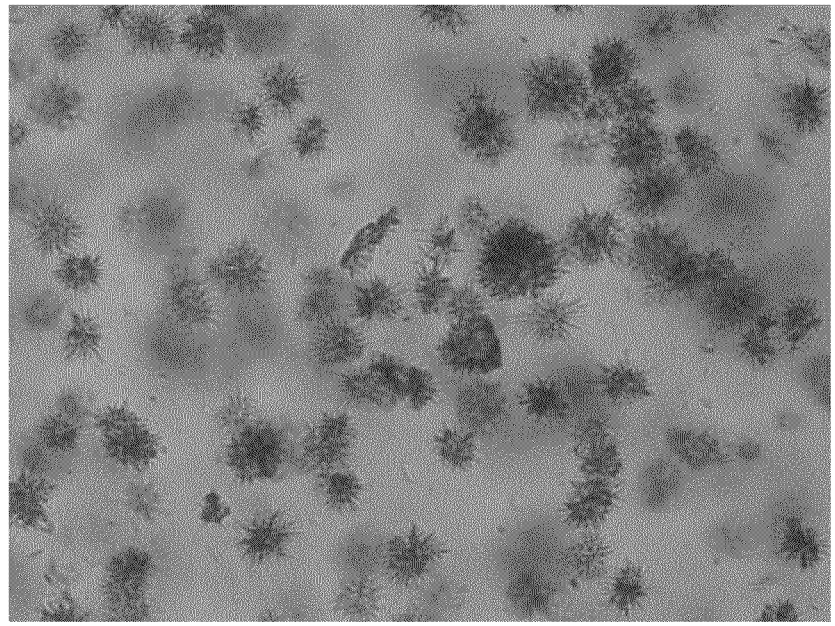
FIG. 7 shows light microscopic pictures of crystals (needle-clusters) obtained according to Example 28 (crystallization with agitation).

Results:

Sword-like crystals were observed after eighteen days. The crystal yield as determined by OD280 from residual protein concentration in the supernatant was between 40 and 50% after eighteen days. A light microscopic picture of the needle-clusters (width of the picture corresponding to a length of 450 µm) is shown in FIG. 7.

Example 29

PEG 4,000/Sodium Acetate Crystallization Condition at 10 Ml Batch Volume, Agitation, Different Container Material and Influence of Polysorbate 80

A crystallization method was performed on ABT-874 using PEG 4,000/Sodium Acetate in a 10 Ml batch volume using agitation, different container materials and influence of polysorbate 80. ABT-874 was buffered into a buffer containing about 0.1M sodium acetate at a pH of about 5.5. The protein concentration was adjusted to 10 mg/mL.

Batch crystallization was performed by admixing about 5 mL of the protein solution with an equal volume of the crystallization buffer in a 50 mL glass class I vial. 5 mL of the crystallization buffer was prepared by admixing acetate buffer, 50% w/v PEG 4,000 solution and Milli Q water in the vial. In this example, the acetate buffer molarity was about 0.1M, and the acetate buffer pH was about 5.5. PEG 4,000 was used at a concentration of about 24% w/v. Furthermore, polysorbate 80 in a concentration of 0.1% was added to the buffer. The vial was stored at ambient temperature, agitating the batch on a laboratory shaker. Microscopy of a 1 µL aliquot of the solution was performed multiple times during the following weeks. Furthermore, the crystal yield was determined by OD 280. An aliquot of the suspension was centrifuged at 14,000 rpm, and the protein concentration in the supernatant was assessed.

Results:

Sword-like crystals were observed after eighteen days. No difference was observed between the crystal shape of this example and Example 28 (no addition of polysorbate 80). The crystal yield as determined by OD280 from residual protein concentration in the supernatant was between 25 and 35% after eighteen days.

Example 30

Different PEG 4,000/Sodium Acetate Crystallization Conditions at 10 Ml Batch Volume And Comparison Of Agitated And Non Agitated Batches A crystallization method was performed on ABT-874 using PEG 4,000/Sodium Acetate in a 10 Ml batch volume using a comparison of agitated and non-agitated batches. ABT-874 was buffered into a buffer containing about 0.1M sodium acetate at a pH of about 5.5. The protein concentration was adjusted to 10 mg/mL.

Batch crystallization was performed by admixing about 5 mL of the protein solution with an equal volume of the crystallization buffer in a 50 mL glass class I vial. 5 mL of the crystallization buffer was prepared by admixing acetate buffer, 50% w/v PEG 4,000 solution and Milli Q water in the vial. In this example, the acetate buffer molarity was about 0.1M, and the acetate buffer pH was about 5.5. PEG 4,000 was used at a concentration of about 22% w/v and 24% w/v. The vials were stored at ambient temperature, either without agitation or agitating the batch by tumbling. Microscopy of a 1 µL aliquot of the solution was performed multiple times during the following weeks. Furthermore, the crystal yield of one batch was determined by OD 280. An aliquot of the suspension was centrifuged at 14,000 rpm, and the protein concentration in the supernatant was assessed.

Results:

In both agitated batches, precipitated species were observed after 26 days. The non-agitated batch with the buffer of about 22% w/v PEG 4,000 contained sword-like crystals after 26 days, but the crystal yield was deemed low as the suspension was almost clear macroscopically. The non-agitated batch with the buffer of about 24% w/v PEG 4,000 contained sword-like crystals after 26 days. The yield as determined from the supernatant after 70 days was between 65 and 75%.

Example 31

Influence of Seeding

The influence of seeding on ABT-874 crystal yield was examined. The non-agitated batch with the crystallization buffer containing about 22% w/v PEG 4,000 from Example 30 showed very low crystal yield after 26 days. Therefore, the batch was incubated with about 100 µL of the non-agitated batch with the crystallization buffer containing about 24% w/v PEG 4,000 from the same example.

Results:

No obvious yield extension resulted from the incubation with seed crystals.

Example 32

PEG 4,000/Sodium Acetate Crystallization Conditions at 10 Ml Batch Volume, Different Protein Concentration, Comparison of Agitated and Non Agitated Batches A crystallization method was performed on ABT-874 using PEG 4,000/Sodium Acetate in a 10 Ml batch volume using different protein concentrations and a comparison of agitated and non-agitated batches. ABT-874 was buffered into a buffer containing about 0.1M sodium acetate at a pH of about 5.5. The protein concentration was adjusted to 5 mg/mL.

Batch crystallization was performed by admixing about 5 mL of the protein solution with an equal volume of the crystallization buffer in a 15 mL glass class I vial. 5 mL of the crystallization buffer was prepared by admixing acetate buffer, 50% w/v PEG 4,000 solution and Milli Q water in the vial. In this example, the acetate buffer molarity was about 0.1M, and the acetate buffer pH was about 5.5. PEG 4,000 was used at a concentration of about 22% w/v, 24% w/v and 26% w/v. The vials were stored at ambient temperature, either without agitation or with agitating the batch on a laboratory shaker. Microscopy of a 1 µL aliquot of the solution was performed multiple times during the following weeks. Furthermore, the crystal yield of one batch was determined by OD 280. An aliquot of the suspension was centrifuged at 14,000 rpm, and the protein concentration in the supernatant was assessed.

Figure 8:
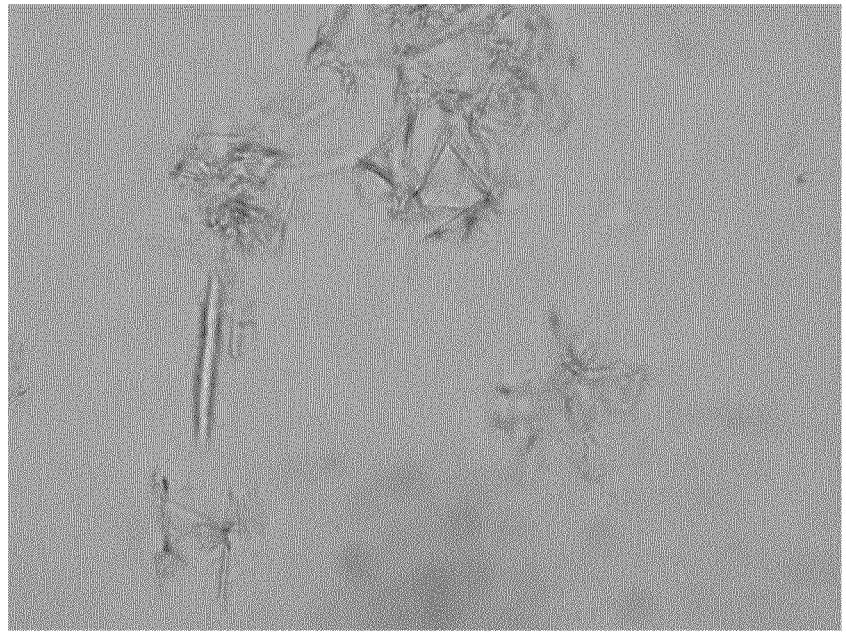
FIG. 8 shows light microscopic pictures of crystals (needles) obtained according to Example 32 (crystallization without agitation).

Results:

The batches containing the buffer with about 22% w/v and about 24% w/v PEG 4,000 were clear after 65 days. While the agitated batch containing the crystallization buffer with about 26% w/v PEG 4,000 contained precipitated species after 4 days, the non-agitated batch of the same crystallization buffer contained sword-like crystals after 4 days. The crystal yield of this particular batch as determined from the supernatant after 26 days was between 40 and 50%. A light microscopic picture of the crystals (width of the picture corresponding to a length of 225 µm) obtained without agitation is shown in FIG. 8.

Example 33

PEG 4,000/Sodium Acetate Crystallization Condition at 10 Ml Batch Volume, Different Set Up A crystallization method was performed on ABT-874 using PEG 4,000/Sodium Acetate in a 10 Ml batch volume using a different set up. ABT-874 was buffered into a buffer containing about 0.1M sodium acetate at a pH of about 5.5. The protein concentration was adjusted to 10 mg/mL.

Batch crystallization was performed by admixing about 5 mL of the protein solution with an equal volume of the crystallization buffer in a 15 mL Falcon tube. 5 mL of the crystallization buffer was prepared by admixing acetate buffer, 50% w/v PEG 4,000 solution and Milli Q water in the tube. In this example, the acetate buffer molarity was about 0.1M, and the acetate buffer pH was about 5.5. PEG 4,000 was used at a concentration of about 22% w/v. The tube was stored at ambient temperature. Microscopy of a 1 µL aliquot of the solution was performed multiple times during the following weeks. Furthermore, the crystal yield of the batch was determined by OD 280. An aliquot of the suspension was centrifuged at 14,000 rpm, and the protein concentration in the supernatant was assessed.

Figure 9:
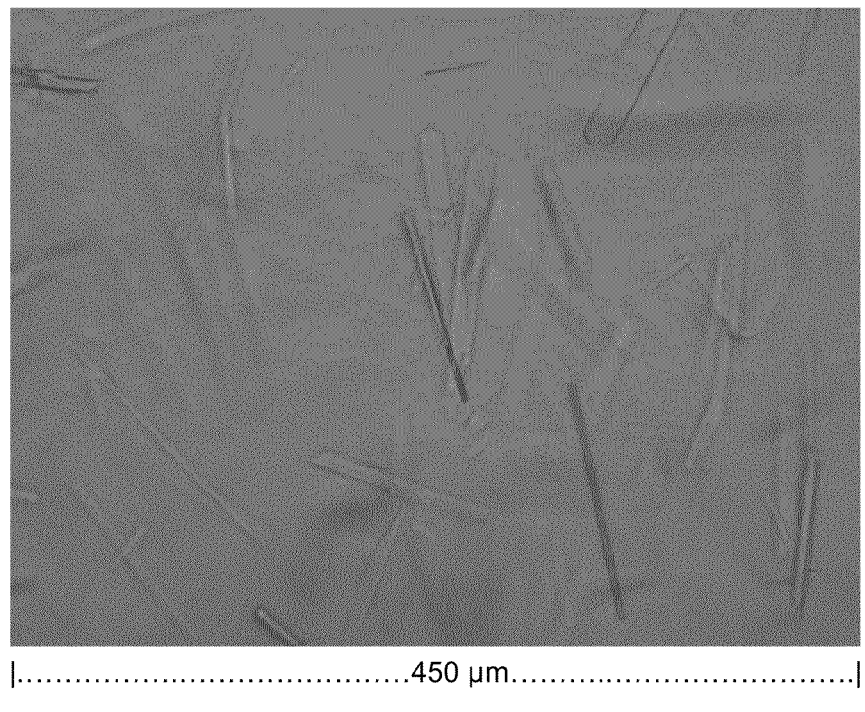
FIG. 9 shows light microscopic pictures of crystals (needles) obtained according to Example 33 (crystallization without agitation).

Results:

Sword-like crystals were observed after 11 days. The crystal yield of this batch as determined from the supernatant after 26 days was between 40 and 50%. A light microscopic picture of the crystals (width of the picture corresponding to a length of 450 µm) obtained without agitation after 26 days is shown in FIG. 9.

Example 34a

PEG 4,000/sodium acetate crystallization condition at 50 mL Batch Volume

A crystallization method was performed on ABT-874 using PEG 4,000/Sodium Acetate in a 50 mL batch volume. ABT-874 was buffered into a buffer containing about 0.1M sodium acetate at a pH of about 5.5. The protein concentration was adjusted to 10 mg/mL.

Batch crystallization was performed by admixing about 25 mL of the protein solution with an equal volume of the crystallization buffer in a 50 mL Falcon tube. 25 mL of the crystallization buffer was prepared by admixing acetate buffer, 50% w/v PEG 4,000 solution and Milli Q water in the tube. In this example, the acetate buffer molarity was about 0.1M, and the acetate buffer pH was about 5.5. PEG 4,000 was used at a concentration of about 22% w/v. The tube was stored at ambient temperature. Microscopy of a 1 µL aliquot of the solution was performed multiple times during the following weeks. Furthermore, the crystal yield of the batch was determined by OD 280. An aliquot of the suspension was centrifuged at 14,000 rpm, and the protein concentration in the supernatant was assessed.

Results:

Sword-like crystals were observed after 3 days. The crystal yield of this batch as determined from the supernatant after 16 days was between 50 and 60%.

Example 34b

PEG 4,000/Sodium Acetate Crystallization Condition at 700 Ml Batch Volume

A crystallization method was performed on ABT-874 using PEG 4,000/Sodium Acetate in a 700 mL batch volume. ABT-874 was buffered into a buffer containing about 0.1M sodium acetate at a pH of about 5.5. The protein concentration was adjusted to 10 mg/mL.

Batch crystallization was performed by admixing about 350 mL of the protein solution with an equal volume of the crystallization buffer in a 1 L poly propylene bottle. 350 mL of the crystallization buffer was prepared by admixing acetate buffer, PEG 4,000 and Milli Q water. In this example, the acetate buffer molarity was about 0.1M, and the acetate buffer pH was about 5.5. PEG 4,000 was used at a concentration of about 22% w/v. The bottle was stored at ambient temperature. Microscopy of a 1 µL aliquot of the solution was performed after 40 days. Furthermore, the crystal yield of the batch was determined by OD 280. An aliquot of the suspension was centrifuged at 14,000 rpm, and the protein concentration in the supernatant was assessed.

Figure 10:
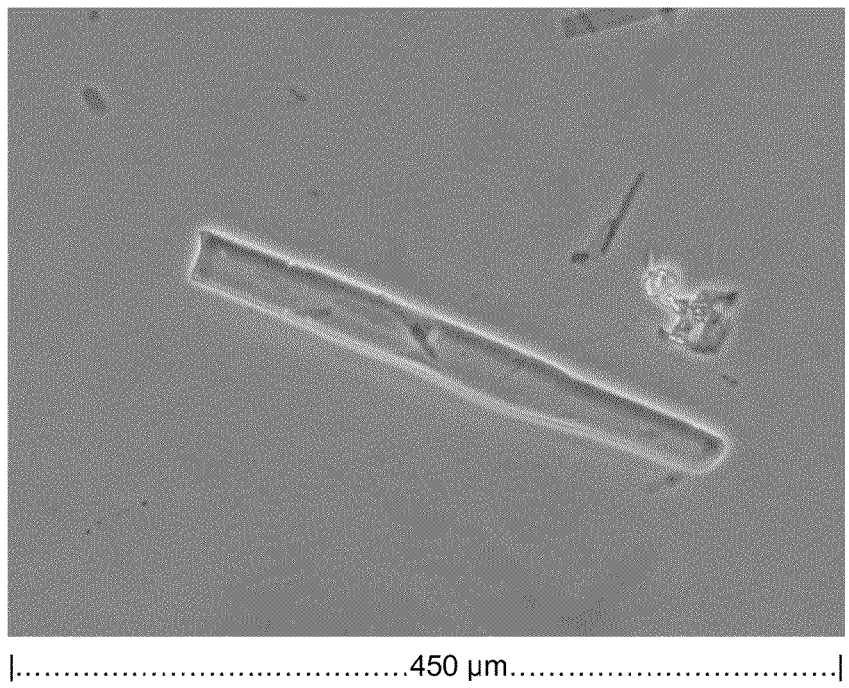
FIG. 10 shows light microscopic pictures of crystals (needles) obtained according to Example 34b (crystallization without agitation).

Results:

Sword-like crystals were observed after 40 days. The crystal yield of this batch as determined from the supernatant after 40 days was between 50 and 60%. A light microscopic picture of the crystals (width of the picture corresponding to a length of 450 µm) obtained after 40 days without agitation is shown in FIG. 10.

The experimental conditions of the above batch experiments are summarized in the following Table 1:

TABLE 1

Batch Experiments

| Example | Batch Volume, ml | Crystallization Buffer (initial concentrations) | Agitation | Crystals (Yield %) | pH Bufer | pH Final | Protein Conc. Final mg/ml | Temp. | day of visual control |
|---|---|---|---|---|---|---|---|---|---|
| 18 | 1 | 14%[1] PEG4000, 0.1 M NaAc | | — | 6.7 | | 5 | amb | 16 d |
| 25 | 2 | 22% PEG4000, 0.1 M NaAc | | precip. | 5.5 | 5.6 | 5 | 4-8° C. | 1 d |
| 19 | 0.3 | 22-26% PEG4000, 0.1 M NaAc | | +(n.d.) | 5.5 | | 5 | amb | 2 d |
| 20 | 1 | 22% PEG4000, 0.1 M NaAc | | +(50-70) | 5.5 | 5.6 | 5 | amb | 7 d |
| 21 | 1 | 26% PEG4000, 0.1 M NaAc | | +(n.d.) | 5.5 | 5.6 | 5 | amb | 5 d |

TABLE 1-continued

Batch Experiments

| Example | Batch Volume, ml | Crystallization Buffer (initial concentrations) | Agitation | Crystals (Yield %) | pH Bufer | pH Final | Protein Conc. Final mg/ml | Temp. | day of visual control |
|---|---|---|---|---|---|---|---|---|---|
| 22 | 1 | 24% PEG4000, 0.1 M NaAc | | +(60-70) (13 d) | 5.5 | 5.6 | 5 | amb | 1 d |
| 23 | 1 | 24-26% PEG4000, 0.1 M NaAc | | +(n.d.) | 5.5 | 5.6 | 2.5 | amb | 2 d |
| 24 | 1 | 28% PEG4000, 0.1 M NaAc | | +(n.d.) | 5.1 | 5.2-5.3 | 5 | amb | 4 d |
| 26 | 10 | 24% PEG4000, 0.1 M NaAc | + | +(n.d.) | 5.5 | 5.6 | 5 | amb | 6 d |
| 27 | 10 | 24% PEG4000, 0.1 M NaAc | | +(30-40) | 5.5 | 5.6 | 5 | amb | 1 d |
| 28 | 10 | 24% PEG4000, 0.1 M NaAc | + | +(40-50) | 5.5 | 5.6 | 5 | amb | 18 d |
| 29 | 10 | 24% PEG4000, 0.1 M NaAc 0.1% polysorbate 80 | + | +(25-35) | 5.5 | 5.6 | 5 | amb | 18 d |
| 30 | 10 | 22% PEG4000, 0.1 M NaAc | | +(n.d.) | 5.5 | 5.6 | 5 | amb | 26 d |
| | | 22% PEG4000, 0.1 M NaAc | + | precip. | | | | | |
| | | 24% PEG4000, 0.1 M NaAc | | +65-75 (70d) | | | | | 26 d |
| | | 24% PEG4000, 0.1 M NaAc | + | precip. | | | | | |
| 32 | 10 | 22% PEG4000, 0.1 M NaAc | | none | 5.5 | 5.6 | 2.5 | amb | 64 d |
| | | 24% PEG4000, 0.1 M NaAc | | none | | | | | 64 d |
| | | 26% PEG4000, 0.1 M NaAc | | +(40-50) | | | | | 4 d |
| | | 26% PEG4000, 0.1 M NaAc | + | precip. | | | | | 4 d |
| 33 | 10 | 22% PEG4000, 0.1 M NaAc | | +(40-50) (26 d) | 5.5 | 5.6 | 5 | amb | 11 d |
| 34a | 50 | 22% PEG4000, 0.1 M NaAc | | +(50-60) (16 d) | 5.5 | 5.6 | 5 | amb | 3 d |
| 34b | 700 | 22% PEG4000, 0.1 M NaAc | | +(50-60) (40 d) | 5.5 | 5.6 | 5 | amb | 40 |

[1] % (w/v)

E. Methods for Crystal Processing and Analysis

Example 35

Washing of Crystals

After formation of the crystals, a washing step without redissolving the crystals may be favorable. After the crystallization process was finished, the crystal slurry was transferred into a centrifugation tube and centrifuged at 500 to 1000×g for twenty minutes. The centrifugation was performed at 4° C. or ambient temperature. After centrifugation, the supernatant was decanted, and the crystal pellet were easily resuspended in a buffer containing about 24% w/v PEG 4,000 in about 0.1M sodium acetate at a pH about 5.5. No measurable solubility of ABT-874 crystals in such a washing buffer occurred, as analyzed by OD280. The centrifugation/resuspension steps were subsequently repeated for one to three times, and after this washing procedure, the pellet was resuspended and stored in such a buffer.

Example 36

Analysis of Crystals by SDS PAGE

To confirm the protein character of the crystals, the crystals were washed with a washing buffer as described in example 32. After assuring by OD280 that no more dissolved protein was in the liquor, the crystals were centrifuged, the supernatant was decanted, and the crystals were subsequently dissolved in distilled water. OD280 measurement of this solution revealed that protein was now present, as the absorbance of the sample was now significantly higher as in the residual washing buffer. SDS PAGE analysis of this solution of redissolved crystals, when compared to an original ABT-874 sample, showed the same pattern.

Example 37

Analysis of Crystals by SE-HPLC

To assess the content of aggregated species of the ABT-874 crystals, an aliquot of washed crystals was centrifuged and redissolved in the SE-HPLC running buffer (92 mM di sodium hydrogen phosphate/211 mM di sodium sulfate pH 7.0). Right after the end of the crystallization process, in this example 16 days at ambient temperature, the aggregate content typically increased slightly from about 0.9% to about 1.6-1.7%. It is not yet clear whether such aggregates are contained in the crystals or at their surface and were not properly removed by the washing process.

F. Miscellaneous Examples

Concentration values given in the following examples are initial values referring to the antibody solution and the crystallization solution before mixing of the two solutions.

All pH values, if not described otherwise, refer to the pH of an acetate buffer stock before it was combined with other substances, like the crystallization agent.

All buffer molarities, if not described otherwise, refer to sodium acetate concentrations in a stock solution before pH adjustment, typically performed using acetic acid glacial.

Example 38

Solid Crystallization Agent

ABT-874 was buffered into a buffer containing about 0.1M sodium acetate at a pH of about 5.5. The protein concentration was adjusted to 10 mg/mL.

Batch crystallization was performed by admixing about 500 µL of the protein solution with about 380 µL acetate buffer (0.1M, pH 5.5) in a 2 mL Eppendorf reaction tube. Subsequently, solid polyethylene glycol was added to a final concentration of 12% m/v (120 mg/mL). The tube was subsequently closed and agitated until complete dissolution of the crystallization agent. The tube was stored at ambient temperature without agitation. Microscopy of aliquots of the crystallization mixture was performed multiple times during the following weeks.

Results:

Sword-like crystals were observed after seven days.

Example 39

Different Buffer Preparation Protocol and Preparation of Crystals

In this example, the acetate buffers were prepared as described in the following: 60 g of acetic acid glacial were diluted with about 840 mL of purified water. The pH was adjusted with sodium hydroxide solution and the volume adjusted to 1,000 mL. In this case, the total acetate amount was fixed at 1M (100 mM in the protein solution, the crystallization buffer and the crystallization mixture).

Crystallization is performed as according to Example 34a; sword-like crystals are observed after three days.

Example 40

Preparation of Encapsulated Crystals

Crystals as obtained in Example 34 are positively charged as determined via zeta potential measurement using a Malvern Instruments Zetasizer nano. The crystals are washed and suspended in a buffer containing excipients which conserve crystallinity, and which has a pH that keeps the crystals charged. Subsequently, an appropriate encapsulating agent is added to the crystal suspension. In this context, an appropriate encapsulating agent is a (polymeric) substance with low toxicity, biodegradability and counter ionic character. Due to this counter ionic character, the substance is attracted to the crystals and allows coating. By this technique, the dissolution of crystals in media, which do not contain any other excipient maintaining crystallinity is preferably sustained.

Example 41

Preparation of Encapsulated/Embedded Crystals

Crystals are obtained as described in Example 34. The crystals are washed and suspended in a buffer containing excipients which conserve crystallinity.

The crystals can then be embedded by drying the crystals and combining these dried crystals with a carrier, e.g. by compression, melt dispersion, etc.
- encapsulated/embedded by combining a crystal suspension with a carrier solution which is not miscible with water. The carrier precipitates after removal of the solvent of the carrier. Subsequently, the material is dried.
- encapsulated/embedded by combining a crystal suspension with a water miscible carrier solution. The carrier precipitates as its solubility limit is exceeded in the mixture.
- embedded by combining dried crystals or a crystal suspension with a water miscible carrier solution.
- embedded by combining dried crystals with a carrier solution which is not water miscible.

Example 42

Investigation of Precipitated ABT-874 a) Precipitation

Acetate buffer was prepared by dissolving 1 mole of sodium acetate in water and adjusting pH to 5.5 with acetic acid (100%). The stock solution was diluted 1:10 with water for buffer exchange. The PEG 4000 solution was prepared by dissolving 20 g PEG 4000 in 5 mL 1M sodium acetate buffer pH 5.5 and water. After dissolution, the volume was adjusted to 50 mL with water. 5 mL of 10 mg/mL ABT874 (in 0.1M sodium acetate buffer pH 5.5) (original buffer exchanged by diafiltration) were admixed with 5 mL 40% PEG 4000 in 0.1M sodium acetate buffer pH 5.5.

The precipitate batch was kept at room temperature overnight without agitation. Non-birefringent particles in the magnitude of approx. 1-10 μm formed.

b) Washing of Precipitate 2 mL of the precipitate slurry were put into a centrifuge and centrifuged at 500×g for 20 min. The supernatant was discarded, and the pellet was resuspended in 2 mL of a 40% PEG 4000 in 0.1M sodium acetate buffer pH 5.5 (prepared in accordance to the procedure above). Protein concentration of the final suspension was determined by OD280 to be 3.9 mg/mL.

G. Crystal Characterization

In the following section, experiments that were performed to determine whether crystalline monoclonal antibody ABT-874 retains the bioactivity characteristic of never-crystallized ABT-874 upon redissolution of the crystalline material are summarized.

G1. Bioactivity Test by Determination of the IFN-γ Production of NK-92 Cells a) General Method The biological activity of redissolved ABT-874 crystals was measured by a cell-based assay that monitors the IFN-γ production of NK-92 cells in response to stimulation by IL-12. Prior to analysis the samples were diluted first to 30 μg/mL in cell culture medium (α-MEM medium with 20% FCS and 200 mM L-glutamine). Subsequently samples were further diluted in 11 steps from 3 μg/mL to 0.1 ng/mL. The IL-12 solution was diluted to 10 ng/mL in cell culture medium and added to the ABT-874 samples. The mixtures were then incubated at 37° C. and 5% CO2 for 1 hour.

A suspension of NK-92 cells (2.0×106 cells/mL) was pipetted into a 96-well microplate, the ABT-874/IL-12 mixtures were added to the cells and the microplates were then incubated at 37° C. and 5% CO2 for about 20 hours. After incubation the microplates were centrifuged at 1,000 rpm and 5° C. for 10 min and 50 μl of the supernatant of each well were used to measure the amount of IFN-γ produced by the cells by an ELISA (ELISA Kit Human Interferon-γ, Pierce, Cat. No. EHIFNG).

The biotinylated anti IFN-γ antibody solution was pipetted into the 96-well precoated microplate and the cell culture supernatants were added (4 rows for each of both samples). After incubation of the microplate for 2 hours at room temperature it was washed. After this the Streptavidin-HRP solution was added and the microplate was incubated for another 30 min and then washed. After the TMB substrate was added, the microplate was incubated at room temperature for about 20 min in the dark and the reaction was then stopped by adding the stop solution.

Finally the absorption was measured within the next 5 min in a microplate reader at 450 nm (correction wavelength 550 nm) and the results were plotted versus the ABT-874 concentration. The IC50 values were then assessed using a 4-parameter nonlinear curve fit and the relative biological activity of the sample was calculated by dividing the IC50 value of the reference standard by the IC50 value of the sample and multiplication by 100%.

b) Relative Activity for ABT-874 Crystals

The test was performed as a comparison of the biological activity of the sample to that of a reference standard. The amounts of IFN-γ produced by the cells were measured by a commercially available ELISA kit and were reported as absorption units at a wavelength of 450 nm. These values, plotted versus the concentration of ABT-874 and assessed by a 4-parameter nonlinear regression, revealed the IC50 values for the inhibition of the IL-12 effect by ABT-874. Since both samples were run in four repeats on one microplate this results in four IC50 values for ABT-874 reference standard and the sample respectively. Subsequently, the mean of the IC50 values of the reference standard was calculated and the relative activity of each repeat of the sample was assessed by dividing the mean IC50 value of the reference standard by the relevant IC50 value of the sample and multiplication by 100%.

The test of the sample (crystal suspension 2.9 mg/mL) revealed a relative biological activity of 98%. Thus, the sample can be considered as fully biologically active.

G2. Microscopic Characterization

In the following, data on microscopic characterization of crystals of ABT-874 will be presented.

a) Optical Analysis of mAb Crystal Batch Samples

After homogenization, aliquots of 1 to 10 µL sample volume were pipetted onto an object holder plate and were covered with a glass cover slide. The crystal preparations were assessed using a Zeiss Axiovert 25 inverted light microscope equipped with E-PI 10× oculars and 10×, 20× and 40× objectives, respectively. Pictures were taken using a digital camera (Sony Cybershot DSC S75).

b) Scanning Electron Microscope (SEM) characterization of ABT-874 crystals

To image protein crystals with an electron microscope they must be dry, electrically conductive and stable enough to tolerate high vacuum and the energy of an electron beam. This protocol separates the crystals from their buffer by filtration, stabilizes the crystals by chemically fixing them with a glutaraldehyde based fixative, dehydrates them through a graded series of ethanol, dries them by the critical point method and plasma coats them with gold to make them electrically conductive.

b1) Materials 0.2 M Sorensen's Phosphate Buffer (SPB)—0.15 M disodium phosphate, 0.05 M monobasic potassium phosphate, pH 7.3

Karnovsky's fixative—2.5% glutaraldehyde, 1.5% paraformaldehyde, 0.1 M SPB

50%, 75%, 95% and 100% ethanol

ABT-874 crystal sample in crystallization buffer (from Example 34, stored in washing buffer from Example 35)

ABT-874 crystallization buffer (washing buffer from example 35)

Millipore stainless steel filter assembly for attaching 13 mm filter membranes to syringes 0.4 µm polycarbonate filter membranes (Nucleopore, Cat#110407)

b2) Equipment

Critical Point Dryer (CPD)—Baltec Model CPD030, Asset LC978501

Scanning electron microscope (SEM)—Philips XL30 field emission scanning electron microscope Sputter Coater—Denton Desk II sputter coater, Asset LC827847 b3) Procedure

Steps 3-12 are performed by flushing solution through the filter assembly and holding the syringe on the filter assembly for designated hold time.

1. Load syringe filter holder with polycarbonate filter;
2. Mix 0.1 ml of crystal sample with 0.4 ml of crystal buffer in 1.0 ml syringe;
3. Dispense diluted crystal solution through filter assembly;
4. Dispense 1 ml of crystal buffer and hold for 2 min;
5. Dispense 1 ml of 50% fix, 50% crystal buffer and hold for 2 min;
6. Dispense 1 ml of 100% fixative and hold for 2 min;
7. Dispense 1 ml of SPB and hold for 2 min;
8. Dispense 1 ml of SPB and hold for 2 min, again;
9. Dispense 1 ml of 50% ethanol and hold for 2 min;
10. Dispense 1 ml of 75% ethanol and hold for 2 min;
11. Dispense 1 ml of 95% ethanol and hold for 2 min;
12. Dispense 1 ml of 100% ethanol and hold for 2 min, repeat step 3 times;
13. Transfer filter membrane with attached crystals to CPD filled w/100% ethanol;
14. Process filter through CPD as follows:
    a. Five exchanges of liquid CO2 at 10° C., mixing for 5 minutes per exchange;
    b. Heat to 40° C., 80 bar pressure; and
    c. Slowly bleed back to atmosphere over 20 minutes;
15. Mount filter membrane on SEM support;
16. Sputter coat w/gold for 60 seconds;
17. Examine with SEM;

c) Results

In the attached FIGS. 1 to 5 representative pictures of ABT-874 crystals are presented.

FIG. 1 shows a light micrograph of ABT-874 crystals in crystallization buffer (from Example 34, stored in washing buffer from example 35) obtained according to Example 34. The crystal habit is similar to habit of fixed dried crystals shown in FIGS. 2 to 5. The crystals exhibited birefringence.

FIGS. 2 to 5 show SEMs at different magnification of ABT-874 crystals obtained according to Example 34.

G3. Birefringence

Crystals as generated from all batch experiments exhibited birefringence.

G4. Syringeability.

An ABT-874 crystal suspension of 150 mg/mL protein incorporated in crystals and formulated in a washing buffer from example 35 is syringeable through a 27 G needle H. Capillary Isoelectric Focusing (cIEF) Experiments with ABT-874 a) Equipment

The iCE280 analyzer (Convergent Bioscience) was used for the analysis. System ID 1054 (IS #2785).

b) Material

The capillary used was of 50 mm length, 100 µm ID column, coated (Convergent, Catalogue #101700. The Electrolytes used were—Anolyte (80 mM $H_3PO_4$) and Catholyte (100 mM NaOH). (Convergent, Catalogue #101800). Carrier ampholyte is 4% Pharmalyte (8-10.5), (GE Healthcare, Catalogue #17-0455-01. Additive was methyl cellulose (0.35%), (Convergent, Catalogue #101876). Internal pI markers were from BioRad (8.4, 8.5, 10.1 and 10.4—BioRad, Catalogue number 148-2100, Lot#482-511) pI marker mix.

| | Volume (µL) |
|---|---|
| PI marker 8.4 | 2.5 |
| PI marker 8.5 | 2.5 |
| PI marker 10.1 | 2.5 |
| PI marker 10.4 | 2.5 |
| Water | 40 |
| Total | 50 | c) Methods

Focusing time was 2 minute at 1500V and 20 minutes at 3000V. Sample preparation procedure—Mab crystals, Mab precipitate and the reference standard were all diluted to about 1 mg/ml in Milli-Q water. Sample preparation procedure (with urea).

|  | Volume (μL) |
|---|---|
| Milli-Q water | 92 |
| 1% Methyl cellulose | 70 |
| Carrier—Pharmalyte | 8 |
| Sample (1 mg/mL) | 30 |
| PI marker mix (Table 1) | 16 |
| Total | 216 |

The samples were mixed in 1.5 mL micro-centrifuge tubes as shown in the table above. Urea was then added (20 mg) to give a final concentration of about 1.6 M. The centrifuge tubes were then vortexed, centrifuged for 10 minutes and then carefully transferred into vials for analysis.

d) Results

Figure 6A:
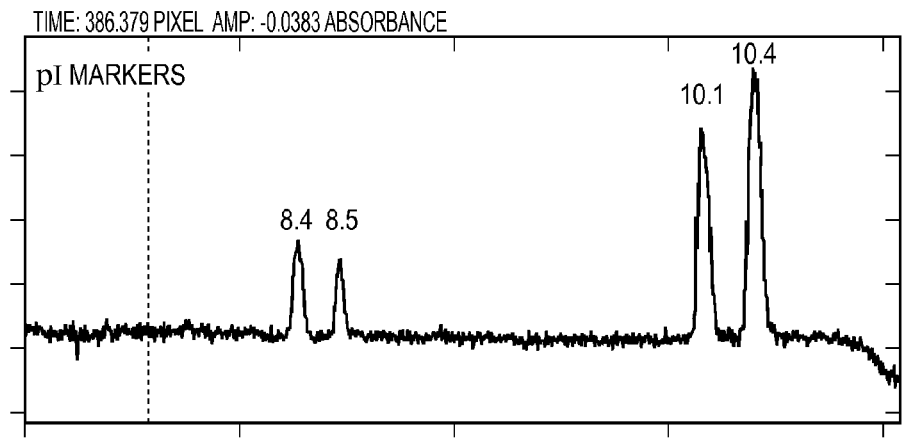
FIGS. 6A-C show the results of Capillary Isoelectric Focusing (cIEF) Experiments with ABT-874.
Figure 6B:
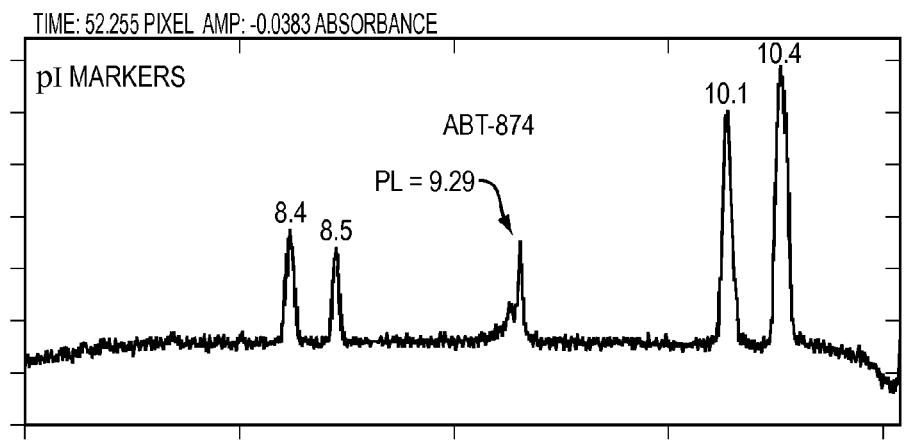
Figure 6C:
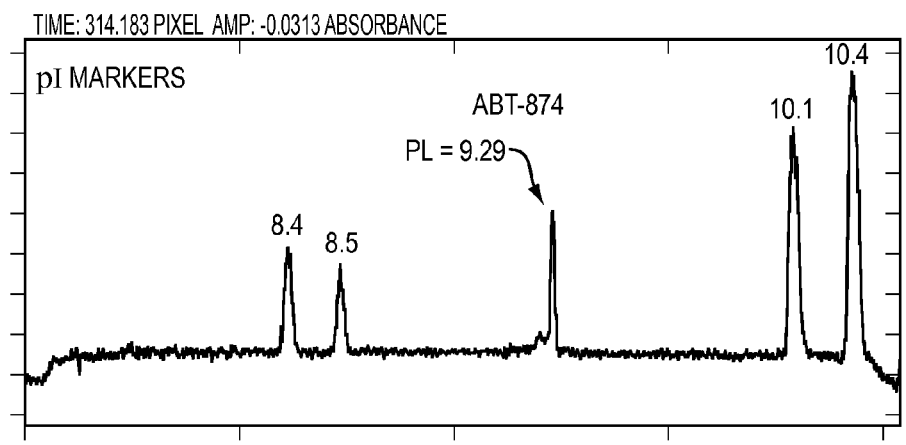

The following samples were analyzed:
ABT-874 crystal buffer (washing buffer from example 35)
ABT-874 crystals (obtained according to Example 33, in washing buffer from example 35)
Reference Standard (ABT-874 liquid sample)
The results are shown in the attached FIGS. 6A to C.

Example 43

Retention of Native Secondary Structure Upon Crystallization/Redissolution of Crystals IR spectra were recorded with a Confocheck system on a Bruker Optics Tensor 27 according to manufacturers instructions. Liquid samples were analyzed using a MicroBiolytics AquaSpec cell. Measurements of protein suspensions were performed with a Harrick BioATRII Cell™. Each sample was assessed by performing at least two measurements of 120 to 500 scans at 25° C. Blank buffer spectra were subtracted from the protein spectra, respectively. Protein second derivative spectra were generated by Fourier transformation and vector normalised from 1580-1720 cm$^{-1}$ for relative comparison.

Redissolution of crystals was performed as follows. Crystal suspensions were centrifuged, the supernatant discarded, and the crystal pellet was dissolved in 0.1 M sodium acetate buffer pH 5.5 to 10 mg/mL protein concentration.

Figure 11A:
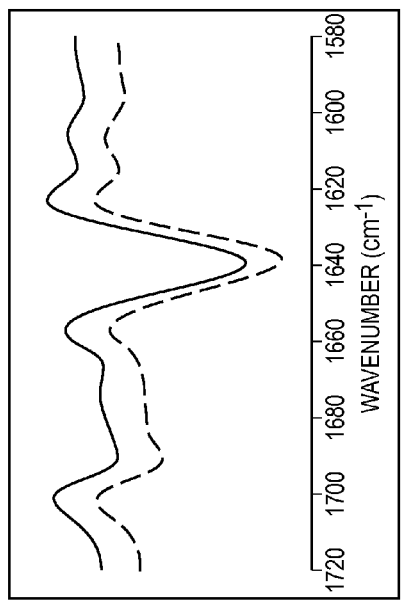
FIGS. 11A-B show second derivative IR spectra of ABT-874 samples.
Figure 12A:
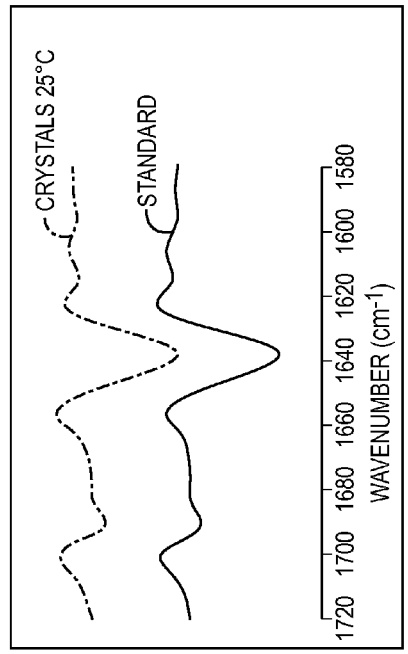
FIGS. 12A-B show second derivative IR spectra of ABT-874 samples, 50 mg/mL crystalline protein in 22% PEG 4,000 buffer in 0.1 M sodium acetate buffer, pH 5.5, stored for 3 months at 25° C.
Figure 11B:
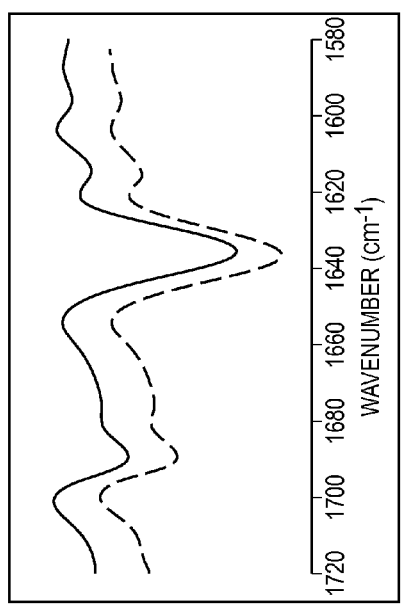
Figure 12B:
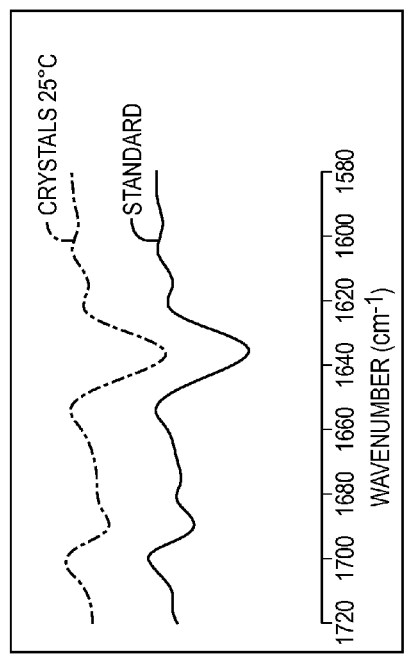

FIG. 11 depicts FT-IR second derivative spectra of crystalline ABT-874 suspensions, which were crystallized following the process as described in Example 34b, washed following the procedure introduced in Example 35, and redissolved. The spectra demonstrate that no significant alterations of the secondary structure were observed, either in the crystalline solid state or after redissolution.

Example 44

Stability Data (SE HPLC, FT-IR, Morphology)

ABT-874 was crystallized using the crystallization procedure described in Example 34b. The crystals were washed as described in Example 35, with a dispersion buffer containing 22% PEG 4,000 and 0.1 M sodium acetate and the pH was adjusted to 5.5 with acetic acid glacial. Subsequently, the crystals were concentrated to 5 mg/mL and 50 mg/mL protein by centrifugation, respectively, and stored at 2-8° C.

Stability data of 5 mg/ml and 50 mg/mL crystalline ABT-874 over 3 months storage at 2-8° C. indicated retention of above 90% monomer.

(a) SE-HPLC

TABLE 2

Stability Data of 5 mg/mL crystalline ABT-874 after redissolution

| Time point | Aggregates (%) | Monomer (%) | Fragments (%) |
|---|---|---|---|
| T0 | 3.9 | 95.8 | 0.3 |
| 1 months | 5.7 | 94.0 | 0.3 |
| 3 months | 8.7 | 91.0 | 0.3 |

TABLE 3

Stability Data of 50 mg/mL crystalline ABT-874 after redissolution

| Time point | Aggregates (%) | Monomer (%) | Fragments (%) |
|---|---|---|---|
| T0 | 3.8 | 96.0 | 0.2 |
| 1 months | 4.6 | 95.0 | 0.4 |
| 3 months | 6.3 | 93.4 | 0.3 |

A Dionex HPLC system (P680 pump, ASI 100 autosampler, UVD170U) was used to measure stability of the ABT-874 antibody. ABT-874 samples were separated on a GE Superdex® 200 column, applying a flow rate of 0.75 mL/min. Detection was carried out at a wavelength of 214 nm. The running buffer consisted of 0.2 M di sodium sulphate in 0.09 M sodium phosphate buffer, pH 7.0.

(b) FT-IR

IR spectra were recorded with a Confocheck system on a Bruker Optics Tensor 27. Liquid samples were analyzed using a MicroBiolytics AquaSpec cell. Measurements of protein suspensions were performed with a Harrick BioATRII Cell™ Each sample was assessed by performing at least two measurements of 120 to 500 scans at 25° C. Blank buffer spectra were subtracted from the protein spectra, respectively. Protein second derivative spectra were generated by Fourier transformation and vector normalised from 1580-1720 cm$^{-1}$ for relative comparison.

Redissolution of crystals was performed as follows. Crystal suspensions were centrifuged, the supernatant discarded, and the pellet was dissolved in 0.1 M sodium acetate buffer pH 5.5 to 10 mg/mL protein concentration.

Figure 2:
FIGS. 2 to 5 show SEMs of ABT-874 crystals at different magnification.
Figure 3:
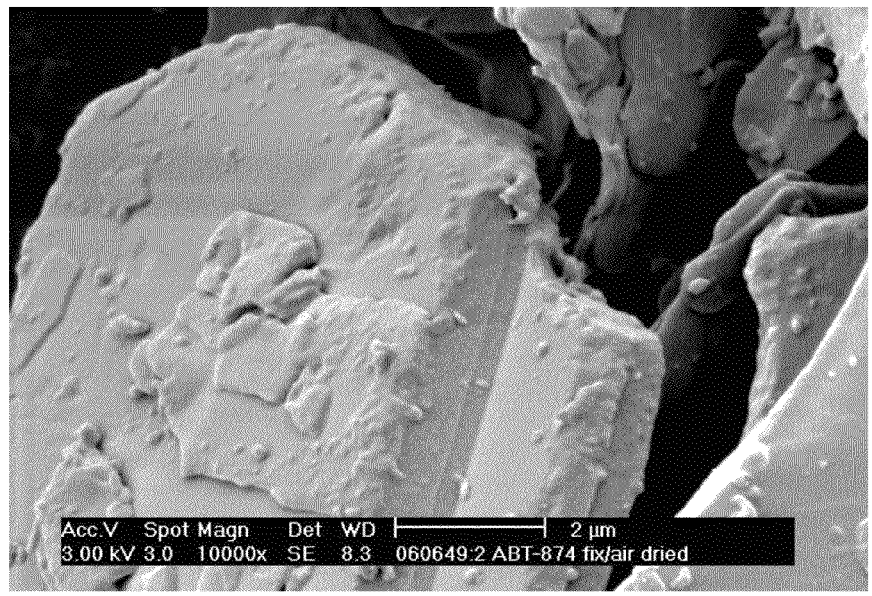
Figure 4:
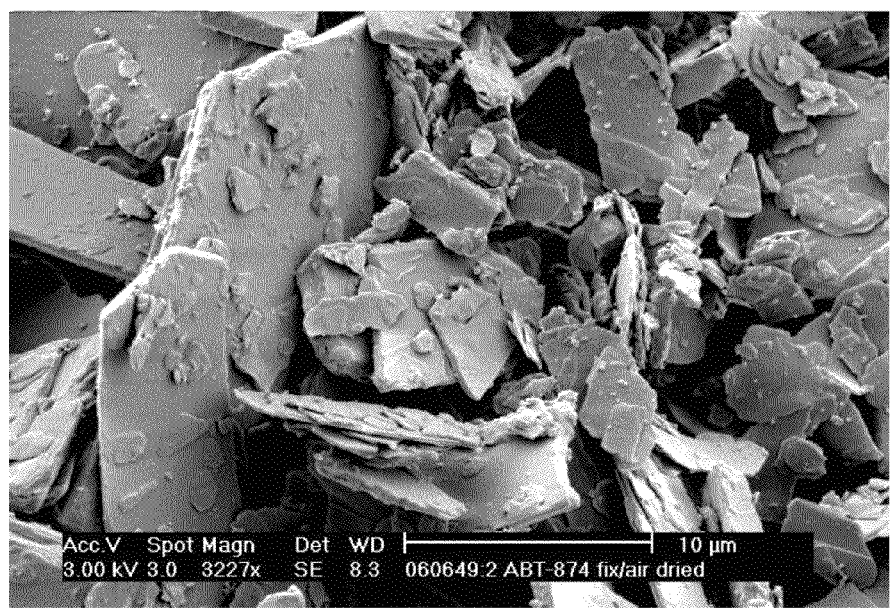
Figure 5:
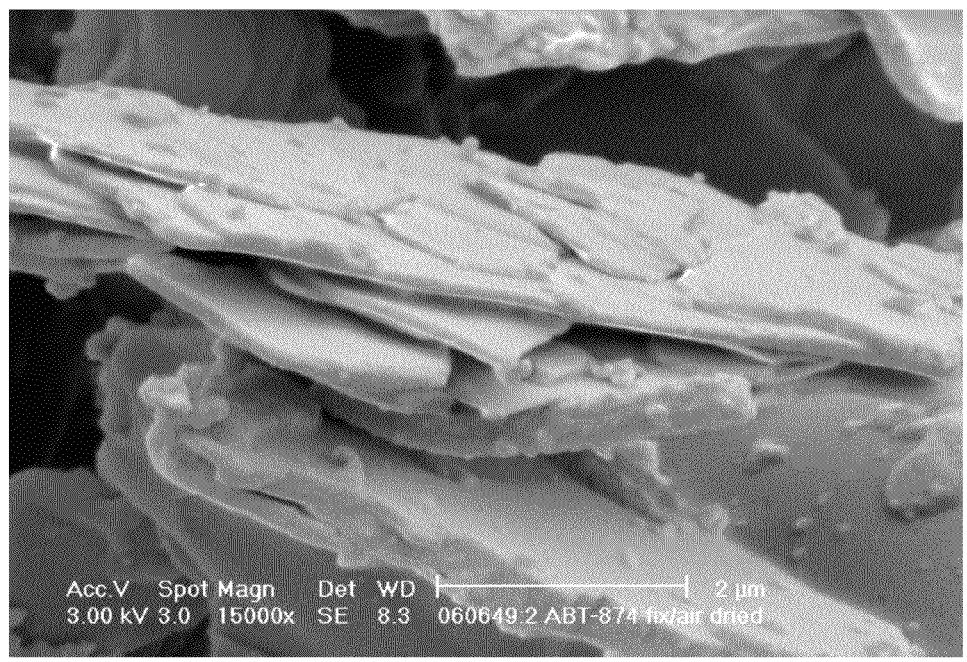

FIG. 2 depicts FT-IR second derivative spectra of crystalline ABT-874 suspensions (50 mg/mL shelf stability samples, prepared as described above and stored for 3 months at 25° C.) and after redissolution of such pre-treated crystals. The spectra demonstrate that no significant alterations of the secondary structure were observed upon storage at 25° C. for three months, either in the crystalline solid state or after redissolution.

(c) Morphology

After 3 months storage at 2-8° C., no significant morphological change was observed in light microscopy analysis of the crystals. Aliquots of 1 to 10 μL sample volume were pipetted onto an object holder plate, diluted with formulation buffer (22% PEG) and covered with a glass cover slide. The preparations were assessed using a Zeiss Axiovert 25 inverted light microscope equipped with E-PI 10× oculars and 10×, 20× and 40× objectives, respectively.

Example 45

Yield Extension of the Crystallization Process

The endpoint of a crystallization process can be defined as the time point when $OD_{280}$ measurements of aliquots of the supernatant of the crystallization slurry are constant, e.g., for three subsequent days. A yield extension is possible by adding a certain amount of additional PEG 4,000 (50% w/v solution in around 0.1 M sodium acetate buffer at a pH of around 5.5) to the supernatant of the crystallization slurry. Crystals that are similar to the first crop form during the following days. Applying this procedure, the overall yield is easily driven beyond 90%, without the introduction of precipitation.

For example, the PEG 4,000 concentration is raised from around 11% w/v to around 22% w/v, around 20% w/v, around 18% w/v, around 16% w/v, or around 14% w/v, in aliquots of the supernatant of Example 34b. After storage for several days at ambient temperature (e.g., between about 20 and about 25° C.), precipitated species are observed at certain PEG 4,000 concentrations, e.g., around 22% w/v, around 20% w/v or around 18% w/v PEG 4,000. Crystals without concomitant precipitation are found at lower PEG 4,000 concentrations, e.g., at around 16% w/v and around 14% w/v PEG 4,000. By adding PEG 4,000 to an overall concentration of, e.g., around 14% w/v to the residual supernatant of the crystallization slurry, the overall crystal yield is driven from around 60% to around 70% to over 90% in a few days.

Example 46

Yield Extension Applying a Continuous Process

In this example, additional precipitant and/or protein is "titrated" to a crystallization batch (optionally containing a certain amount of crystallization agent) at a predefined rate. Continuous crystallization over time is induced, finally resulting in over 90% crystal yield.

Example 47

Seeding of ABT-874 Crystallization Batches

Spontaneous nucleation is statistic in nature. Seeds, which might consist of the same protein (homogeneous seeding) or another substance (heterogeneous seeding) than the one being crystallized, provide a template on which further molecules can assemble. Thus, seeding may thereby accelerate crystallization.

An ABT-874 crystallization batch was prepared as described in Example 34b. After mixing the protein solution with the crystallization buffer, the mixture was seeded by homogeneous seeding with ABT-874 crystals. For example, an aliquot of a crystal suspension prepared as described in Example 34b, exhibiting around 50 to 60% crystal yield, was added, e.g., in a 1/20 ratio (v/v) to the crystallization batch. Applying this strategy, total crystal yields and process durations were further optimized towards higher yields in shorter process times.

Figure 13:
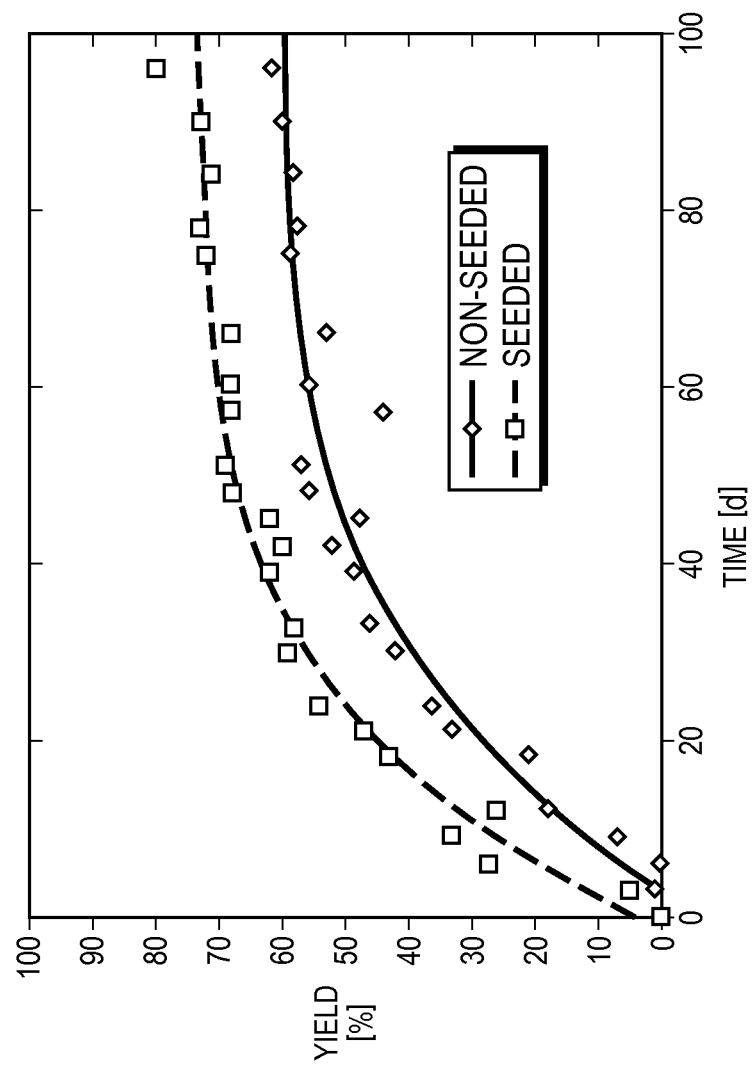
FIG. 13: 40 mL batch crystallization of ABT-874 with and without seeding (e.g., using 3.25% crystallized protein as seeding material in relation to ABT-874 mass from the batch). $R^2$ are 0.9711 for non seeded, and 0.9763 for the seeded batch, respectively.

Briefly, an ABT-874 crystallization mixture (5 mg/mL protein and 11% PEG 4,000 in 0.1M acetate buffer pH 5.5) was prepared and divided into two 40 mL aliquots. The first batch was stored at RT without further procedures and the second batch was seeded by adding 2 mL of a crystallization mixture of the same composition that already exhibited 65% of crystal yield (6.5 mg seeds, calculated on the base of crystallized protein, in comparison to 200 mg ABT-874 in the batch). The plots depicted in FIG. 13 illustrate that by applying this seeding approach, the overall yield was extended by around 15% within 80 days, whereas the parallel curve progression suggested that process times to reach maximum yield were not significantly reduced. FIG. 13 suggests that although the non-seeded batch reached a plateau of yield after around 80 days, the theoretically possible yield might be as high as for the seeded batch, meaning that seeding reduced the duration of the crystallization process rather than extending the yield.

INCORPORATION BY REFERENCE

The contents of all cited references (including literature references, patents, patent applications, and websites) that maybe cited throughout this application are hereby expressly incorporated by reference in their entirety, as are the references cited therein. The practice of the present invention will employ, unless otherwise indicated, conventional techniques of crystallization and formulation, which are well known in the art.

EQUIVALENTS

The invention may be embodied in other specific forms without departing from the spirit or essential characteristics thereof. The foregoing embodiments are therefore to be considered in all respects illustrative rather than limiting of the invention described herein. Scope of the invention is thus indicated by the appended claims rather than by the foregoing description, and all changes that come within the meaning and range of equivalency of the claims are therefore intended to be embraced herein.

---

The invention claimed is:

1. A crystal of an anti-human IL-12 antibody comprising a light chain variable region (LCVR) comprising the amino acid sequence of SEQ ID NO: 2, and a heavy chain variable region (HCVR) comprising the amino acid sequence of SEQ ID NO: 1, and wherein said crystal has a length of about 2-500 µm.

2. The crystal according to claim 1, wherein the antibody is ABT-874.

3. A method for treating a mammal comprising the step of administering to the mammal an effective amount of a pharmaceutical composition, wherein the pharmaceutical composition comprises: (a) a crystal of an anti-human IL-12 antibody according to claim 1, and (b) at least one pharmaceutical excipient, thereby treating said mammal.

4. A method for treating a mammal comprising the step of administering to the mammal an effective amount of a pharmaceutical composition, wherein the pharmaceutical composition comprises: (a) a crystal of an anti-human IL-12 antibody according to claim 1, and (b) at least one pharmaceutical excipient, which embeds or encapsulates the crystal.

5. The method according to claim 3 or 4, wherein the composition has an antibody concentration greater than about 1 mg/ml.

6. The method according to claim 5, wherein the composition has an antibody concentration greater than about 200 mg/ml.

7. The method according to claim 3 or 4, wherein the composition comprises at least one carrier selected from the group consisting of a polymeric biodegradable carrier, a polymeric non-biodegradable carrier, an oil carrier, and a lipid carrier.

8. The method according to claim 7, wherein the polymeric carrier is a polymer selected from one or more of the group consisting of: poly (acrylic acid), poly (cyanoacrylates), poly (amino acids), poly (anhydrides), poly (depsipeptide), poly (esters), poly (lactic acid), poly (lactic-co-glycolic acid) or PLGA, poly (β-hydroxybutryate), poly (caprolactone), poly (dioxanone); poly (ethylene glycol), poly (hydroxypropyl) methacrylamide, poly[(organo) phosphazene, poly (ortho esters), poly (vinyl alcohol), poly (vinylpyrrolidone), maleic anhydride alkyl vinyl ether copolymers, pluronic polyols, albumin, alginate, cellulose and cellulose derivatives, collagen, fibrin, gelatin, hyaluronic acid, oligosaccharides, glycaminoglycans, sulfated polysaccharides, blends and copolymers thereof.

9. The method according to claim 3 or 4, wherein the composition is an injectable liquid composition having an antibody concentration in the range of about 10 to about 400 mg/ml.

10. The method according to claim 3 or 4, wherein the composition is a crystal slurry composition having an antibody concentration greater than about 100 mg/ml.

11. The method according to claim 3 or 4, wherein the composition is administered by a parenteral route, an oral route, or by an injection.

12. A method of treating an IL-12-related disorder in a subject, which method comprises administering to said subject a therapeutically effective amount of a crystal of an anti-human IL-12 antibody, comprising a light chain variable region (LCVR) comprising the amino acid sequence of SEQ ID NO: 2, and a heavy chain variable region (HCVR) comprising the amino acid sequence of SEQ ID NO: 1, and wherein said crystal has a length of about 2-500 µm, thereby treating said subject.

13. The method of claim 12, wherein the IL-12-related disorder is selected from the group consisting of rheumatoid arthritis, osteoarthritis, juvenile chronic arthritis, Lyme arthritis, psoriatic arthritis, reactive arthritis, spondyloarthropathy, systemic lupus erythematosus, Crohn's disease, ulcerative colitis, inflammatory bowel disease, insulin dependent diabetes mellitus, thyroiditis, asthma, allergic diseases, psoriasis, dermatitis scleroderma, atopic dermatitis, graft versus host disease, organ transplant rejection, acute or chronic immune disease associated with organ transplantation, sarcoidosis, atherosclerosis, disseminated intravascular coagulation, Kawasaki's disease, Grave's disease, nephrotic syndrome, chronic fatigue syndrome, Wegener's granulomatosis, Henoch-Schoenlein purpurea, microscopic vasculitis of the kidneys, chronic active hepatitis, uveitis, septic shock, toxic shock syndrome, sepsis syndrome, cachexia, infectious diseases, parasitic diseases, acquired immunodeficiency syndrome, acute transverse myelitis, Huntington's chorea, Parkinson's disease, Alzheimer's disease, stroke, primary biliary cirrhosis, hemolytic anemia, malignancies, heart failure, myocardial infarction, Addison's disease, sporadic, polyglandular deficiency type I and polyglandular deficiency type II, Schmidt's syndrome, adult (acute) respiratory distress syndrome, alopecia, alopecia greata, seronegative arthopathy, arthropathy, Reiter's disease, psoriatic arthropathy, ulcerative colitic arthropathy, enteropathic synovitis, chlamydia, yersinia and salmonella associated arthropathy, spondyloarthopathy, atheromatous disease/arteriosclerosis, atopic allergy, autoimmune bullous disease, pemphigus vulgaris, pemphigus foliaceus, pemphigoid, linear IgA disease, autoimmune haemolytic anaemia, Coombs positive haemolytic anaemia, acquired pernicious anaemia, juvenile pernicious anaemia, myalgic encephalitis/Royal Free Disease, chronic mucocutaneous candidiasis, giant cell arteritis, primary sclerosing hepatitis, cryptogenic autoimmune hepatitis, Acquired Immunodeficiency Disease Syndrome, Acquired Immunodeficiency Related Diseases, Hepatitis C, common varied immunodeficiency (common variable hypogammaglobulinaemia), dilated cardiomyopathy, female infertility, ovarian failure, premature ovarian failure, fibrotic lung disease, cryptogenic fibrosing alveolitis, post-inflammatory interstitial lung disease, interstitial pneumonitis, connective tissue disease associated interstitial lung disease, mixed connective tissue disease associated lung disease, systemic sclerosis associated interstitial lung disease, rheumatoid arthritis associated interstitial lung disease, systemic lupus erythematosus associated lung disease, dermatomyositis/polymyositis associated lung disease, Sjodgren's disease associated lung disease, ankylosing spondylitis associated lung disease, vasculitic diffuse lung disease, haemosiderosis associated lung disease, drug-induced interstitial lung disease, radiation fibrosis, bronchiolitis obliterans, chronic eosinophilic pneumonia, lymphocytic infiltrative lung disease, postinfectious interstitial lung disease, gouty arthritis, autoimmune hepatitis, type-1 autoimmune hepatitis (classical autoimmune or lupoid hepatitis), type-2 autoimmune hepatitis (anti-LKM antibody hepatitis), autoimmune mediated hypoglycemia, type B insulin resistance with acanthosis nigricans, hypoparathyroidism, acute immune disease associated with organ transplantation, chronic immune disease associated with organ transplantation, osteoarthrosis, primary sclerosing cholangitis, idiopathic leucopenia, autoimmune neutropenia, renal disease NOS, glomerulonephritides, microscopic vasulitis of the kidneys, lyme disease, discoid lupus erythematosus, male infertility idiopathic or NOS, sperm autoimmunity, multiple sclerosis (all subtypes), insulin-dependent diabetes mellitus, sympathetic ophthalmia, pulmonary hypertension secondary to connective tissue disease, Goodpasture's syndrome, pulmonary manifestation of polyarteritis nodosa, acute rheumatic fever, rheumatoid spondylitis, Still's disease, systemic sclerosis, Takayasu's disease/arteritis, autoimmune thrombocytopenia, idiopathic thrombocytopenia, autoimmune thyroid disease, hyperthyroidism, goitrous autoimmune hypothyroidism (Hashimoto's disease), atrophic autoimmune hypothyroidism, primary myxoedema, phacogenic uveitis, primary vasculitis and vitiligo.

14. A method for treating a mammal comprising the step of administering to the mammal an effective amount of a crystal of an anti-human IL-12 antibody, comprising a light chain variable region (LCVR) comprising the amino acid sequence of SEQ ID NO: 2, and a heavy chain variable region (HCVR) comprising the amino acid sequence of SEQ ID NO: 1, and wherein said crystal has a length of about 2-500 µm, thereby treating said mammal.

15. The method according to claim 14, wherein the crystal has a sword-like morphology.

16. The method according to claim 15, wherein the antibody is an IgG antibody.

17. The method according to claim 16, wherein the antibody is selected from the group consisting of an IgG1, an IgG2, an IgG3 and an IgG4 antibody.

18. The method according to claim 17, wherein the antibody is an anti-human IL-12 antibody of the group IgG1.

19. The method according to claim 18, wherein the crystal is prepared from an isolated human antibody that dissociates from human IL-12 with a $K_d$ of $1 \times 10^{-10}$ M or less and a $k_{off}$ rate constant of $1 \times 10^{-3}$ $s^{-1}$ or less, both determined by surface plasmon resonance.

* * * * *

UNITED STATES PATENT AND TRADEMARK OFFICE
CERTIFICATE OF CORRECTION

PATENT NO.        : 8,940,873 B2
APPLICATION NO.   : 13/762171
DATED             : January 27, 2015
INVENTOR(S)       : David W. Borhani et al.

It is certified that error appears in the above-identified patent and that said Letters Patent is hereby corrected as shown below:

In the Claims:

In claim 13 (column 55, line 44), replace "greata" with --areata--.

Signed and Sealed this
Twenty-sixth Day of May, 2015

Michelle K. Lee
*Director of the United States Patent and Trademark Office*